US011890335B2

(12) United States Patent
Mamula et al.

(10) Patent No.: US 11,890,335 B2
(45) Date of Patent: Feb. 6, 2024

(54) ERBB PEPTIDE PHARMACEUTICAL AND VACCINE COMPOSITIONS AND THERAPEUTIC USES THEREOF FOR CANCER

(71) Applicants: L2 Diagnostics, LLC, New Haven, CT (US); Yale University, New Haven, CT (US)

(72) Inventors: Mark Mamula, Madison, CT (US); Raymond A. Koski, Old Lyme, CT (US)

(73) Assignees: L2 Diagnostics, LLC, New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 16/651,037

(22) PCT Filed: Sep. 27, 2018

(86) PCT No.: PCT/US2018/053046
§ 371 (c)(1),
(2) Date: Mar. 26, 2020

(87) PCT Pub. No.: WO2019/067673
PCT Pub. Date: Apr. 4, 2019

(65) Prior Publication Data
US 2020/0246444 A1 Aug. 6, 2020

Related U.S. Application Data

(60) Provisional application No. 62/563,850, filed on Sep. 27, 2017.

(51) Int. Cl.
*A61K 39/00* (2006.01)
*A61P 35/00* (2006.01)
*A61K 9/00* (2006.01)

(52) U.S. Cl.
CPC ...... *A61K 39/001106* (2018.08); *A61P 35/00* (2018.01); *A61K 9/0019* (2013.01); *A61K 2039/552* (2013.01); *A61K 2039/55544* (2013.01); *A61K 2039/55566* (2013.01); *A61K 2039/55594* (2013.01); *A61K 2039/6081* (2013.01)

(58) Field of Classification Search
CPC .......... A61K 39/001106; A61P 35/00
See application file for complete search history.

(56) References Cited

U.S. PATENT DOCUMENTS

| 6,455,498 | B1 | 9/2002 | Vogelstein et al. | |
| 2002/0136735 | A1* | 9/2002 | Molina | A61K 39/001106 424/190.1 |
| 2008/0057064 | A1* | 3/2008 | Zhou | C07K 14/4747 424/139.1 |
| 2009/0286737 | A1* | 11/2009 | Greene | A61K 47/6809 514/8.5 |
| 2012/0183552 | A1 | 7/2012 | Joseloff et al. | |
| 2013/0108547 | A1 | 5/2013 | Dunbrack et al. | |
| 2013/0217857 | A1 | 8/2013 | Greene et al. | |
| 2020/0246444 | A1 | 8/2020 | Mamula et al. | |

FOREIGN PATENT DOCUMENTS

WO WO-02/081649 A2 10/2002
WO WO-2014139672 A1 * 9/2014 ..... A61K 39/001106

OTHER PUBLICATIONS

Gil et al. "Vaccination with ErbB-2 peptides prevents cancer stem cell expansion and suppresses the development of spontaneous tumors in MMTV-PyMT transgenic mice", Breast Cancer Res Treat. Aug. 2014; 147(1):69-80 (Year: 2014).*
Wiedermann et al. "A virosomal formulated Her-2/neu multi-peptide vaccine induces Her-2/neu-specific immune responses in patients with metastatic breast cancer: a phase I study", Breast Cancer Res Treat. Feb. 2010; 119(3):673-83 (Year: 2010).*
Dakappagari et al., A chimeric multihuman epidermal growth factor receptor-2 B cell epitope peptide vaccine mediates superior antitumor responses., J. Immunol., 170: 4242-4253 (2003).
Dakappagari et al., "Conformational HER-2/neu B-cell epitope peptide vaccine designed to incorporate two native disulfide bonds enhances tumor cell binding and antitumor activities," J Biol Chem, 280(1): 54-63 (2005).
Dakappagari et al., "Prevention of mammary tumors with a chimeric HER-2 B-cell epitope peptide vaccine," Cancer Res, 60: 3782-3789 (2000).
Garrett et al., 2007. "Novel engineered trastuzumab conformational epitopes demonstrate in vitro and in vivo antitumor properties against HER-2/neu," J Immunol, 178: 7120-7131 (2007).
International Search Report and Written Opinion for International Application No. PCT/US18/53036 dated Mar. 7, 2019.
Bockenstedt et al., "Self-peptides in the initiation of lupus autoimmunity," The Journal of Immunology, 154: 3516-3524 (1995).
Doyle et al., "Epidermal growth factor receptor peptide vaccination induces cross-reactive immunity to human EGFR, HER2, and HER3," Cancer Immunol Immunother, 67: 1559-1569 (2018).
Erdile et al., "OspA lipoprotein of Borrelia burgdorferi is a mucosal iummunogen and adjuvant," Vaccine, 15(9): 988-996 (1997).
Extended European Search Report for EP Application No. EP 18863363 dated Oct. 13, 2021.
Mamula., "The Inability to Process a Self-Peptide Allows Autoreactive T Cells to Escape Tolerance," The Journal of Experimental Medicine, 177: 567-571 (1993).

* cited by examiner

Primary Examiner — Amy E Juedes
Assistant Examiner — Peter Johansen
(74) Attorney, Agent, or Firm — Foley Hoag LLP; Hathaway P. Russell

(57) ABSTRACT

Disclosed herein are peptide-adjuvant pharmaceutical compositions and vaccine compositions that trigger long lasting natural anti-tumor antibodies. Such compositions may be used alone, or in combination with anti-cancer agents, chemotherapeutic agents, anti-PD therapy, chemotherapy, radiation therapy, and surgery, in the prevention and treatment of cancer.

28 Claims, 31 Drawing Sheets
Specification includes a Sequence Listing.

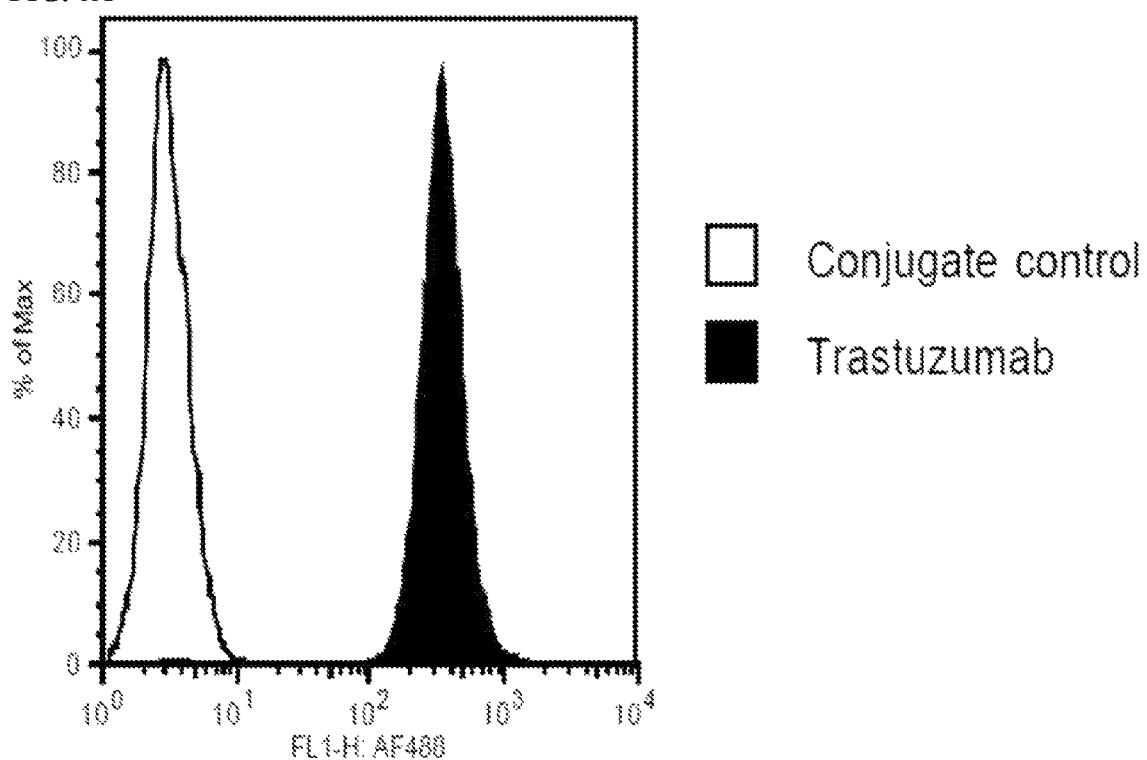

| Adjuvant | Positive IgG Response |
|---|---|
| IFA | 10/19 (53%) |
| Montanide ISA 51VG | 23/33 (70%) |

SEQUENCE LISTING

```
<160> NUMBER OF SEQ ID NOS: 15

<210> SEQ ID NO 1
<211> LENGTH: 19
<212> TYPE: PRT
<213> ORGANISM: Homo sapiens

<400> SEQUENCE: 1

Ile Gln Cys Ala His Tyr Ile Asp Gly Pro His Cys Val Lys Thr Cys
1               5                   10                  15

Pro Ala Gly

<210> SEQ ID NO 2
<211> LENGTH: 19
<212> TYPE: PRT
<213> ORGANISM: Homo sapiens

<400> SEQUENCE: 2

Val Ala Cys Ala His Tyr Lys Asp Pro Pro Phe Cys Val Ala Arg Cys
1               5                   10                  15

Pro Ser Gly

<210> SEQ ID NO 3
<211> LENGTH: 19
<212> TYPE: PRT
<213> ORGANISM: Homo sapiens

<400> SEQUENCE: 3

Ala Gln Cys Ala His Phe Arg Asp Gly Pro His Cys Val Ser Ser Cys
1               5                   10                  15

Pro His Gly

<210> SEQ ID NO 4
<211> LENGTH: 19
<212> TYPE: PRT
<213> ORGANISM: Homo sapiens

<400> SEQUENCE: 4

Thr Lys Cys Ser His Phe Lys Asp Gly Pro Asn Cys Val Glu Lys Cys
1               5                   10                  15

Pro Asp Gly

<210> SEQ ID NO 5
<211> LENGTH: 19
<212> TYPE: PRT
<213> ORGANISM: Artificial Sequence
<220> FEATURE:
<223> OTHER INFORMATION: synthetic peptide

<400> SEQUENCE: 5

Ala Met Asn Ile Thr Cys Thr Gly Arg Gly Pro Asp Asn Cys Ile Gln
1               5                   10                  15

Cys Ala His
```

```
<210> SEQ ID NO 6
<211> LENGTH: 19
<212> TYPE: PRT
<213> ORGANISM: Artificial Sequence
<220> FEATURE:
<223> OTHER INFORMATION: synthetic peptide

<400> SEQUENCE: 6

Ile Gln Cys Ala His Tyr Ile Asp Gly Pro His Cys Val Lys Thr Ser
1               5                   10                  15

Pro Ala Gly

<210> SEQ ID NO 7
<211> LENGTH: 19
<212> TYPE: PRT
<213> ORGANISM: Artificial Sequence
<220> FEATURE:
<223> OTHER INFORMATION: synthetic peptide

<400> SEQUENCE: 7

Ile Gln Cys Ala His Tyr Ile Asp Gly Pro His Cys Val Lys Thr Ser
1               5                   10                  15

Pro Ala Gly

<210> SEQ ID NO 8
<211> LENGTH: 20
<212> TYPE: PRT
<213> ORGANISM: Artificial Sequence
<220> FEATURE:
<223> OTHER INFORMATION: synthetic peptide

<400> SEQUENCE: 8

Ile Gln Cys Ala His Tyr Ile Asp Gly Pro His Cys Val Lys Thr Ser
1               5                   10                  15

Pro Ala Gly Lys
            20

<210> SEQ ID NO 9
<211> LENGTH: 19
<212> TYPE: PRT
<213> ORGANISM: Artificial Sequence
<220> FEATURE:
<223> OTHER INFORMATION: synthetic peptide

<400> SEQUENCE: 9

Ile Gln Cys Ala His Tyr Ile Asp Pro Pro His Cys Val Lys Thr Ser
1               5                   10                  15

Pro Ala Gly

<210> SEQ ID NO 10
<211> LENGTH: 19
<212> TYPE: PRT
<213> ORGANISM: Artificial Sequence
<220> FEATURE:
<223> OTHER INFORMATION: synthetic peptide

<400> SEQUENCE: 10

Ile Gln Cys Ala His Tyr Ile Asp Gly Pro His Cys Val Lys Thr Ser
1               5                   10                  15

Pro Ala Gly

<210> SEQ ID NO 11
```

```
<211> LENGTH: 19
<212> TYPE: PRT
<213> ORGANISM: Artificial Sequence
<220> FEATURE:
<223> OTHER INFORMATION: synthetic peptide

<400> SEQUENCE: 11

Thr Gly Arg Gly Pro Asp Asn Cys Ile Gln Cys Ala His Tyr Ile Asp
1               5                   10                  15

Gly Pro His

<210> SEQ ID NO 12
<211> LENGTH: 20
<212> TYPE: PRT
<213> ORGANISM: Mus musculus

<400> SEQUENCE: 12

Pro Ala Gly Ile Met Gly Glu Asn Asn Thr Leu Val Trp Lys Tyr Ala
1               5                   10                  15

Asp Ala Asn Asn
            20

<210> SEQ ID NO 13
<211> LENGTH: 20
<212> TYPE: PRT
<213> ORGANISM: Homo sapiens

<400> SEQUENCE: 13

Pro Ala Gly Val Met Gly Glu Asn Asn Thr Leu Val Trp Lys Tyr Ala
1               5                   10                  15

Asp Ala Gly His
            20

<210> SEQ ID NO 14
<211> LENGTH: 19
<212> TYPE: PRT
<213> ORGANISM: Mus musculus

<400> SEQUENCE: 14

Thr Leu Val Trp Lys Tyr Ala Asp Ala Asn Asn Val Cys His Leu Cys
1               5                   10                  15

His Ala Asn

<210> SEQ ID NO 15
<211> LENGTH: 19
<212> TYPE: PRT
<213> ORGANISM: Canis lupus

<400> SEQUENCE: 15

Ile Lys Cys Ala His Tyr Ile Asp Gly Pro His Cys Val Lys Thr Cys
1               5                   10                  15

Pro Ala Gly
```

ERBB PEPTIDE PHARMACEUTICAL AND VACCINE COMPOSITIONS AND THERAPEUTIC USES THEREOF FOR CANCER

RELATED APPLICATION

This application is a national stage filing under 35 U.S.C. § 371 of PCT/US18/53046, filed on Sep. 27, 2018, which claims the benefit of U.S. Provisional Application No. 62/563,850, filed on Sep. 27, 2017. The contents of these applications are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Nov. 28, 2018, is named LDA-00225 Sequence Listing.txt and is 4.10 KB in size.

BACKGROUND

Epidermal growth factor receptor (EGFR) is a 170 kDa surface glycoprotein that is over expressed in a variety of solid tumors and is associated with more aggressive tumor growth and a poorer prognosis (Sartor C I (2000) *Semin Oncol* 27: 15-20; discussion 92-100; Chen X et al. (2000) *Biochem Biophys Res Commun* 277: 757-63; Fischer-Colbrie J et al. (1997) *Anticancer Res* 17: 613-9; Magne N et al. (2001) *Eur J Cancer* 37: 2169-77; Sok J C et al. (2006) *Clin Cancer Res* 12: 5064-73; Lu Y et al. (2012) *Cancer Biomark* 11: 219-26; Milella M et al. (2012) *J Thorac Oncol* 7: 672-80). A number of therapeutic anti-EGFR monoclonal antibodies exist, although the most widely recognized for advanced colorectal cancer is cetuximab (Erbitux®). Cetuximab has been used as a single therapy, with chemotherapy, and in combination with other EGFR targeted therapies, such as small-molecule inhibitors of tyrosine kinase activity (Vecchione L et al. (2011) *Exp Cell Res* 317: 2765-71).

Although monoclonal antibodies represent a major advance in cancer treatment, there remain drawbacks and failures to this therapeutic approach. Monoclonal antibody therapy provides no long lasting immunity, allowing tumor recurrence to arise without any immunological surveillance in place. Additionally, this therapy is complicated by the high cost of treatment and the side effects associated with multiple infusions of the drug (Fojo T et al. (2009) *J Natl Cancer Inst* 101: 1044-8). Patients with a therapeutic response to cetuximab as a first line of therapy often develop resistance to the antibody and subsequent tumor progression (Jackman D et al. (2010) *J Clin Oncol* 28: 357-60; Chaft J E et al. (2011) *Clin Cancer Res* 17: 6298-303; Troiani T et al. (2013) *Expert Opin Biol Ther* 13: 241-55). Resistance can arise when other ErbB family members (HER2, HER3, HER4) compensate for the signaling loss of EGFR, thereby triggering further tumor outgrowth. ErbB family members form heterodimers with each other, thus forming several signaling pathways that compensate for the loss of individual ErbB receptors. Several studies have demonstrated the in vitro and in vivo efficacy of dual specificity antibodies against EGFR and HER3 (Schaefer G et al. (2011) *Cancer Cell* 20: 472-86; Huang S M et al. (2012) *Cancer Res* 73:824-33) as well as the simultaneous targeting of EGFR and HER2 (Larbouret C et al. (2012) *Neoplasia* 14: 121-30). MEHD7945A is a novel "two-in-one" human monoclonal antibody against both EGFR and HER3 with enhanced inhibitory activity when compared with monospecific antibodies (Schaefer G et al. (2011) *Cancer Cell* 20: 472-86). MEHD7945A was evaluated in clinical trials for metastatic colorectal and head and neck carcinomas. As yet another example of the strategy of dual targeting therapeutics, lapatinib (Tykerb, GSK) is an orally available, small molecule inhibitor of both EGFR/HER2 tyrosine kinase inhibitors approved for treatment of breast cancer. The FDA approved drug, afatinib, is a small molecule inhibitor that covalently binds and irreversibly blocks signaling from all the cancer-relevant homo- and heterodimers of the ErbB family (Yang J C et al. (2012) *Lancet Oncol* 13: 539-48).

Tumor directed vaccination has reemerged as an attractive therapeutic strategy (Weiss E M et al. (2012) *Front Oncol* 2: 132). Effective vaccination would provide long lasting immunity and surveillance that would be in place should a tumor reoccur. Rindopepimut was examined in human clinical trials against EGFR variant III (EGFRvIII), a naturally occurring mutated EGFR expressed in approximately 20-30% of glioblastoma multiforme patients (Babu R et al. (2012) *Core Evid* 7: 93-103). Peptide vaccines can be totally synthetic, chemically defined, easily produced in clinical grade, free of viral and host cell contaminants, stable, conformationally constrained, and precisely directed toward specific B-cell and T-cell epitopes and elicit therapeutic immune responses. While peptides are generally poorly immunogenic, several strategies can be used to enhance immunogenicity including conjugation to KLH, cyclization, incorporating modified peptide residues, or formulations with immune enhancers and delivery in liposomes or nanoparticles.

SUMMARY OF THE INVENTION

Featured herein are ErbB peptide based pharmaceutical and vaccine compositions that are based on a membrane-proximal epitope (p580-598) in the extracellular domain of human and canine EGFR. In certain embodiments, the pharmaceutical and vaccine compositions comprise a peptide having the amino acid sequence set forth in any of SEQ ID NOs: 1-15. Such pharmaceutical and vaccine compositions may be used alone, or in combination with anti-cancer agents, chemotherapeutic agents, anti-PD therapy, chemotherapy, radiation therapy, and surgery, in the prevention and treatment of cancer.

The disclosed peptide-based vaccines trigger long lasting natural anti-tumor antibodies to ErbB/EGFR. By targeting multiple ErbB family members, the instant disclosed vaccines are expected to be more efficacious than therapies, which target a single tumor cell surface protein alone. In addition, it is relatively simple to produce cGMP quality pharmaceutical and vaccine compositions.

One aspect of the invention relates to a pharmaceutical composition comprising a peptide having: at least 90% identity to an amino acid sequence selected from the group consisting of SEQ ID: NOs: 1-15, and an adjuvant.

In some embodiments of the pharmaceutical composition, the peptide has at least 95% identity to the amino acid sequence selected from the group consisting of SEQ ID: NOs: 1-15.

In some embodiments of the pharmaceutical composition, the peptide has the amino acid sequence selected from the group consisting of SEQ ID: NOs: 1-15.

In some embodiments of the pharmaceutical composition, the peptide is an ErbB peptide.

In some embodiments of the pharmaceutical composition, the peptide is an SEQ ID NO: 15.

In some embodiments of the pharmaceutical composition, the adjuvant comprises at least one *Borrelia* antigen, receptor agonist, or immunomodulatory agent, or combinations thereof.

In some embodiments of the pharmaceutical composition, the adjuvant comprises at least one *Borrelia* antigen.

In some embodiments of the pharmaceutical composition, the at least one *Borrelia* antigen is Outer Surface Protein A (OspA), Outer Surface Protein C (OspC), or both.

In some embodiments of the pharmaceutical composition, the at least one *Borrelia* antigen induces antibodies against at least one of the *Borrelia* spp. selected from the group consisting of *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mazzottii, Borrelia merionesi, Borrelia microti, Borrelia miyamotoi, Borrelia parkeri, Borrelia persica, Borrelia recurrentis, Borrelia sinica, Borrelia spielmanii, Borrelia tanukii, Borrelia texasensis, Borrelia theileri, Borrelia tillae, Borrelia turcica, Borrelia turdi, Borrelia turicatae, Borrelia valaisiana, Borrelia venezuelensis, Borrelia vincentii, Borrelia burgdorferi* B31, *Borrelia burgdorferi* N40, *Borrelia burgdorferi* JD1, or *Borrelia burgdorferi* 297.

In some embodiments of the pharmaceutical composition, the *Borrelia* spp. is *Borrelia burgdorferi*.

In some embodiments of the pharmaceutical composition, the adjuvant is selected from LymeVax or Nobivac Lyme, or LYMErix.

In some embodiments of the pharmaceutical composition, the adjuvant comprises at least one receptor agonist.

In some embodiments of the pharmaceutical composition, the receptor is a Toll-Like Receptor (TLR) selected from the group consisting of TLR1, TLR2, TLR3, TLR4, TLR5, TLR6, TLR7, TLR8, TLR9, TLR10, TLR11, TLR12, and TLR13.

In some embodiments of the pharmaceutical composition, the at least one receptor agonist is selected from the group consisting of CpG oligodeoxynucleotides 7909 (CpG 7909), Monophosphoryl lipid A (MPL), lipopolysaccharide (LPS), polyI:C, and R848, or combinations thereof.

In some embodiments of the pharmaceutical composition, the receptor is TLR3.

In some embodiments of the pharmaceutical composition, the receptor agonist is a TLR3 agonist, said TLR3 agonist is polyI:C.

In some embodiments of the pharmaceutical composition, the receptor is TLR4.

In some embodiments of the pharmaceutical composition, the receptor agonist is a TLR4 agonist, said TLR4 agonist is MPL.

In some embodiments of the pharmaceutical composition, the receptor is TLR7.

In some embodiments of the pharmaceutical composition, the receptor agonist is a TLR7 agonist, said TLR7 agonist is R848.

In some embodiments of the pharmaceutical composition, the receptor is TLR9.

In some embodiments of the pharmaceutical composition, the receptor agonist is a TLR9 agonist, said TLR9 agonist is CpG.

In some embodiments of the pharmaceutical composition, the adjuvant is from about 5% to about 80% volume/volume (v/v).

In some embodiments of the pharmaceutical composition, the adjuvant is about 5%, about 10%, about 15%, about 20%, about 25%, about 30%, about 35%, about 40%, about 45%, about 50%, about 55%, about 60%, about 65%, about 70%, about 75%, or about 80% (v/v).

In some embodiments of the pharmaceutical composition, the adjuvant is about 15% (v/v).

In some embodiments of the pharmaceutical composition, the adjuvant comprises at least one immunomodulatory agent.

In some embodiments of the pharmaceutical composition, the immunomodulatory agent is a selected from the group consisting of complete Freunds adjuvant (CFA), incomplete Freunds adjuvant (IFA), LTK63, dimethyl dioctadecyl-ammonium bromide (DDA), lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, water-in-oil emulsion, mannide monooleate, vegetable grade (VG) oleic acid, Montanide ISA-51 VG, ISA-720, microparticles, immuno stimulatory complexes, liposomes, virosomes, virus-like particles, cholera toxin, heat-labile toxin from *E. coli*, lipoproteins, dendritic cells, IL-12, GM-CSF, nanoparticles, a combination of soybean oil, emulsifying agents, and ethanol to form a nanoemulsion, AS04, and ZADAXIN, or combinations thereof.

In some embodiments of the pharmaceutical composition, the immunomodulatory agent is CFA.

In some embodiments of the pharmaceutical composition, the immunomodulatory agent is IFA.

In some embodiments of the pharmaceutical composition, the immunomodulatory agent is Montanide ISA-51 VG.

In some embodiments of the pharmaceutical composition, the immunomodulatory agent is from about 5% to about 80% volume/volume (v/v).

In some embodiments of the pharmaceutical composition, the adjuvant is about 5%, about 10%, about 15%, about 20%, about 25%, about 30%, about 35%, about 40%, about 45%, about 50%, about 55%, about 60%, about 65%, about 70%, about 75%, or about 80% (v/v).

In some embodiments of the pharmaceutical composition, the adjuvant is about 50% (v/v).

In some embodiments of the pharmaceutical composition, the adjuvant is a combination of Montanide ISA-51 VG and LymeVax.

In some embodiments of the pharmaceutical composition, the adjuvant is a combination of Montanide ISA-51 VG and CpG 7909.

Another aspect of the invention relates to a vaccine composition comprising any of the aforementioned pharmaceutical compositions.

Another aspect of the invention relates to a method of preventing or treating cancer in a subject comprising administering to the subject any of the aforementioned pharmaceutical compositions, or any of the aforementioned vaccine compositions.

Another aspect of the invention relates to a method of preventing or treating cancer in a subject comprising administering to the subject any of the aforementioned pharmaceutical compositions, or any of the aforementioned vaccine compositions.

Another aspect of the invention relates to a method of preventing or treating cancer in a subject comprising conjointly administering to the any of the aforementioned pharmaceutical compositions, or any of the aforementioned vaccine compositions, and an anti-cancer or chemotherapeutic agent.

Another aspect of the invention relates to a method of preventing or treating cancer in a subject comprising conjointly administering to the subject any of the aforementioned pharmaceutical compositions, or any of the aforementioned vaccine compositions, and an anti-PD therapy.

In some embodiments of the methods of preventing or treating cancer, the anti-PD therapy is blockade of the PD-1/PDL1 pathway.

In some embodiments of the methods of preventing or treating cancer, the anti-PD therapy is a monoclonal antibody to PD-1.

In some embodiments of the methods of preventing or treating cancer, the anti-PD therapy is a monoclonal antibody to B7-H1/PD-L1.

In some embodiments of the methods of preventing or treating cancer, the pharmaceutical composition, anti-cancer agent, chemotherapeutic agent, or anti-PD therapy is administered separately, concomitantly, sequentially, or repeatedly.

In some embodiments of the methods of preventing or treating cancer, the pharmaceutical composition, vaccine composition, anti-cancer agent, chemotherapeutic agent, or anti-PD therapy is administered intravenously, intramuscularly, subcutaneously, or intraperitoneally.

In some embodiments of the methods of preventing or treating cancer, the pharmaceutical composition or vaccine composition is administered before, during or after administering the anti-cancer agent, chemotherapeutic agent, or anti-PD therapy. In some embodiments of the methods of preventing or treating cancer, the anti-cancer agent, chemotherapeutic agent, or anti-PD therapy, is administered at about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, 20 to 50 mg/kg, 50 to 100 mg/kg, 100 to 200 mg/kg, 200 to 300 mg/kg, 300 to 400 mg/kg, 400 to 500 mg/kg, 500 to 600 mg/kg, 600 to 700 mg/kg, 700 to 800 mg/kg, 800 to 900 mg/kg, or 900 to 1000 mg/kg.

In some embodiments of the methods of preventing or treating cancer, the anti-cancer agent, chemotherapeutic agent, or anti-PD therapy is administered at about 0.01 to 0.1 mcg/kg, 0.1 to 0.5 mcg/kg, 0.5 to 5 mcg/kg, 5 to 10 mcg/kg, 10 to 20 mcg/kg, 20 to 50 mcg/kg, 50 to 100 mcg/kg, 100 to 200 mcg/kg, 200 to 300 mcg/kg, 300 to 400 mcg/kg, 400 to 500 mcg/kg, 500 to 600 mcg/kg, 600 to 700 mcg/kg, 700 to 800 mcg/kg, 800 to 900 mcg/kg, or 900 to 1000 mcg/kg.

In some embodiments of the methods of preventing or treating cancer, the pharmaceutical composition or vaccine composition is about 0.4 mg to about 40 mg per kg body weight, about 5 mg to about 20 mg per kg, about 10 mg to about 20 mg per kg, or about 15 mg to about 25 mg per kg.

In some embodiments of the methods of preventing or treating cancer, the pharmaceutical composition or vaccine composition is about 4 mg per kg.

In some embodiments of the methods of preventing or treating cancer, the subject has received or is receiving chemotherapy or radiotherapy, or has undergone or is undergoing surgery.

In some embodiments of the methods of preventing or treating cancer, the subject is a mammal.

In some embodiments of the methods of preventing or treating cancer, the mammal is a dog.

In some embodiments of the methods of preventing or treating cancer, the mammal is a human.

Further features and advantages will become apparent from the following Detailed Description and Claims.

BRIEF DESCRIPTION OF THE DRAWINGS

FIG. 2A depicts A431 cells staining with cetuximab-AF-488. FIG. 2B depicts staining with Asp EGFR p580 antiserum-AF647 antibodies. FIG. 2C depicts costaining with cetuximab-AF488 and EGFR p580 antiserum-AF647. FIG. 2D depicts costaining with cetuximab and isoAsp EGFR p580 antiserum-AF647.

FIG. 5C shows proliferation of T cells from EGFR p580 immunized mice in response to Asp and iso-Asp isoforms of EGFR p580. FIG. 5D shows T cells from C57BL/6 mice immunized with either Asp or iso-Asp p580 were restimulated with 10 μg Asp and iso-Asp p580. Data represent background cpm subtracted from the experimental cpm. Cells stimulated with PPD (positive control) ranged from 11,000-49,000 cpm. Results represent the mean±SEM of triplicate wells.

FIG. 6A shows A431 cells stained with the anti-EGFR antibody cetuximab (positive control) or secondary antibody alone (conjugate control). FIG. 6B depicts Asp EGFR p580 immune serum binding of A431 cells. FIG. 6C depicts iso-Asp EGFR p580 immune serum binding of A431 cells. Results are representative of four mice per immunization.

FIG. 8A-FIG. 8B depicts sera from anti-EGFR peptide immune mice bind HER2-positive, EGFR-negative human MDA-MB-453 cells. Sera from Balb/c mice immunized with either Asp or iso-Asp p580 were incubated with MDA-MB-453 cells (HER2-positive, EGFR-negative) and stained for FACS analysis. FIG. 8A shows MDA-MB-453 cells stained with the anti-HER2 antibody trastuzumab (positive control). FIG. 8B depicts Aspand iso-Asp EGFR p580 immune serum binding of MDA-MB-453 cells. Cetuximab served as a control to confirm that cells are EGFR negative. Results are representative of four mice per immunization group.

FIG. 9A depicts A431 cells or FIG. 9B shows MDA-MB-453 cells were incubated with cetuximab (for A431, for MDA-MB-453) or with 1:25 dilutions of sera from either Asp or iso-Asp p580 immunized Balb/c mice. Cell proliferation was measured by 3H-thymidine incorporation, and growth inhibition calculated as described in the Material and Methods. For ADCC assays, A431 cells (FIG. 9C) or MDA-MB-453 cells (FIG. 9D) were incubated with preimmune or immune serum followed by incubation with human PBMC. ADCC and % cytotoxicity was calculated as described in the Materials and Methods (Example 2, A.(ix)). Rituximab served as a negative control for both cell lines. Trastuzumab and cetuximab served as positive controls for A431 and MDA-MB-453 cells, respectively. , $p<0.05$; *, $p<0.001$; ND, inhibition not detected. Results are representative of three independent experiments.

DETAILED DESCRIPTION

Definitions

Figure 1A:
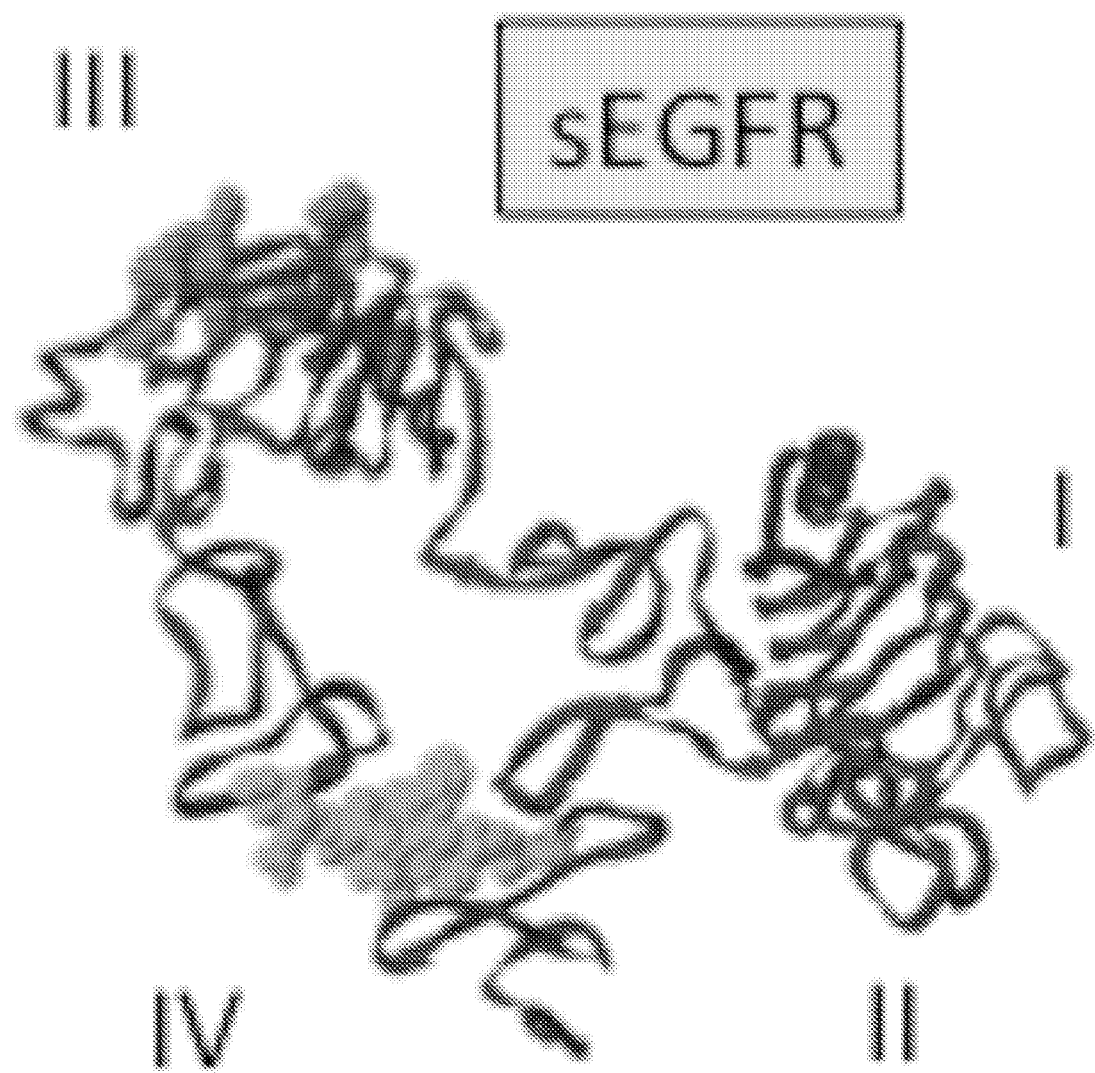
FIG. 1A-FIG. 1D depicts regions corresponding to p580 in EGFR, HER2 and HER3. The regions corresponding to the p580 peptide (green) are shown in the extracellular domain structures of (FIG. 1A) tethered EGFR monomer (PDB ID #1YY9), (FIG. 1B) EGFR dimer (PDB #3NJP), (FIG. 1C) HER3 tethered monomer (PDB #1M6B) and (FIG. 1D) HER2 open monomer (PDB #1N8Z). Also shown are (FIG. 1A) residues bound by cetuximab (fuchsia), (FIG. 1B) bound EGF ligands (gold), (FIG. 1D) residues bound by trastuzumab (red), and residues bound by trastuzumab that overlap with the p580 region (orange).
Figure 1B:
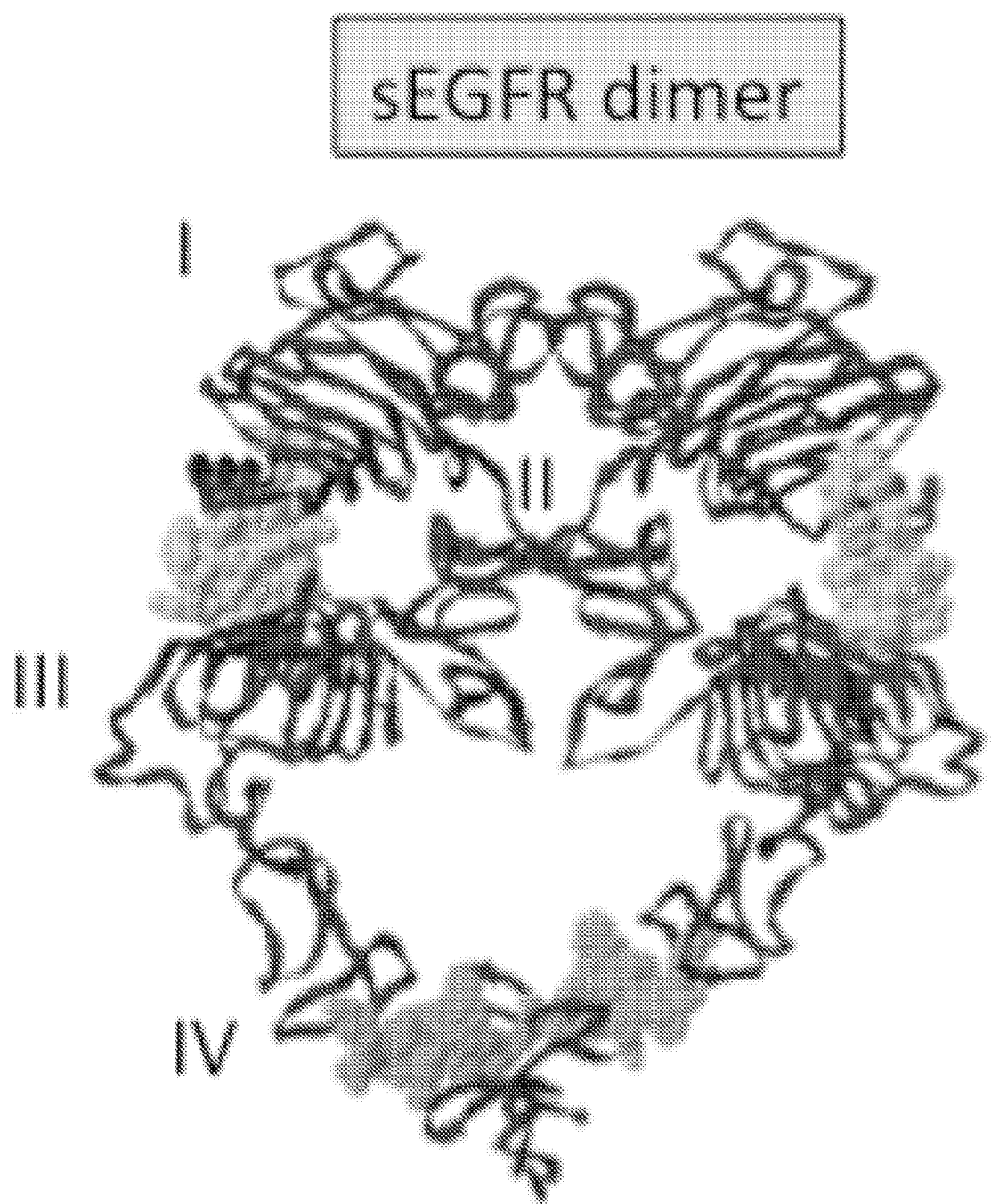
Figure 1C:
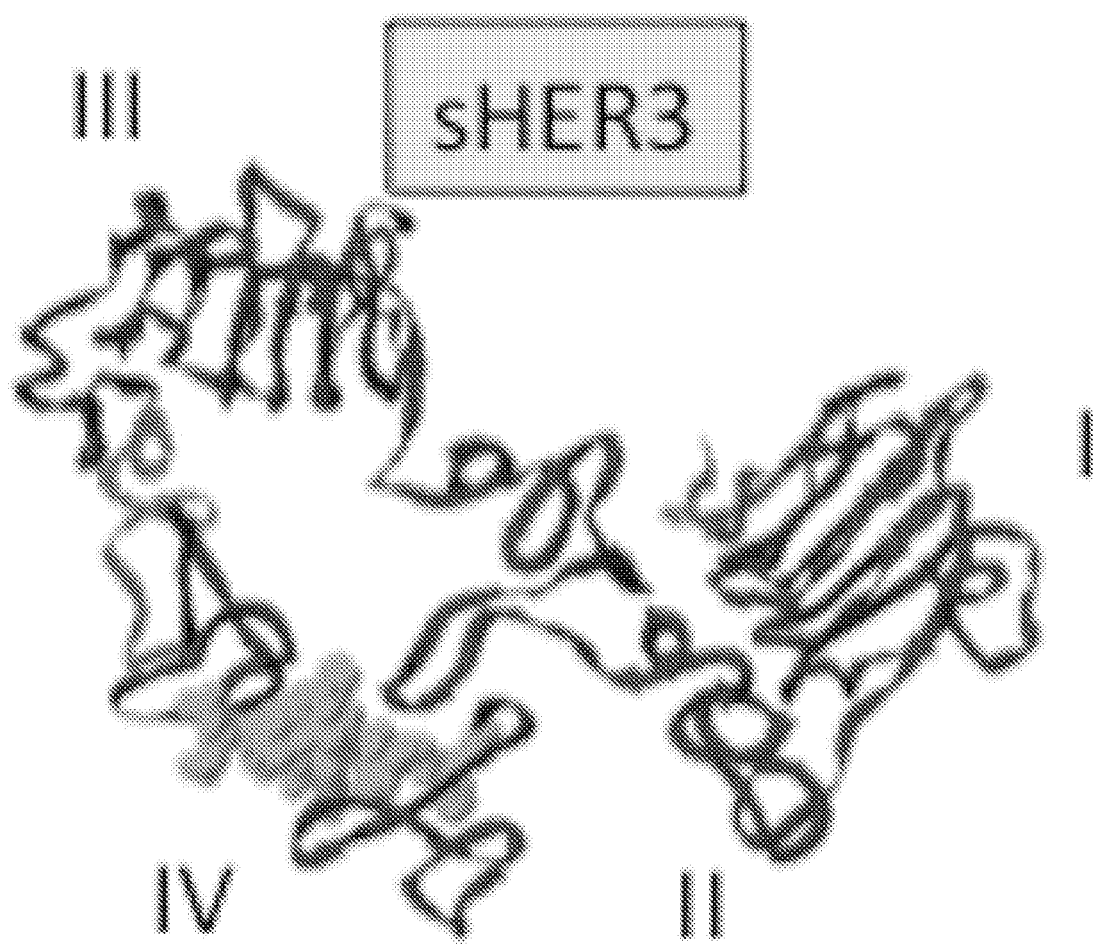
Figure 1D:
Figure 2A:
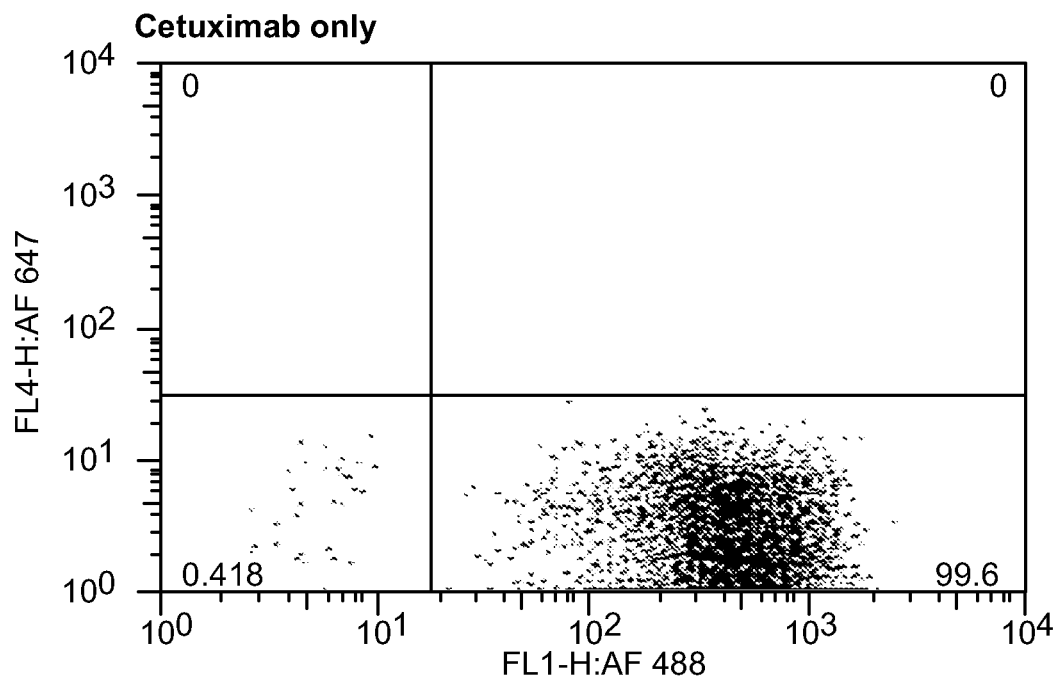
FIG. 2A-FIG. 2D are graphs showing the EGFR p580 mouse immune sera bind to the EGFR overexpressing human A431 tumor cell line at an epitope distinct from that recognized by cetuximab. A431 cells were first incubated with AF-488 conjugated cetuximab, washed then stained with anti-EGFR p580 antisera and AF-647 conjugated secondary antibody. Cells were fixed then analyzed by flow cytometry.
Figure 2B:
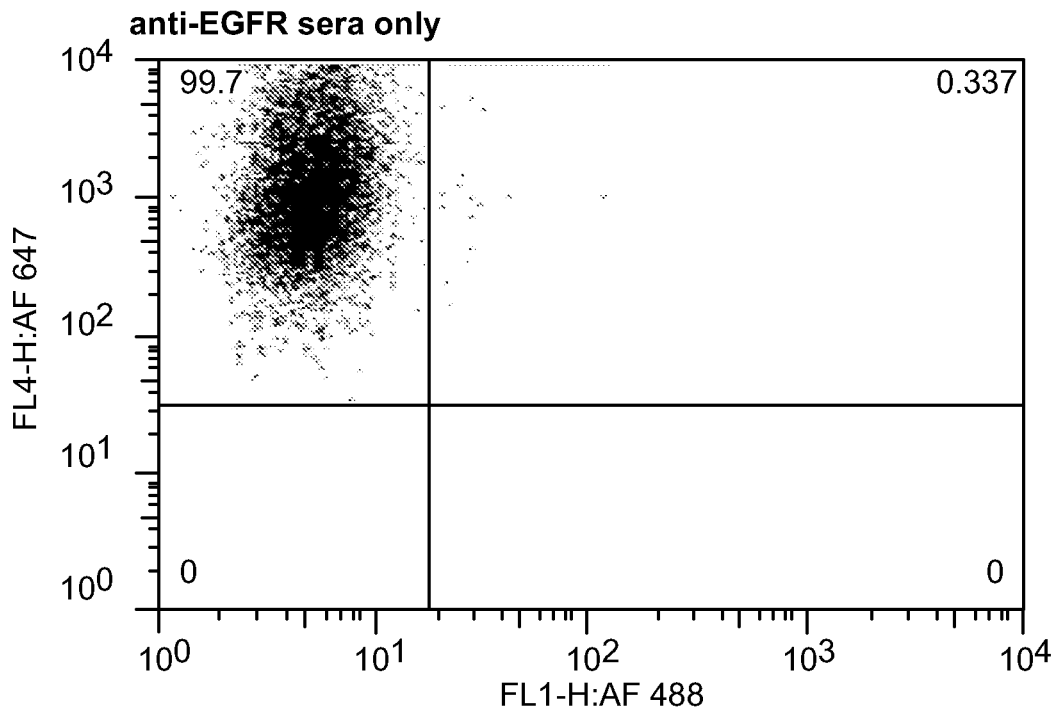
Figure 2C:
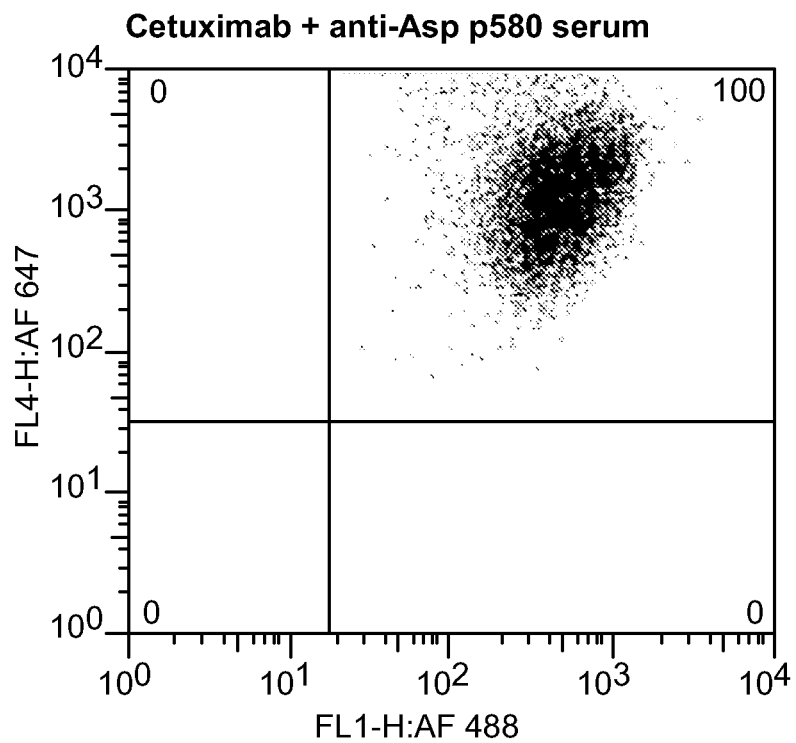
Figure 2D:
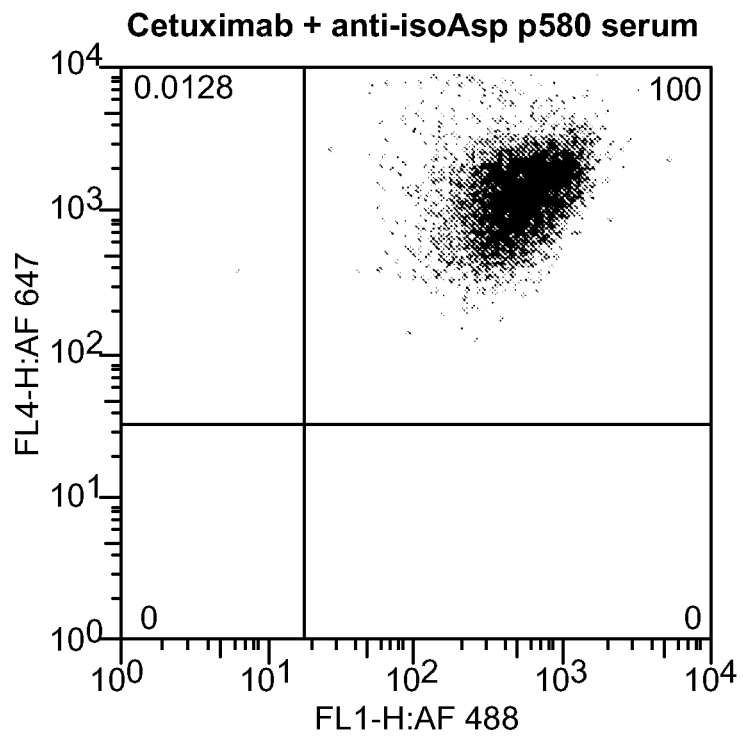

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

As used herein, the term "administering," refers to the placement of a pharmaceutical or vaccine composition as disclosed herein into a subject by a method or route which results in at least partial localization of the compositions at a desired site.

As used herein, an "anticancer agent" may be selected from 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, carboplatin, carmustine, CB1093, chlorambucil, cisplatin, crisnatol, cyclophosphamide, cytarabine, cytosine arabinoside, cytoxan, dacarbazine, dactinomycin, daunorubicin, decarbazine, deferoxamine, demethoxy-hypocrellin A, docetaxel, doxifluridine, doxorubicin, EB1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, taxotere, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, and zorubicin.

As used herein, *Borrelia* spp. refers to, but not limited to, any of the following species: *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mazzottii, Borrelia merionesi, Borrelia microti, Borrelia miyamotoi, Borrelia parkeri, Borrelia persica, Borrelia recurrentis, Borrelia sinica, Borrelia spielmanii, Borrelia tanukii, Borrelia texasensis, Borrelia theileri, Borrelia tillae, Borrelia turcica, Borrelia turdi, Borrelia turicatae, Borrelia valaisiana, Borrelia venezuelensis, Borrelia vincentii, Borrelia burgdorferi* B31, *Borrelia burgdorferi* N40, *Borrelia burgdorferi* JD1, or *Borrelia burgdorferi* 297.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, sarcoma, Sezary syndrome, skin cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, or Wilms tumor.

As used herein, a "chemotherapeutic" agent is selected from the group consisting of a small molecule receptor antagonists such as vatalanib, SU 11248 or AZD-6474, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an epipodophyllotoxin such as etoposide or teniposide, a proteasome inhibitor such as bortezomib or anti-inflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof.

In some embodiments, the chemotherapeutic agent is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy)quinazoline or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin® (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-272 1, a photo-chemically activated drug such as porfimer, photofrin, a benzoporphyrin derivative, a pheophorbide derivative, merocyanin 540 (MC-540) or tin etioporpurin, an anti-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone. Preferred compounds include small molecule VEGF receptor antagonist such as vatalanib (PTK-787/ZK222584), SU-5416, SU-6668, SU-11248, SU-14813, AZD-6474, EGFR/HER2 antagonists such as CI-1033 or GW-2016, an EGFR antagonist such as iressa (gefitinib, ZD-1839), tarceva (erlotinib, OSI-774), PKI-166, EKB-569, HKI-272 or herceptin, an antagonist of the mitogen-activated protein kinase such as BAY-43-9006 or BAY-57-9006, atrasentan, rituximab, cetuximab, Avastin™ (bevacizumab), IMC-1C11, erbitux (C-225), DC-101, EMD-72000, vitaxin, imatinib, an alkylating agent or a platinum compound such as melphalan, cyclophosphamide, cisplatin, carboplatin, oxaliplatin, satraplatin, daunorubicin, doxorubicin (adriamycin), liposomal doxorubicin (doxil), epirubicin, idarubicin, a pyrimidine or purine analogue or antagonist or an inhibitor of the nucleoside diphosphate reductase such as cytarabine, 5-fluorouracile (5-FU), pemetrexed, tegafur/uracil, gemcitabine, capecitabine, mercaptopurine, methotrexate, a vinca alkaloid such as navelbine, vinblastin, vincristin, vindesine or vinorelbine, an antimitotic peptide such as dolastatin, an epipodophyllotoxin or a derivative of podophyllotoxin such as etoposide or teniposide, a non-steroidal inflammatory drug such as meloxicam, celecoxib, rofecoxib, an antibody targeting the surface molecules of cancer cells such as apolizumab or 1D09C3 or the heat shock protein HSP90 modulator geldanamycin and its derivative 17-allylaminogeldanamycin or 17-AAG.

As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially, or repeatedly. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of the invention. Thus, a subject who receives such treatment can benefit from a combined effect of different therapeutic compounds.

The term "functional" when used in conjunction with "equivalent", "analog", "derivative" or "variant" or "fragment" refers to an entity or molecule which possess a biological activity that is substantially similar to a biological activity of the entity or molecule of which it is an equivalent, analog, derivative, variant or fragment thereof.

As used herein, an "immunomodulatory agent" may be selected from aminocaproic acid, azathioprine, bromocriptine, chlorambucil, chloroquine, cyclophosphamide, cyclosporine, cyclosporine A, danazol, dehydroepiandrosterone, dexamethasone, etanercept, hydrocortisone, hydroxychloroquine, infliximab, meloxicam, methotrexate, mycophenylate mofetil, prednisone, sirolimus, and tacrolimus.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "sequence identity or homology" refers to the sequence similarity between two polypeptide molecules. When a position in both of the two compared sequences is occupied by the same base or amino acid monomer subunit, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. Generally, a comparison is made when two sequences are aligned to give maximum homology. Exemplary levels of sequence identity include, but are not limited to, 80, 81, 82, 83, 84, 85, 86, 87, 88, 89, 90, 91, 92, 93, 94, 95, 96, 97, 98, 99% or more sequence identity to a given sequence.

The comparison of sequences and determination of percent homology between two sequences can be accomplished using a mathematical algorithm. The alignment can be performed using the Clustal Method, such as the CLUSTAL-W program. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

For example, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna. CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS*, 4:11-17 (1989)) which has been incorporated into the ALIGN program (version 2.0) (available online), using a PAM120 weight residue table, a gap length penalty of 12 and a gap penalty of 4. Other computer programs which can be used to determine identity between two sequences include, but are not limited to, the suite of Basic Local Alignment Search Tool (BLAST) programs, e.g., BLASTN, BLASTX, and TBLASTX, BLASTP and TBLASTN, publicly accessible and hosted on the internet by the National Center for Biotechnology Information (NCBI).

The term "substantial identity" of amino acid sequences (and of polypeptides having these amino acid sequences) normally means sequence identity of at least 40% compared to a reference sequence (e.g., SEQ ID NOs: 1-15 as set forth infra) as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence (e.g., any one of SEQ ID NO: 1-15). Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

A subject can be one who has been previously diagnosed with or identified as suffering from or having a condition in need of treatment or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "treating" and "preventing" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

A. Compositions-of-Matter

I. ErbB Peptides

The term "ErbB peptide" or "EGFR peptide" as used herein refers to equivalents, homologs, analogs, derivatives, variants or fragments, or biologically active counterparts of the membrane-proximal epitope (p580-598) in the extracellular domain of EGFR. In certain embodiments, the ErbB peptides are functional molecules that possess a biological activity substantially similar to, or under certain conditions, even better than, the wild-type epitope. EGFR (ErbB1) is a 170 kDa cell surface glycoprotein that is overexpressed or mutated in a variety of solid tumors and is associated with more aggressive tumor growth and a poorer prognosis (Sartor C I (2000) *Semin Oncol* 27:15-20; discussion 92-100; Fischer-Colbrie J et al. (1997) *Anticancer Res* 17:613-9; Magne N et al. (2001) *Eur J Cancer* 37:2169-77; Sok J C et al. (2006) *Clin Cancer Res* 12:5064-73; Lu Y et al. (2012) *Cancer Biomark* 11:219-26; Milella M et al. (2012) *J Thorac Oncol* 7:672-80; da Cunha Santos G et al. (2011) *Annu Rev Pathol* 6:49-69). It is a member of the ErbB family of receptor tyrosine kinases and forms homodimers and heterodimers with other members of the ErbB family (HER2/ErbB2, HER3/ErbB3, HER4/ErbB4) that result in downstream signaling (Roskoski R, (2014) *Jr Pharmacol Res* 79:34-74). In certain embodiments, the ErbB peptides can be from any source, e.g., rat, mouse, guinea pig, dog, cat, rabbit, pig, cow, horse, goat, donkey or human. In certain embodiments, the ErbB peptides can be the Asp or iso-Asp isoforms. In another embodiment, the peptides can cyclized to constrain the peptide in its native conformation.

ErbB peptides can have the amino sequences set forth in the following sequences. (see also Tables 1, 2, and 4)

```
Human p580-598
                                    (SEQ ID NO: 1)
IQCAHYIDGPHCVKTCPAG;

Mouse p580-598
                            (same as (SEQ ID NO: 1))
IQCAHYIDGPHCVKTCPAG;

hu HER2 p585-603,
                                    (SEQ ID NO: 2)
VACAHYKDPPFCVARCPSG;

hu HER3 p574-592,
                                    (SEQ ID NO: 3)
AQCAHFRDGPHCVSSCPHG;

hu HER4 p578-596,
                                    (SEQ ID NO: 4)
TKCSHFKDGPNCVEKCPDG;

mu/hu p566-584,
                                    (SEQ ID NO: 5)
AMNITCTGRGPDNCIQCAH;

Ac-IQCAHYIDGPHCVKTSPAG-amide (bolded, underlined
text only, SEQ ID NO. 6);

KLH-AoaIQCAHYIDGPHCVKTSPAG-amide (bolded, underlined text only, SEQ ID NO. 7), where "KLH" is a keyhole limpet hemocyanin and Aoa is a spacer;

Ac-IQCAHYIDGPHCVKTSPAG(KAoa)(-amide)-KLH (bolded, underlined text only, SEQ ID NO. 8), where "KLH"

is a keyhole limpet hemocyanin and Aoa is a spacer;

KLH-AoaIQCAHYIDPPHCVKTSPAG-amide (bolded, underlined text only, SEQ ID NO. 9), where "KLH" is a keyhole limpet hemocyanin and Aoa is a spacer;

KLH-AoaIQCAHYIDGPHCVKTSPAG-amide (bolded, underlined text only, SEQ ID NO. 10), where "KLH"

is a keyhole limpet hemocyanin and Aoa is a spacer;

mu/hu p572-590,
                                    (SEQ ID NO: 11)
TGRGPDNCIQCAHYIDGPH;

mu p596-615,
                                    (SEQ ID NO: 12)
PAGIMGENNTLVWKYADANN;

hu p596-615,
                                    (SEQ ID NO: 13)
PAGVMGENNTLVWKYADAGH;

mu p605-623,
                                    (SEQ ID NO: 14)
TLVWKYADANNVCHLCHAN;
and Canine p553-571
                                    (SEQ ID NO: 15)
IKCAHYIDGPHCVKTCPAG (also referred herein as
"p553").
```

The ErbB peptides of the present invention may be modified to include conservative amino acid substitutions, in accordance with standard techniques. Isolated ErbB peptides may comprise, for example, the amino acid sequences of SEQ ID NOs: 1-15, or modified forms, or combinations thereof. The isolated ErbB peptides of the present invention may include polypeptides having at least, but not more than 4, 3, 2, or 1 amino acid that differs from SEQ ID NOs: 1-15. The isolated ErbB peptides may comprise polypeptides having at least 80%, 85%, 86%, 87%, 88%, 89%, 90%, 91%, 92%, 93%, 94%, 95%, 96%, 97%, 98%, or 99% sequence identity with a ErbB peptide having the amino acid sequence of SEQ ID NOs: 1-15.

The ErbB peptide may be isolated from a EGFR receptor, or synthesized chemically, or ribosomally in a cell free system, or ribosomally within a cell. Chemical synthesis of peptides may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Merrifield et al. (1964) *J. Am. Chem. Soc.*, (85):2149, Houghten et al. (1985) *Proc. Natl. Acad. Sci. USA* (82):5132, and by Stewart and Young in *Solid Phase Peptide Synthesis*, Pierce Chem. Co, Rockford, Ill. (1984). Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., *Curr. Opin. Biotech.* (1993): vol. 4, p 420; M. Miller, et al., *Science* (1989): vol. 246, p 1149; A. Wlodawer, et al., *Science* (1989): vol. 245, p 616; L. H. Huang, et al., *Biochemistry* (1991): vol. 30, p 7402; M. Schnolzer, et al., *Int. J. Pept. Prot. Res.* (1992): vol. 40, p 180-193; K. Rajarathnam, et al., *Science* (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., *J. Biol. Chem.* (1992): vol. 267, p 3852; L. Abrahmsen, et al., *Biochemistry* (1991): vol. 30, p 4151; T. K. Chang, et al., *Proc. Natl. Acad. Sci. USA* (1994) 91: 12544-12548; M. Schnlzer, et al., *Science* (1992): vol., 3256, p 221; and K. Akaji, et al., *Chem. Pharm. Bull.* (Tokyo) (1985) 33: 184).

ErbB peptides may be achieved using in vitro translation systems. An in vitro translation systems is, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, e1F3, the cap-binding (CB) complex, comprising the cap-binding protein (CBP) and eukaryotic initiation factor 4F (e1F4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes.

ErbB peptides may be chemically modified based on linkage to a water soluble polymer and capture reagent. The polymer may have a single reactive group, such as an active ester for acylation or an aldehyde for alkylation, so that the degree of polymerization may be controlled. The water soluble polymer, or mixture thereof if desired, may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. The binding reagent may be selected from the group consisting of biotin and avidin, carbohydrates and lectins, complementary nucleotide sequences, complementary peptide sequences, effector and receptor molecules, enzyme cofactors and enzymes, and enzyme inhibitors and enzymes.

The ErbB peptides may be chemically modified or conjugated to carrier proteins (e.g., keyhole limpet hemocyanin (KLH), bovine serum albumin (BSA), ovalbumin (OVA)) to facilitate immunization. See for example, Table 2. The foregoing ErbB peptides may be chemically modified and adapted with other polymers and/or capture reagents using no more than routine experimentation.

II. Pharmaceutical and Vaccine Compositions

The pharmaceutical and vaccine compositions and methods of the present invention may be utilized to treat an individual in need thereof. Such pharmaceutical and vaccine compositions can be useful for prophylactic and/or therapeutic treatment of cancers. In certain embodiments, the individual is a mammal such as a human, or a non-human mammal such as a dog. When administered to a mammal, the ErbB peptides are combined or formulated with an adjuvant (e.g., *Borrelia* antigen, receptor agonist, or immunomodulatory agent, or combinations thereof) and administered as a pharmaceutical and vaccine compositions. Such pharmaceutical and vaccine compositions are administered (individually or in combination) comprising, for example, the pharmaceutical and vaccine compositions, and anti-cancer agent, chemotherapeutic agent, or anti-PD therapy.

*Borrelia* antigens for use as adjuvants may include, but not limited to, LymeVax or Nobivac Lyme, or LYMErix, or combinations thereof. Receptor agonist for use as adjuvants may include, but are not limited to, CpG oligodeoxynucleotides 7909 (CpG 7909), Monophosphoryl lipid A (MPL), lipopolysaccharide (LPS), polyI:C, and R848. Immunomodulatory agents for use as adjuvants may include, but are not limited to, complete Freunds adjuvant (CFA), incomplete Freunds adjuvant (IFA), LTK63, dimethyl dioctadecyl-ammonium bromide (DDA), lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, water-in-oil emulsion, mannide monooleate, vegetable grade (VG) oleic acid, Montanide ISA-51 VG, ISA-720, microparticles, immuno stimulatory complexes, liposomes, virosomes, virus-like particles, cholera toxin, heat-labile toxin from *E. coli*, lipoproteins, dendritic cells, IL-12, GM-CSF, nanoparticles, a combination of soybean oil, emulsifying agents, and ethanol to form a nanoemulsion, AS04, and ZADAXIN, or combinations thereofying agents, and ethanol to form a nanoemulsion; AS04, ZADAXIN, or combinations thereof.

When formulating the pharmaceutical and vaccine compositions, the ErbB peptides may dissolved or resuspended in any suitable physiologically compatible carrier. As used herein, "physiologically compatible carrier" refers to a physiologically acceptable diluent including, but not limited to water, phosphate buffered saline (PBS), or saline, and, in some embodiments, includes another adjuvant. For injection, the presently pharmaceutical and vaccine compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of pharmaceutical and vaccine compositions include fatty oils, such as sesame oil, or synthetic fatty acid esters, such as ethyl oleate or triglycerides, or liposomes. Optionally, the suspension also can contain suitable stabilizers or agents that increase the solubility of the compositions.

In addition, the pharmaceutical and vaccine compositions may be combined with pharmaceutically acceptable carriers. Pharmaceutically acceptable carriers are well known in the art and include, for example, aqueous solutions such as water or physiologically buffered saline, or other solvents or vehicles such as glycols, glycerol, oils such as olive oil, or injectable organic esters. In preferred embodiments, when such pharmaceutical and vaccine compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical and vaccine compositions can be in dosage unit form such as tablet, capsule (including sprinkle capsule and gelatin capsule), granule, lyophile for reconstitution, powder, solution, syrup, suppository, injection or the like. The pharmaceutical and vaccine compositions can also be present in a transdermal delivery system, e.g., a skin patch. The compositions can also be present in a solution suitable for topical administration, such as an eye drop.

A pharmaceutically acceptable carrier can contain physiologically acceptable agents that act, for example, to stabilize, increase solubility or to increase the absorption of a composition. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical and vaccine compositions can be a self-emulsifying drug delivery system or a selfmicroemulsifying drug delivery system. The pharmaceutical and vaccine compositions (preparation) also can be a liposome or other polymer matrix, which can have incorporated therein, for example, the pharmaceutical and vaccine compositions of the present invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The presently disclosed pharmaceutical and vaccine compositions can be manufactured in a manner known in the art, e.g. by means of conventional mixing, dissolving, granulating, dragee-making, levitating, emulsifying, encapsulating, entrapping or lyophilizing processes.

A pharmaceutical and vaccine composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The composition may also be formulated for inhalation. In certain embodiments, a composition may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

Pharmaceutical and vaccine compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

Certain embodiments of the invention provide for combination therapies. These additional agents may be administered separately, as part of a multiple dosage regimen, or they may be part of a single dosage form in a single composition.

By "in combination with" is meant the administration of the pharmaceutical and vaccine compositions, with one or more therapeutic agents (e.g., anti-cancer agent, chemotherapeutic agent, and/or anti-PD therapy) either simultaneously, sequentially, or a combination thereof. Therefore, a subject administered a combination of a pharmaceutical or and vaccine composition of the present invention and/or therapeutic agents, can receive the pharmaceutical or vaccine composition, as described herein, and one or more therapeutic agents at the same time (i.e., simultaneously) or at different times (i.e., sequentially, in either order, on the same day or on different days), so long as the effect of the combination of both agents is achieved in the subject.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the composition which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active composition, such as the ErbB peptides and adjuvant and, optionally, one or more accessory ingredients. In general, the formulations are prepared by uniformly and intimately bringing into association the ErbB peptides and adjuvant, with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the ErbB peptide and adjuvant. Compositions may also be administered as a bolus, electuary or paste.

Pharmaceutical and vaccine compositions suitable for oral administration include push-fit capsules made of gelatin, as well as soft, sealed capsules made of gelatin and a coating, e.g., a plasticizer, such as glycerol or sorbitol. The push-fit capsules can contain active ingredients admixed with a filler or binder, such as lactose or starches, lubricants, such as talc or magnesium stearate, and, optionally, stabilizers. In soft capsules, the pharmaceutical or vaccine composition can be dissolved or suspended in suitable liquids, such as fatty oils, liquid paraffin, or liquid polyethylene glycols (PEGs), with or without stabilizers. Stabilizers can be added as warranted.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical and vaccine compositions may also comprise buffering agents. Solid compositions of a similar type may also be employed as fillers in soft and hard-filled gelatin capsules using such excipients as lactose or milk sugars, as well as high molecular weight polyethylene glycols and the like.

Dragee cores are provided with suitable coatings, such as concentrated sugar solutions, which also can contain gum arabic, talc, polyvinylpyrrolidone, carbopol gel, polyethylene glycol (PEG), and/or titanium dioxide, lacquer solutions, and suitable organic solvents or solvent mixtures. Dyestuffs or pigments can be added to the tablets or dragee coatings for product identification or to characterize the quantity of pharmaceutical and vaccine compositions, e.g., dosage, or different combinations of doses.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical and vaccine compositions, such as dragees, capsules (including sprinkle capsules and gelatin capsules), pills and granules, may optionally be scored or prepared with coatings and shells, such as enteric coatings and other coatings well known in the pharmaceutical-formulating art. In some embodiments, the pharmaceutical and vaccine compositions, may be employed in combination with one or more carriers to allow more stability, different releasing properties in vivo, targeting to a specific site, or any other desired characteristic that will allow more effective delivery of the pharmaceutical and vaccine compositions, to a subject or a target in a subject. They may be formulated so as to provide slow or controlled release of the active ingredient therein using, for example, hydroxypropylmethyl cellulose in varying proportions to provide the desired release profile, other polymer matrices, liposomes, nanoparticles, microspheres, microbubbles, and/or other suitable carriers. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical and vaccine compositions for rectal, vaginal, or urethral administration may be presented as a suppository, which may be prepared by mixing one or more active compositions with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active composition.

Formulations of the pharmaceutical and vaccine compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active composition may be mixed under sterile conditions with a pharmaceutically acceptable carrier, and with any preservatives, buffers, or propellants that may be required.

The ointments, pastes, creams and gels may contain, in addition to an active composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a composition to the body. Such dosage forms can be made by dissolving or dispersing the active composition in the proper medium. Absorption enhancers can also be used to increase the flux of the composition across the skin. The rate of such flux can be controlled by either providing a rate controlling membrane or dispersing the composition in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

The phrases "parenteral administration" and "administered parenterally" as used herein means modes of administration other than enteral and topical administration, usually by injection, and includes, without limitation, intravenous, intramuscular, intraarterial, intrathecal, intraocular, intraarterial, intralesional, intracapsular, intraorbital, intracardiac, intradermal, intraperitoneal, transtracheal, subcutaneous, subcuticular, intraarticular, subcapsular, subarachnoid, intraspinal and intrasternal injection and infusion. Compositions suitable for parenteral administration comprise the pharmaceutical and vaccine compositions of the present invention, in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical and vaccine compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compositions in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compositions can be given per se or as a pharmaceutical or vaccine composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a composition at a particular target site. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., *Biopolymers* 22:547, 1983), poly (2-hydroxyethyl-methacrylate) (Langer et al., *J. Biomed. Mater. Res.* 15:167, 1981; *Langer, Chem. Tech.* 12:98, 1982), ethylene vinyl acetate (Langer et al., Id), or poly-D-(–)-3-hydroxybutyric acid (EP 133,988A).

Actual dosage levels of the active ingredients in the pharmaceutical and vaccine compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular composition or combination of compositions employed, or the ester, salt or amide thereof, the route of administration, the time of administration, the rate of excretion of the particular composition(s) being employed, the duration of the treatment, other drugs, compostions and/or materials used in combination with the particular composition(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical or vaccine composition required. For example, the physician or veterinarian could start doses of the pharmaceutical or vaccine composition at levels lower than that required in order to achieve the desired therapeutic effect and gradually increase the dosage until the desired effect is achieved. By "therapeutically effective amount" is meant the concentration of a pharmaceutical or vaccine composition, that is sufficient to elicit the desired therapeutic effect. It is generally understood that the effective amount of the composition will vary according to the weight, sex, age, and medical history of the subject. Other factors which influence the effective amount may include, but are not limited to, the severity of the patient's condition, the disorder being treated, the stability of the composition, and, if desired, another type of therapeutic agent being administered with the compositions. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active composition used in the methods of the invention will be that amount of the composition that is the lowest dose effective to produce a therapeutic effect. Such an effective dose will generally depend upon the factors described above.

If desired, the effective daily dose of the active composition may be administered as one, two, three, four, five, six or more sub-doses administered separately at appropriate intervals throughout the day, optionally, in unit dosage forms. In certain embodiments of the present invention, the active composition may be administered two or three times daily. In preferred embodiments, the active composition will be administered once daily.

The patient receiving this treatment may be any animal in need, including primates, in particular humans, and other mammals such as dogs, equines, cattle, swine and sheep; and poultry and pets in general.

In certain embodiments, the pharmaceutical or vaccine composition, may be conjointly administered with another type of therapeutic agent (anti-cancer agent, chemotherapeutic agent, or anti-PD therapy).

This invention includes the use of pharmaceutically acceptable salts of the pharmaceutical and vaccine compositions, and methods of the present invention. The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

As used herein, the term "pharmaceutically acceptable carrier or excipient" refers to a carrier medium or an excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, "Remington's Pharmaceutical Sciences", E. W. Martin, 18th Ed., 1990, Mack Publishing Co.: Easton, Pa., which is incorporated herein by reference in its entirety).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight polypeptides (less than about 10 residues); proteins, such as albumin, gelatin or immunoglobulins; hydrophilic polymers, such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. Other suitable excipients include, but are not limited to, carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethyl cellulose; and gums including arabic and tragacanth; and proteins, such as gelatin and collagen; and polyvinylpyrrolidone (PVP:povidone). If desired, disintegrating or solubilizing agents, such as cross-linked polyvinyl pyrrolidone, agar, alginic acid, or a salt thereof, such as sodium alginate, also can be added to the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

B. Therapeutic Methods

The present invention further provides novel therapeutic methods of preventing, delaying, reducing, and/or treating a cancer, including a cancerous tumor. In one embodiment, a method for preventing or treating cancer in a subject, the method comprising administering to a subject (e.g., a subject in need thereof), the pharmaceutical or vaccine composition of the present invention (e.g., comprising a peptide having at least 85% identity to an amino acid sequence selected from the group consisting of SEQ ID: NOs: 1-15, or combinations thereof, and an adjuvant). A subject in need thereof may include, for example, a subject who has been diagnosed with a tumor, including a pre-cancerous tumor, a cancer, or a subject who has been treated, including subjects that have been refractory to the previous treatment.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical or vaccine composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The pharmaceutical compositions described herein may be delivered by any suitable route of administration, including orally, nasally, transmucosally, ocularly, rectally, intravaginally, parenterally, including intramuscular, subcutaneous, intramedullary injections, as well as intrathecal, direct intraventricular, intravenous, intraarticular, intra-sternal, intra-synovial, intra-hepatic, intralesional, intracranial, intraperitoneal, intranasal, or intraocular injections, intra-isternally, topically, as by powders, ointments or drops (including eyedrops), including buccally and sublingually, transdermally, through an inhalation spray, or other modes of delivery known in the art.

The terms "systemic administration," "administered systemically," "peripheral administration," and "administered peripherally" as used herein mean the administration of the pharmaceutical composition such that it enters the patient's system and, thus, is subject to metabolism and other like processes.

The terms "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In certain embodiments the pharmaceutical and vaccine compositions are delivered generally (e.g., via oral or parenteral administration). In certain other embodiments the pharmaceutical and vaccine compositions are delivered locally through direct injection into a tumor or direct injection into the tumor's blood supply (e.g., arterial or venous blood supply). In some embodiments, the pharmaceutical and vaccine compositions are delivered by both a general and a local administration. For example, a subject with a tumor may be treated through direct injection of a composition containing a composition described herein into the tumor or the tumor's blood supply in combination with oral administration of a pharmaceutical or vaccine composition of the present invention. If both local and general administration is used, local administration can occur before, concurrently with and/or after general administration.

In certain embodiments, the methods of treatment of the present invention, including treating a cancerous or pre-cancerous tumor comprise administering compositions described herein in combination with a second agent and/or therapy to the subject. By "in combination with" is meant the administration of the pharmaceutical and vaccine compositions as described above, with one or more therapeutic agents (e.g., anti-cancer agent, chemotherapeutic agent, and/or anti-PD therapy) either simultaneously, sequentially, or a combination thereof. Therefore, a subject administered a combination of one or more pharmaceutical and vaccine compositions, and/or one or more therapeutic agents, can receive the pharmaceutical or vaccine composition as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 minutes, or longer of one another. In other embodiments, agents administered sequentially, can be administered within 1, 5, 10, 15, 20 or more days of one another.

In various embodiments, the pharmaceutical and vaccine compositions of the present invention and one or more therapeutic agents (e.g., anti-cancer agent, chemotherapeutic agent, and/or anti-PD therapy), are administered concomitantly, concurrently or sequentially. In various embodiments, the pharmaceutical or vaccine composition is administered before, during or after administering the one or more therapeutic agents. As a non-limiting example, the pharmaceutical or vaccine composition may be administered, for example, daily at the aforementioned dosages, and the one or more therapeutic agents may be administered, for example, daily, weekly, biweekly, every fortnight and/or monthly at the aforementioned dosages. As another non-limiting example, the pharmaceutical or vaccine composition may be administered, for example, daily, weekly, biweekly, every fortnight and/or monthly, at the aforementioned dosages, and the one or more therapeutic agents, may be administered, for example, daily at the aforementioned dosages. Further, each of the pharmaceutical or vaccine composition and one or more therapeutic agents, may be administered daily, weekly, biweekly, every fortnight and/or monthly, wherein the pharmaceutical or vaccine composition is administered at the aforementioned dosages on a day different than the day on which the one or more therapeutic agents, is administered at the aforementioned dosages.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

Such methods in certain embodiments comprise administering pharmaceutical and vaccine compositions comprising pharmaceutical or vaccine compositions described herein in conjunction with one or more chemotherapeutic agents and/or scavenger compounds, including chemotherapeutic agents described herein, as well as other agents known in the art. Conjunctive therapy includes sequential, simultaneous and separate, or co-administration of the pharmaceutical or vaccine composition in a way that the therapeutic effects of the one or more pharmaceutical and vaccine compositions as described above, with one or more therapeutic agents (e.g., anti-cancer agent, chemotherapeutic agent, and/or anti-PD therapy), administered have not entirely disappeared when the subsequent compound is administered. In one embodiment, the second agent is a chemotherapeutic agent. In another embodiment, the second agent is a scavenger compound. In another embodiment, the second agent is radiation therapy. In a further embodiment, radiation therapy may be administered in addition to the pharmaceutical or vaccine composition. In certain embodiments, the second agent may be co-formulated in the separate pharmaceutical or vaccine composition.

In some embodiments, the subject pharmaceutical and vaccine compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the pharmaceutical and vaccine compositions as described above, per kg body weight of the subject. For example, a range of amounts of compositions or compound encapsulated therein are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the pharmaceutical and vaccine composition as described above, will generally be in the range of about 0.4 mg to about 40 mg per kg body weight, specifically in the range of about 5 mg to about 20 mg per kg, and more specifically in the range of about 10 mg to about 20 mg per kg. In one embodiment, the dosage is in the range of about 15 mg to about 25 mg per kg. In another embodiment, the dosage is about 4 mg per kg.

In some embodiments the molar concentration of the pharmaceutical or vaccine composition as described above, in a pharmaceutical or vaccine composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the pharmaceutical composition as described above, will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Actual dosage levels of the active ingredients in the pharmaceutical and vaccine compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular therapeutic agent in the formulation employed, or the ester, salt or amide thereof, the route of administration, the time of administration, the rate of excretion or metabolism of the particular therapeutic agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical or vaccine composition required. For example, the physician or veterinarian could prescribe and/or administer doses of the pharmaceutical or vaccine composition of the invention employed in the pharmaceutical or vaccine composition at levels lower than that required in order to achieve the desired therapeutic effect and gradually increase the dosage until the desired effect is achieved.

In general, a suitable daily dose of a pharmaceutical or vaccine composition of the invention will be that amount of the pharmaceutical or vaccine composition which is the lowest dose effective to produce a therapeutic effect. Such an effective dose will generally depend upon the factors described above.

If desired, the effective daily dose of the pharmaceutical or vaccine composition may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

Additional dosages of an effective amount of the pharmaceutical or vaccine composition or one or more therapeutic agents, can be in the ranges recommended by the manufacturer where known therapeutic compositions are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the pharmaceutical or vaccine composition or one or more therapeutic agents or one or more therapeutic agents, may be administered once a day (SID/QD), twice a day (BID), three times a day (TID), four times a day (QID), or more, so as to administer an effective amount of the pharmaceutical composition or one or more therapeutic agents or one or more therapeutic agents, to the subject, where the effective amount is any one or more of the doses described herein.

In some embodiments, the pharmaceutical or vaccine composition is administered at about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, or 20 to 40 mg/kg. In some embodiments, the pharmaceutical or vaccine composition comprises a minimum of two doses, administered 2-4 weeks apart. Additional booster vaccinations could be provided at intervals thereafter and in subsequent years of treatment. Here, "mg/kg" refers to mg per kg body weight of the subject. In certain embodiments, the pharmaceutical or vaccine composition is administered to a human.

In some embodiments, the effective amount of the therapeutic agent is any one or more of about 0.01 to 0.05 µg/kg/day, 0.05-0.1 µg/kg/day, 0.1 to 0.5 µg/kg/day, 0.5 to 5 µg/kg/day, 5 to 10 µg/kg/day, 10 to 20 µg/kg/day, 20 to 50 µg/kg/day, 50 to 100 µg/kg/day, 100 to 150 µg/kg/day, 150 to 200 µg/kg/day, 200 to 250 µg/kg/day, 250 to 300 µg/kg/day, 300 to 350 µg/kg/day, 350 to 400 µg/kg/day, 400 to 500 µg/kg/day, 500 to 600 µg/kg/day, 600 to 700 µg/kg/day, 700 to 800 µg/kg/day, 800 to 900 µg/kg/day, 900 to 1000 µg/kg/day, 0.01 to 0.05 mg/kg/day, 0.05-0.1 mg/kg/day, 0.1 to 0.5 mg/kg/day, 0.5 to 1 mg/kg/day, 1 to 5 mg/kg/day, 5 to 10 mg/kg/day, 10 to 15 mg/kg/day, to 20 mg/kg/day, 20 to 50 mg/kg/day, 50 to 100 mg/kg/day, 100 to 200 mg/kg/day, 200 to 300 mg/kg/day, 300 to 400 mg/kg/day, 400 to 500 mg/kg/day, 500 to 600 mg/kg/day, 600 to 700 mg/kg/day, 700 to 800 mg/kg/day, 800 to 900 mg/kg/day, 900 to 1000 mg/kg/day or a combination thereof. Here, "µg/kg/day" or "mg/kg/day" refers to pg or mg per kg body weight of the subject per day.

In some embodiments, the one or more therapeutic agents is administered at about 0.01 to 0.1 mcg/kg, 0.1 to 0.5 mcg/kg, 0.5 to 5 mcg/kg, 5 to 10 mcg/kg, 10 to 20 mcg/kg, 20 to 50 mcg/kg, 50 to 100 mcg/kg, 100 to 200 mcg/kg, 200 to 300 mcg/kg, 300 to 400 mcg/kg, 400 to 500 mcg/kg, 500 to 600 mcg/kg, 600 to 700 mcg/kg, 700 to 800 mcg/kg, 800 to 900 mcg/kg, or 900 to 1000 mcg/kg. In some embodiments, the one or more therapeutic agents is administered 1-3 times per day or 1-7 times per week. Still in some embodiments, the one or more therapeutic agents is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mcg/kg" refers to mcg per kg body weight of the subject. In certain embodiments the one or more therapeutic agents is administered to a human.

In accordance with the invention, the pharmaceutical or vaccine composition or one or more therapeutic agents or one or more therapeutic agents, may be administered using the appropriate modes of administration, for instance, the modes of administration recommended by the manufacturer for each of the pharmaceutical or vaccine composition or one or more therapeutic agents or one or more therapeutic agents. In accordance with the invention, various routes may be utilized to administer the pharmaceutical or vaccine composition or one or more therapeutic agents or one or more therapeutic agents, of the claimed methods, including but not limited to aerosol, nasal, oral, transmucosal, transdermal, parenteral, implantable pump, continuous infusion, topical application, capsules and/or injections. In various embodiments, the pharmaceutical or vaccine composition or one or more therapeutic agents or one or more therapeutic agents, are administered intravenously, intracerebrally, intramuscularly, subcutaneously, intraperitoneally, orally or via inhalation. The pharmaceutical or vaccine composition or one or more therapeutic agents may be administered via the same or separate routes.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

As described above, the pharmaceutical or vaccine composition as described above, may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 mins., wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may be given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods of administering radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant.

In contrast, radiopharmaceuticals are unsealed sources of radiation that may be given orally, intravenously or directly into a body cavity.

Radiation therapy may also include stereotactic surgery or stereotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject pharmaceutical or vaccine composition may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the pharmaceutical or vaccine composition as described above, described herein relative to the control. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the pharmaceutical or vaccine composition as described above, relative to control. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for pharmaceutical or vaccine composition as described herein relative to control. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ as determined in cell culture. Such information may be used to more accurately determine useful doses in humans. Levels in plasma may be measured, for example, by high performance liquid chromatography.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of cancer cell growth in an assay.

In any of the above-described methods, the administering of the pharmaceutical or vaccine composition as described above, can result in at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy in a subject, compared to the solid malignancy before administration of the pharmaceutical and vaccine compositions.

In some embodiments, the therapeutically effective amount of the vaccine composition of the present invention is administered prophylactically to prevent a solid malignancy from forming in the subject.

In some embodiments, the subject is human. In other embodiments, the subject is non-human, such as a dog.

The invention now being generally described, it will be more readily understood by reference to the following examples which are included merely for purposes of illustration of certain aspects and embodiments of the present invention, and are not intended to limit the invention.

EXEMPLIFICATIONS

Example 1: EGFR p580 Generated Strong Anti-EGFR Antibody Responses and Inhibited Tumor Cell Growth As described in the following examples, mice immunized with a membrane-proximal epitope (p580-598) in the extracellular domain of EGFR generated strong anti-EGFR antibody responses that inhibit in vitro growth of EGFR+ human A431 cells. More importantly, EGFR p580 immune serum was found to bind homologous HER2 and HER3 epitopes, suggesting that vaccination with EGFR p580 induces antibodies that are cross-reactive with other members of the ErbB family, such as EGFR, HER2 and HER3. Structural studies indicate the antibodies induced by EGFR p580 will also cross react with EGFRvIII, a mutant ErbB family member, which is targeted by Rindopepimut, a 13-amino acid EGFRvIII-specific peptide conjugated to KLH (Babu R et al. (2012) Core Evid 7: 93-103).

Our laboratory has demonstrated that the introduction of posttranslational modifications, specifically the conversion of an aspartic acid into an isoaspartic acid (isoAsp), often breaks immune tolerance to self-peptides as well as tumor antigens (Doyle et al. (2006) J Biol Chem 281:32676-83; Mamula M J et al. (1999) J. Biol. Chem 274:22321-7.

Our subsequent HER2 and EGFR peptide vaccination experiments identified unmodified peptides that can break immune tolerance in mice. These peptides presumably represent cryptic epitopes that are not normally processed and presented by the immune system. Mice immunized with Asp and isoAsp isoforms of the EGFR peptide p580-598 developed anti-peptide antibodies that recognize native human EGFR, as well as inhibit tumor cell growth and promote ADCC tumor cell killing. These antibodies also recognize other members of the ErbB family, in particular HER2 and HER3, and inhibit growth of HER2+ tumor cells. More importantly, these antibodies are also capable of inhibiting the growth of HER2 positive, EGFR negative tumor cells. Thus, this immunization strategy could be used to develop a therapeutic cancer vaccine to target multiple proteins of ErbB family expressed on the same tumor. The appeal of this immunization strategy is that the resulting antibodies have specificity for homologous regions of both HER2 and HER3 in addition to EGFR.

The EGFR p580 peptide shares sequence homology with amino acids 585-603 in HER2 and amino acids 574-592 in HER3 (Table 1). Various tumors, including colorectal and breast cancer, express EGFR and another member of the ErbB family, i.e., HER2 and/or HER3 (Rowinsky E K (2004) Annu Rev Med 55: 433-57; Beji A et al. (2012) Clin Cancer Res 18: 956-68).

Antibodies elicited by the chemically synthesized EGFR p580 peptide, IQCAHYIDGPHCVKTCPAG (SEQ ID NO. 1), bind homologous epitopes from EGFR, HER2 and HER3. These antibodies cross react with HER2 and inhibit the growth of EGFR-negative, HER2-positive tumor cells. The p580 peptide sequence can be modified to mimic any or all of the corresponding homologous epitopes in EGFR, HER2, HER3 and HER4

TABLE 1

Sequences of human ErbB family members that correspond to EGFR p580. Bold letters indicate identical amino acids between peptides.

| | | |
|---|---|---|
| EGFR p580-598 | IQCAHYIDGPHCVKTCPAG | (SEQ ID NO. 1) |
| HER2 p585-603 | VACAHYKDPPFCVARCPSG | (SEQ ID NO. 2) |
| HER3 p574-592 | AQCAHFRDGPHCVSSCPHG | (SEQ ID NO. 3) |
| HER4 p578-596 | TKCSHFKDGPNCVEKCPDG | (SEQ ID NO. 4) |

This specific, active immunotherapy approach to targeting multiple ErbB family members has the potential to establish cost-effective, long-lasting anti-tumor immunity to tumor cells that express EGFR, HER2 or HER3 epitopes with limited autoimmune pathology or the side effects associated with multiple infusion passive immunotherapy.

The EGFR p580 antibody cross-reactive inhibition of EGFR-negative, HER2-positive tumor cells was unexpected. Alternative experimental B cell epitope peptide vaccines derived from ErbB family proteins are not designed to target more than one ErbB family member (Dakappagari N K et al. (2000) Cancer Res 60: 3782-9; Dakappagari N K et al. (2005) J Biol Chem 280: 54-63; Dakappagari N K et al. (2003) J. Immunol. 170: 4242-53; Garrett J T et al. (2007) J Immunol 178: 7120-31). A smaller p585-598 HER2 peptide, VACAHYKDPPFCVA (SEQ ID NO. 5), representing a portion of the HER2 region homologous to EGFR p580 (SEQ ID NO. 2; Table 1), failed to elicit antibodies that bound strongly to native HER2, most likely because the 14-mer peptide was too short to elicit cross-reactive antibodies specific to HER2 (Garrett J T et al. (2007) J Immunol 178: 7120-31).

The structure and function of the p580 epitope in the native EGFR protein confirms that it is a potential therapeutic cancer vaccine target in EGFR, and also in HER2 and HER3. Several key residues, including cysteines, are conserved in all three proteins (Table 1). In crystal structures of the extracellular domains of EGFR, HER2, HER3 and HER4, this epitope is constrained and structurally conserved. In EGFR, HER3 and HER4, this region functions as part of the interdomain interface between domains II and IV that maintains these receptors in an inactive, tethered conformation (FIG. 1A-1D). Trastuzumab, which is not cross-reactive, recognizes a conformational HER2 epitope that includes residues homologous to a segment of the EGFR p580 epitope. The HER2 domain II dimerization arm targeted by pertuzumab corresponds to the HER2 domain II region that interacts with the p580 epitope region in domain IV. The p580 epitope location at the domain II/IV interface of the inactive, tethered conformation of EGFR (FIG. 1A-1D), HER3 and HER4 suggests that the epitope may be more accessible in tumor cells with EGFR, HER2 and/or HER3 activated by overexpression.

Approximately 20-30% of high-grade gliomas (GBM) express EGFRvIII with constitutively activated tyrosine kinase activity (Gan H K et al. (2009) J Clin Neurosci 16: 748-54). This tumor-specific EGFR variant has been associated with resistance to cetuximab. Rindopepimut, a 13-amino acid EGFRvIII-specific peptide conjugated to KLH, was evaluated in glioblastoma clinical trials (Babu R et al. (2012) Core Evid 7: 93-103). Although it targets the tumor-specific EGFRvIII, its efficacy can be limited by loss of the mutant EGFRvIII in patients (Heimberger A B et al. (2009) Expert Opin Biol Ther 9: 1087-98). These clinical features suggest that the p580 vaccine strategy targeting EGFR, HER2 and HER3 may provide a more efficacious therapy.

Preliminary data presented in this section demonstrate that EGFR p580 peptide immunization circumvents self-tolerance to EGFR and that the resulting anti-peptide antibodies cross-react with homologous sequences from EGFR, HER2 and HER3. The EGFR p580 peptide shares 58%, 68% and 53% sequence identity with corresponding regions of human HER2, HER3 and HER4, respectively (Table 1). More importantly, the EGFR p580 antibodies are capable of inhibiting the growth of both EGFR-overexpressing cells and EGFR-negative, HER2-positive tumor cells.

Figure 3:
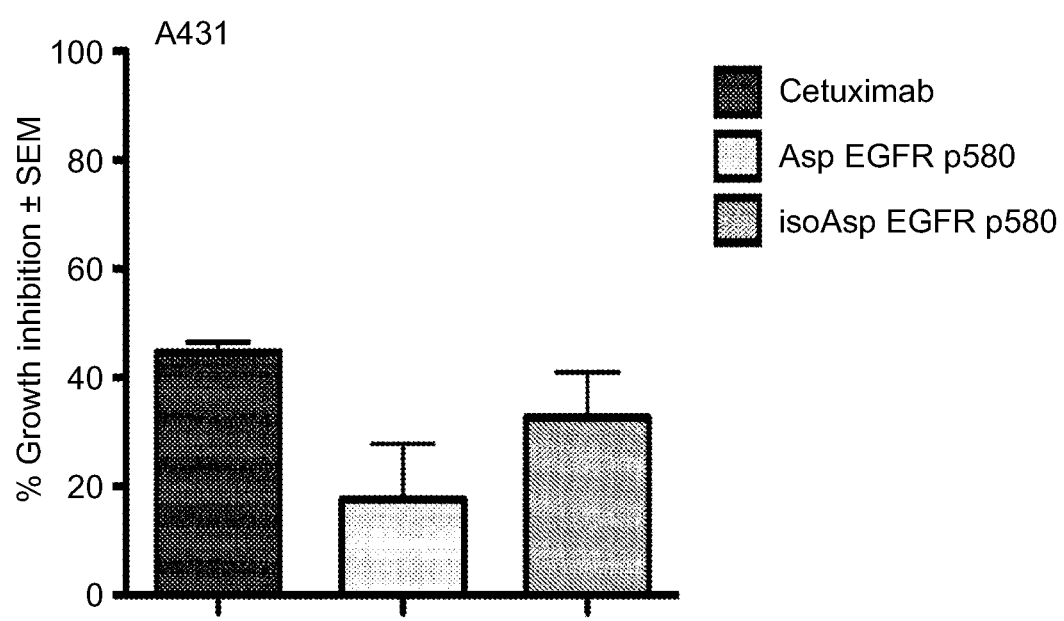
FIG. 3 is a graph showing the growth inhibition of A431 cells by EGFR p580 immune serum. A431 cells were incubated with 1:25 dilution of serum or 10 μg/ml cetuximab for 48 h. Cell proliferation was measured by 3H-thymidine incorporation.

EGFR p580 mouse immune sera bind to the EGFR overexpressing human A431 epidermoid carcinoma cell line at an epitope distinct from that recognized by cetuximab (FIG. 2). This is expected from the cetuximab-EGFR extracellular domain co-crystal structure (FIG. 1). EGFR p580 immune serum also inhibits A431 cell growth in a manner comparable to that of the cetuximab positive control (FIG. 3). Rituximab, a non-specific IgG1 isotype control did not inhibit any A431 growth (data not shown), while cetuximab inhibited A431 cell growth by 45%. IsoAsp modified EGFR p580 immune serum inhibited A431 tumor cell growth by 33%.

Figure 4A:
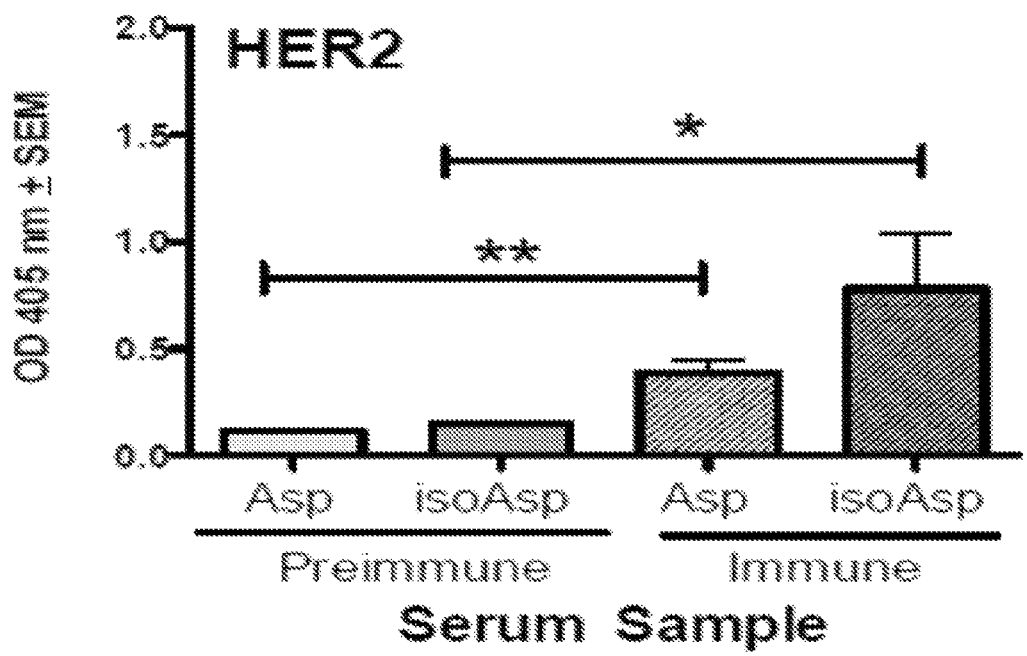
FIG. 4A and FIG. 4B are graphs showing that anti-EGFR p580 sera bind recombinant human HER2 and HER3 proteins in an Enzyme Linked Immunosorbent Assay (ELISA).
Figure 4B:
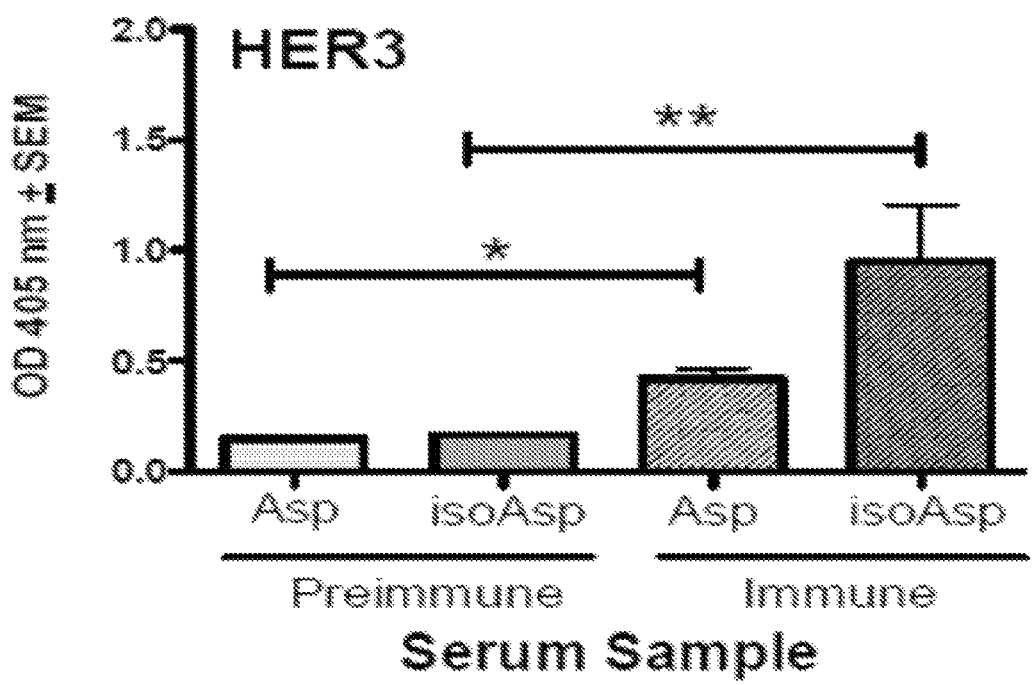

HER2 is overexpressed in a subset of breast cancers and is a target of the therapeutic antibody trastuzumab. The sequence homology of the ErbB peptides (Table 1) prompted us to test EGFR p580 immune sera for antibodies that bind homologous sites on HER2, HER3 and HER4 proteins. Immune sera from Asp and isoAsp EGFR p580 (1:100 dilution) bound to intact human HER2 and HER3 extracellular domains by ELISA (FIG. 4). In contrast, neither Asp nor isoAsp EGFR p580 antisera bound the homologous region of HER4 (data not shown).

Figure 9A:
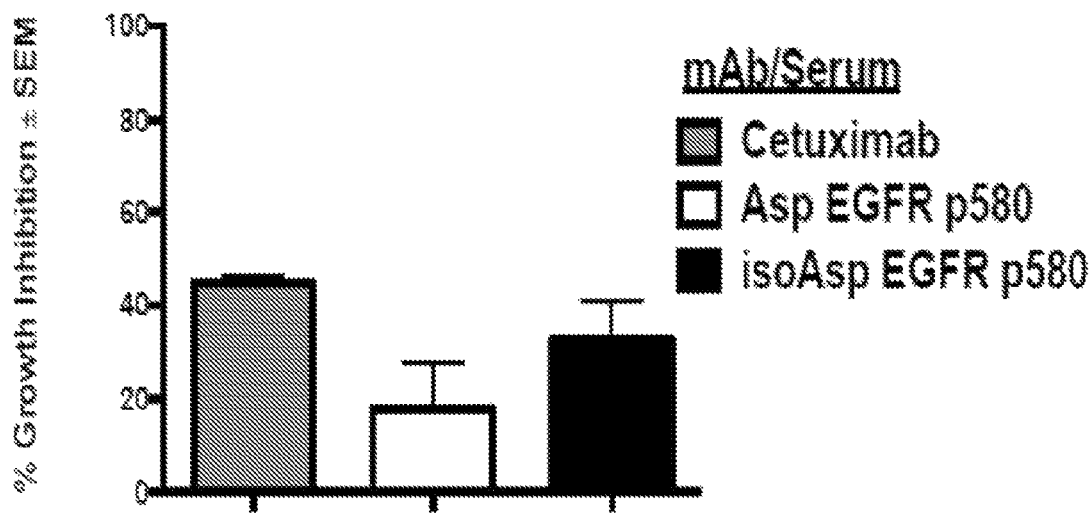
FIG. 9A-FIG. 9D depicts sera from anti-EGFR peptide immune mice inhibit the growth and promote the killing of both EGFR and HER2 expressing cells.
Figure 9B:
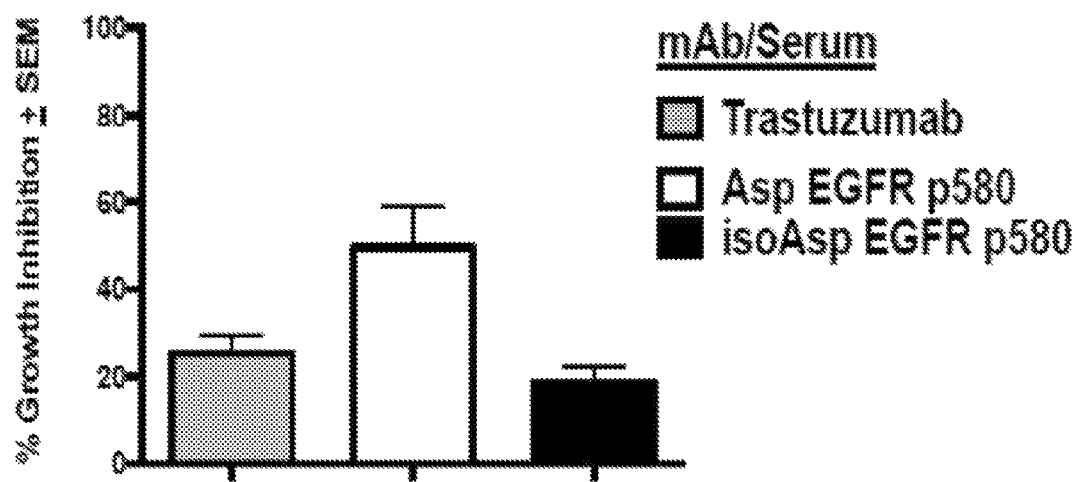

The EGFR p580 antiserum was also found to inhibit the growth of MDA-MB-453 breast carcinoma cells that are EGFR-negative and HER2-positive by flow cytometry. Similar to the growth inhibition assays using A431 cells, MDA-MB-453 cells were incubated with EGFR peptide antisera, as well as cetuximab, rituximab and trastuzumab as controls. Cells were incubated for three days with 1:25 dilutions of sera from either Asp or isoAsp p580 immunized Balb/c mice. Cell proliferation was measured by 3H-thymidine incorporation. Rituximab and cetuximab failed to inhibit MDA-MB-453 cell growth at the 10-40 mg/ml concentrations tested (FIG. 9). However, Asp EGFR p580 antisera inhibited tumor cell growth by 50%, and isoAsp EGFR p580 antisera inhibited tumor cell growth by 19% (FIG. 9). In FIG. 9B, trastuzumab inhibited growth of MDA-MB-453.

In summary, antibodies elicited by EGFR p580 isoforms bind homologous epitopes from EGFR, HER2 and HER3. The antibodies crossreact with HER2 and inhibit the growth of EGFR-positive and EGFR-negative, HER2-positive tumor cells.

The EGFR p580 peptide will be used as a lead peptide to develop more potent and stable candidate cancer vaccines. Antisera from mice immunized with p580 analogs conjugated to KLH will be assessed for antibody cross-reactivity with corresponding EGFR, HER2, HER3 and HER4 epitopes.

Peptides will be synthesized and purified by commercial vendors (GenScript or Anaspec) that specialize in custom peptide synthesis, process development and the manufacturing of peptides. Unless otherwise specified, all peptides will be synthesized with an N-terminal acetylation and C-terminal amidation (Table 2) and purified by HPLC. Peptide quality will be verified by both HPLC and mass spectrometry. Selected peptides will be conjugated to KLH carrier proteins for immunizations (Table 2). Peptides will be linked to KLH with standard conjugation methods to the N- or C-termini of the modified p580 peptides.

TABLE 2

Peptides for immunizations (SEQ ID NO. 1)
IQCAHYIDGPHCVKTCPAG (p580)

Ac-IQCAHYIDGPHCVKTCPAG-amide

TABLE 2-continued

Peptides for immunizations (SEQ ID NO. 6)
Ac-IQCAHYIDGPHCVKTSPAG-amide (SEQ ID NO. 7)
KLH-AoaIQCAHYIDGPHCVKTSPAG-amide (SEQ ID NO. 8)
Ac-IQCAHYIDGPHCVKTSPAG(KAoa)(-amide)-KLH (SEQ ID NO. 9)
KLH-AoaIQCAHYIDPPHCVKTSPAG-amide (SEQ ID NO. 10)
KLH-AoaIQCAHYIDGPHCVKTSPAG-amide Lines indicate intramolecular disulfide bonds.
KLH, keyhole limpet hemocyanin; Aoa = aminooxyacetic acid for KLH coupling; D, isoaspartyl residue.

The synthetic EGFR p580 peptide is based on EGFR residues 580-598 (IQCAHYIDGPHCVKTCPAG SEQ ID NO. 1). The peptide does not have extensive homology to human proteins outside of the ErbB family. The peptide includes the surface exposed residues that are highly conserved in ErbB proteins (Table 1, FIG. 1). The 19-mer p580 peptide is amenable to chemical synthesis, yet is large enough to elicit an antibody response and has two charged residues to enhance solubility. This peptide has cysteines that can be cyclized to help constrain the peptide in a native conformation. The p580 EGFR sequence is identical between mouse and man. Thus, immunity in the mouse is directly relevant to breaking immune tolerance in humans and in mouse tumor models.

Potential liabilities of the p580 peptide as a vaccine candidate include the three cysteines and an acid-labile Asp-Gly bond. These properties can affect synthesis, purification and induce disulfide bonding. Cysteines can rapidly oxidize and negatively alter peptide synthesis and purification. To address these issues, we propose to replace one of the p580 cysteine residues with a structurally related serine residue and cyclize the other two cysteines (Table 2), which are linked in the native protein. If necessary, we will replace the Gly in the EGFR p580 Asp-Gly bond with other with residues, beginning with the Pro residue present in HER2 at this position (Table 2). We also expect that p580 peptide stability can be improved with affecting immunogenicity by N-terminal acetylation and C-terminal amidation.

Example 2: Epidermal Growth Factor Receptor (EGFR) Peptide Vaccination Induces Cross-Reactive Immunity to Human EGFR, HER2, and HER3

A. Materials and Methods
(i) Peptides and Recombinant Proteins

The W.M. Keck Foundation Biotechnology Resource Laboratory at Yale University synthesized all peptides used for these studies. Six different murine (mu) and human (hu) EGFR peptides were synthesized as both the Asp and iso-Asp isoforms. The peptide sequences are as follows (numbering based on the human EGFR precursor protein amino acid sequence; iso-Asp designated in bold): mu/hu p566-584, AMNITCTGRGPDNCIQCAH (SEQ ID NO: 5); mu/hu p572-590, TGRGPDNCIQCAHYIDGPH (SEQ ID NO: 11); mu/hu p580-598, IQCAHYIDGPHCVKTCPAG (SEQ ID NO: 1); mu p596-615, PAGIMGENNTLVWKY-ADANN (SEQ ID NO: 12); hu p596-615, PAGVM-GENNTLVWKYADAGH (SEQ ID NO: 13); and mu p605-623, TLVWKYADANNVCHLCHAN (SEQ ID NO: 14). The sequences for the human HER2 peptides were: hu HER2 p585-603, VACAHYKDPPFCVARCPSG (SEQ ID NO: 2); hu HER3 p574-592, AQCAHFRDGPHCVSS-CPHG (SEQ ID NO: 3) and hu HER4 p578-596, TKCSHFKDGPNCVEKCPDG (SEQ ID NO: 4). Peptides were reconstituted in water and stored at −20° C. The extracellular domain of HER2 was a kind gift of Dr. Daniel Leahy, John Hopkins University School of Medicine, and was expressed and purified as previously described (Cho H S et al. (2003) Nature 421:756-60). Recombinant human HER3 extracellular domain was purchased from R&D Systems.

(ii) Cell Lines

The human epidermoid carcinoma cell line A431, which overexpresses EGFR, was obtained from ATCC (CRL-1555). A431 cells were maintained in high glucose DMEM (Gibco) containing 10% FBS. The HER2 expressing human mammary gland carcinoma cell line MDA-MB-453 (ATCC HTB-131), which does not express EGFR, was maintained in DMEM/Hams F12 (Gibco) containing 10% FBS. Both cell lines were authenticated by ATCC for viability, growth, and morphology. Cell lines were stored according to the supplier's instructions and were used over a period of no more than 5 months post-thaw. TUBO-EGFR cells (a kind gift of Dr. Yang-Xin Fu, Univ. of Chicago) are a HER2/neu-dependent TUBO cell line originally derived from Balb/c mice and transfected with human EGFR (Yang X et al. (2013) Mol Ther 21:91-100). These cells were maintained in DMEM containing 10% FBS, 2 mmol/l L-glutamine, 0.1 mmol/1 MEM nonessential amino acids, 100U/ml penicillin and 10 µg/ml streptomycin (Yang X et al. (2013) Mol Ther 21:91-100).

(iii) Antibodies

Cetuximab (anti-human EGFR monoclonal antibody) and trastuzumab (anti-human HER2 monoclonal antibody) were kind gifts of Drs. David Rimm and Michael DiGiovanna, respectively (Yale University School of Medicine). Rituximab (human anti-CD20 monoclonal antibody) was obtained from the Smilow Cancer Center Pharmacy, New Haven, CT.

(iv) Animals and Immunization

Female Balb/c or female C57BL/6 mice, 6-8 weeks old, were obtained from the National Cancer Institute. All mice were housed at the Yale University School of Medicine Animal Facility. All protocols were consistent with accepted guidelines of the National Institutes of Health for the care and use of laboratory animals as well as approved by the Yale University Institutional Animal Care and Use Committee. For the generation of antibody, three to five Balb/c or C57BL/6 mice per group were immunized intraperitoneally and subcutaneously in one footpad with 100 µg of peptide emulsified 1:1 of PBS and complete Freund's adjuvant (CFA). Twenty-one days later, mice were boosted intraperitoneally and subcutaneously in the other footpad with 100 µg of immunizing peptide emulsified in incomplete Freund's adjuvant (IFA). Sera were collected via retro-orbital bleed on day 28 for antibody analyses. For T cell assays, mice were immunized by the same route of administration with 100 µg of peptide emulsified 1:1 in CFA. Fourteen days later, mice were boosted by the same route of administration with 100 µg of the immunizing peptide emulsified 1:1 in IFA. Twenty-one days post-immunization, mice were euthanized, draining lymph nodes were excised and single cell suspensions prepared for experimental use as described below.

(v) T Cell Immunoassays

Single cell suspensions were prepared from the popliteal, inguinal, and periaortic lymph nodes of immunized C57BL/6 mice. Cells were plated in triplicate in 96-well flat bottom plates at $5 \times 10^5$ cells per well in which serially diluted peptides had been added. Cells were incubated at 37° C., 5% CO2 for three days, at which time they were pulsed with 1 µCi $^3$H-thymidine. Cultures were incubated an additional 18 h, harvested onto filter membranes and 3H-thymidine incorporation was quantified (Betaplate, Wallac). Cells stimulated with purified protein derivative (PPD) from M. tuberculosis H37 RA (Difco Laboratories) served as a positive control for cell proliferation.

(vi) ELISA

Polystyrene microtiter plates (Nunc) were coated with either 50 µg/ml peptide or 1 µg of rHER2 or rHER3 extracellular domains in buffer (0.05 M carbonate-bicarbonate buffer, pH 9.6; Sigma) and incubated overnight at 4° C. Wells were washed, blocked with PBS containing 3% bovine serum albumin (BSA) followed by the addition of serum samples (1:100 dilution) for 2 h at room temperature. Alkaline phosphatase conjugated-goat anti-mouse IgG antibody (Southern Biotech) was added to the wells at a 1:1000 dilution and incubated at room temperature for 1.5 h. Wells were washed one last time, and developed by the addition of the substrate p-nitrophenyl phosphate (Sigma). Wells were read on a SpectraMax 450 ELISA reader (Molecular Dynamics) at 405 nm.

(vii) Flow Cytometry

A431 and MDA-MB-453 cell lines were used for antibody binding flow cytometry experiments. Cells ($10^5$ cells/sample) were stained with a 1:100 dilution of serum in PBS with 0.1% BSA and 0.05% sodium azide for 1 h at 4° C. Cells were washed and incubated with a 1:100 dilution of either anti-mouse IgG fluorescein isothiocyanate (FITC; Sigma) or anti-human IgG AlexaFluor 488 (Molecular Probes, Invitrogen) for 1 h at 4° C. Some samples were further stained using anti-FITC AlexaFluor 488. Cells were washed and fixed in PBS+1% paraformaldehyde. Cells were analyzed on a FACSCalibur (BD Biosciences) with FlowJo software (Tree Star). Controls included unstained cells and cells stained with secondary antibody alone. A431 cells stained with cetuximab (5 µg/ml) and MDA-MB-453 cells stained with trastuzumab (5 µg/ml) were used as positive controls for EGFR and HER2 staining, respectively.

(viii) Tumor Cell Growth Inhibition

The ability of immune sera to inhibit the growth of the EGFR overexpressing A431 cell line was measured using a 3H-thymidine assay. Briefly, A431 cells were grown to log phase, washed, resuspended in DMEM+10% FBS and plated at 4000 cells per well in a 96-well flat bottom plates. Cells were allowed to adhere overnight prior to the addition of 1:25 dilutions of heat inactivated (56° C., 30 min) immune or preimmune sera in DMEM+1% FBS. All samples were run in triplicate. Cells were incubated for 48 h at 37° C. 5% CO2, at which time 1 µCi $^3$H-thymidine (Perkin Elmer) was added to each well. Cells were further incubated for 18 h then harvested and thymidine incorporation counted by a beta plate reader. Cetuximab (10 µg/ml) served as the positive control while rituximab (10 µgimp, another humanized IgG1 antibody, served as an isotype control. Percent growth inhibition was calculated as [(pre-immune serum CPM−immune serum CPM)/preimmune serum CPM]×100.

Growth inhibition of MDA-MB-453 cells by EGFR immune sera was done as described above for the growth inhibition of A431 cells, with the exception that cells were plated at 1000 cells/well and trastuzumab, rituximab and cetuximab (each at 40 µg/ml) served as controls.

(ix) ADCC Assays

All experimental sera were heat-inactivated (56° C., 30 min) prior to use. A431 or MDA-MB-453 cells were incubated with a 1:25 dilution of heat-inactivated sera or control antibody (20 µg/ml) 30 min at 37° C. in 96-well U bottom plates. Freshly isolated human peripheral blood mononuclear cells (PBMC) from healthy donors were incubated with antibody coated target cells at a 50:1 effector to target ratio for 4 h at 37° C. Fifty microliters of each cell culture supernatant was then assayed for lactate dehydrogenase released from dead cells using the CytoTox96 Non-Radioactive Cytotoxicity Assay (Promega) per manufacturer's instructions. Percent cytotoxicity was calculated as [(experimental-effector spontaneous-target spontaneous)/(target maximum-target spontaneous)]×100.

(x) In Vivo Tumor Assays

Female Balb/c mice were immunized with either Asp or isoAsp EGFR p580 as described above for the generation of antibody. TUBO-EGFR cells ($5 \times 10^5$) were injected subcutaneously on the right flank of mice. Tumor volume was calculated by measuring three orthogonal axes (a, b, and c) with digital calipers, with the tumor volume=abc/2 (Cho H S et al. (2003) *Nature* 421:756-60).

(xi) Statistical Analysis

Results are expressed as means±SEM and p values calculated using the Mann-Whitney test or the Student t-test (Prism, GraphPad Software). Results were considered significant if $p<0.05$.

Figure 5A:
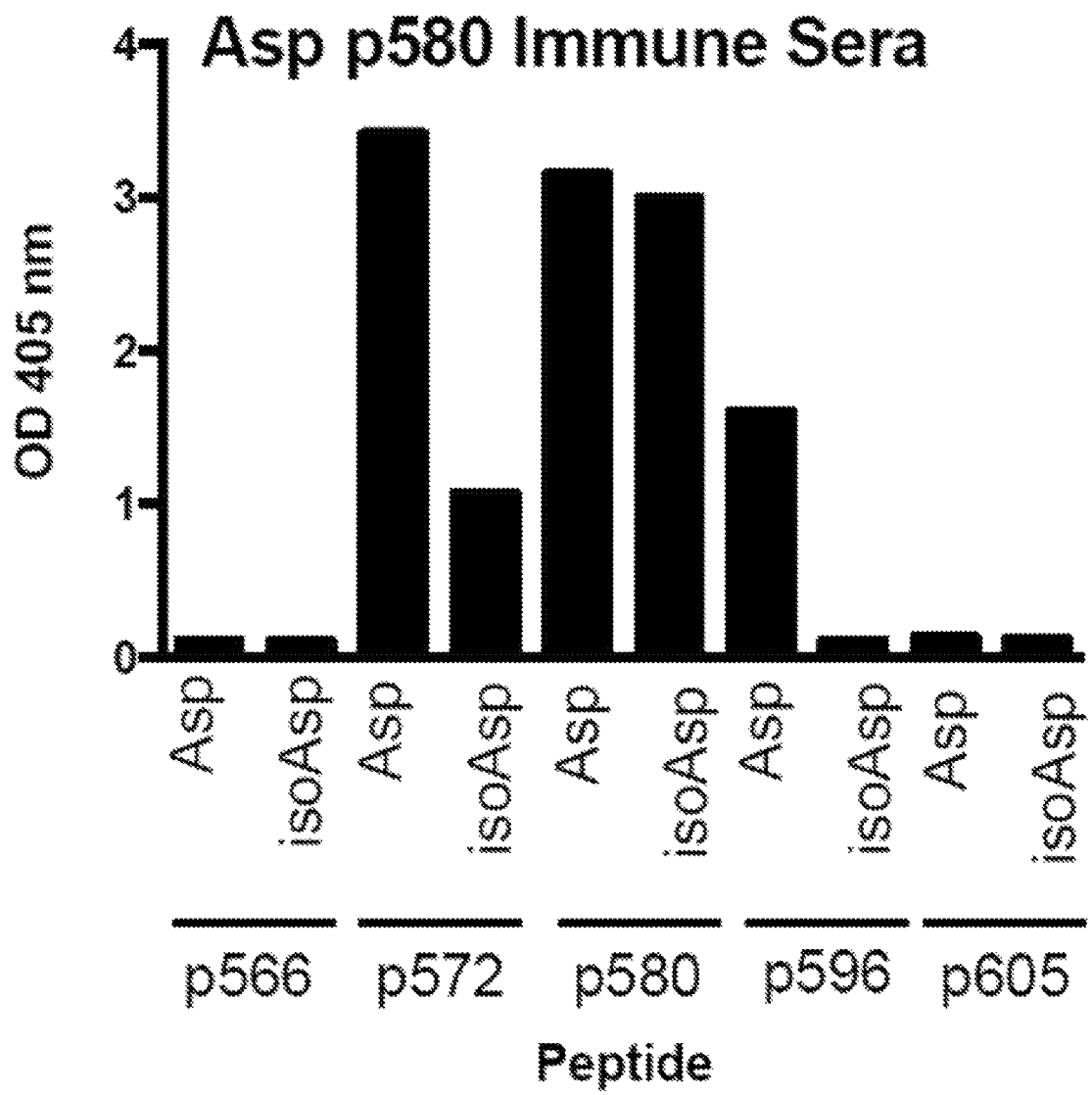
FIG. 5A-FIG. 5D depicts graphs showing immunization with EGFR p580 peptide isoforms generate peptide specific antibody and T cell responses. Individual serum samples from Asp EGFR p580 immune (FIG. 5A) or iso-Asp EGFR p580 immune (FIG. 5B) C57BL/6 mice were tested by ELISA for binding to flanking SEQ ID NOs: 5, 11, 1, 12 or 13, and 14. Pre-immune sera had <0.1 O.D. units of antigen binding. Results are representative of four mice per immunization group and the experiment was repeated twice.
Figure 5B:
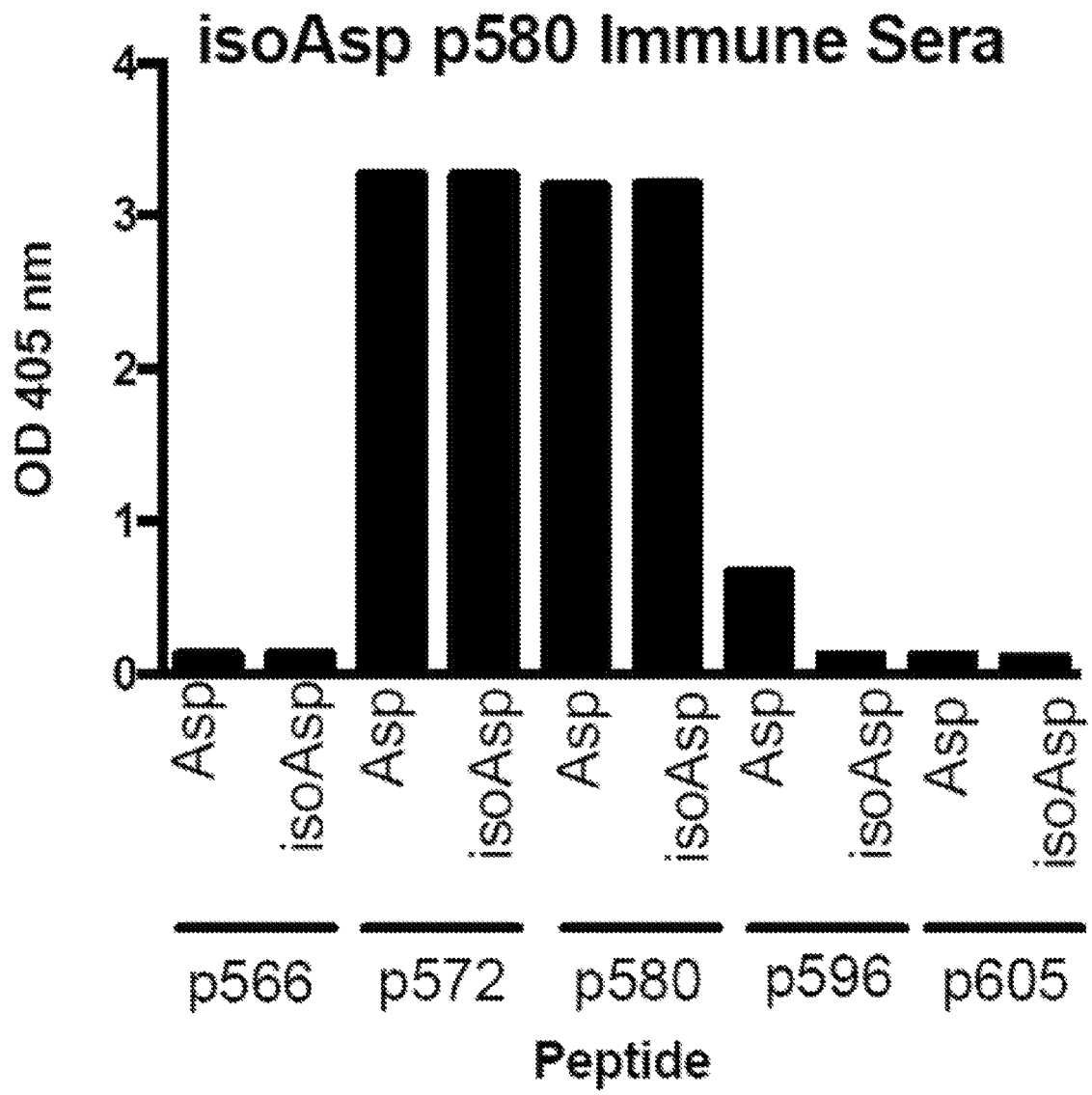

B. Results (i) Anti-EGFR Antibodies are Elicited by Immunization with EGFR Peptide p580 Isoforms Sites chosen for peptide-based induction of immunity were based on extracellular domain sequences near the transmembrane region of ErbB family proteins with sequence homology between EGFR, HER2 and HER3. HER2 is a member of the ErbB family and is often co-expressed with EGFR and also overexpressed in certain cancers. We aligned the amino acid sequences of the HER2 and EGFR proteins and identified a corresponding amino acid residue region that spans EGFR amino acids 596-615 (p596). We synthesized four additional overlapping 19- or 20-mer peptides derived from the murine and/or human EGFR p566-623 amino acid sequence. The peptide sequences, including p580, are identical between humans and mice with the exception of p596 and p605, which have murine and human sequences that differ by three amino acids. Mice were immunized with the Asp or iso-Asp modified forms of each peptide to increase the possibility of overcoming host immune tolerance to murine EGFR. Antisera were collected and examined by ELISA for antibodies against the panel of EGFR peptides. All mice developed antibodies with binding activity to the immunizing peptide. Peptide p580 isoforms elicited strong antibody responses with cross-reactive binding to multiple peptides (FIG. 5A & FIG. 5B). Immunization with Asp p580 (IQCAHYIDGPHCVKTCPAG) (SEQ ID NO: 1) generated antibodies against Asp and iso-Asp p580, as well as Asp and iso-Asp p572 and Asp p596 (FIG. 5A). A similar pattern was seen upon immunization with iso-Asp p580 in which sera bound strongly to both isoforms of p572 and Asp 596 (FIG. 5B).

(ii) Peptide Immunization Elicits T Cells that Recognize Both Isoaspartyl and Aspartyl Isoforms of Peptide p580

Figure 5C:
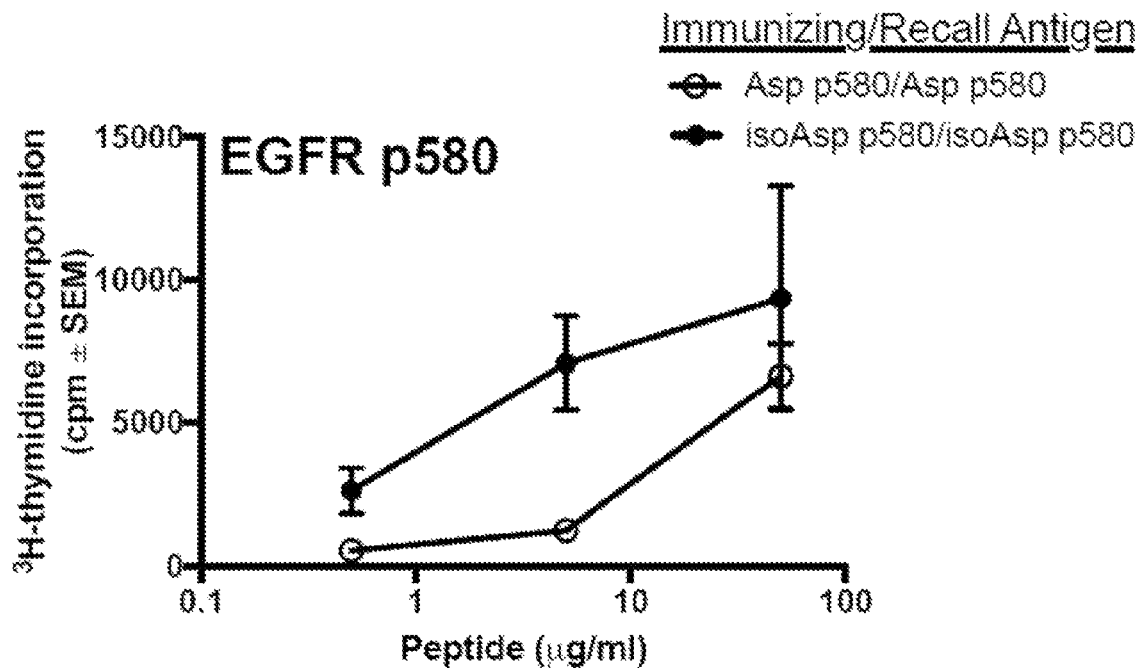
Figure 5D:
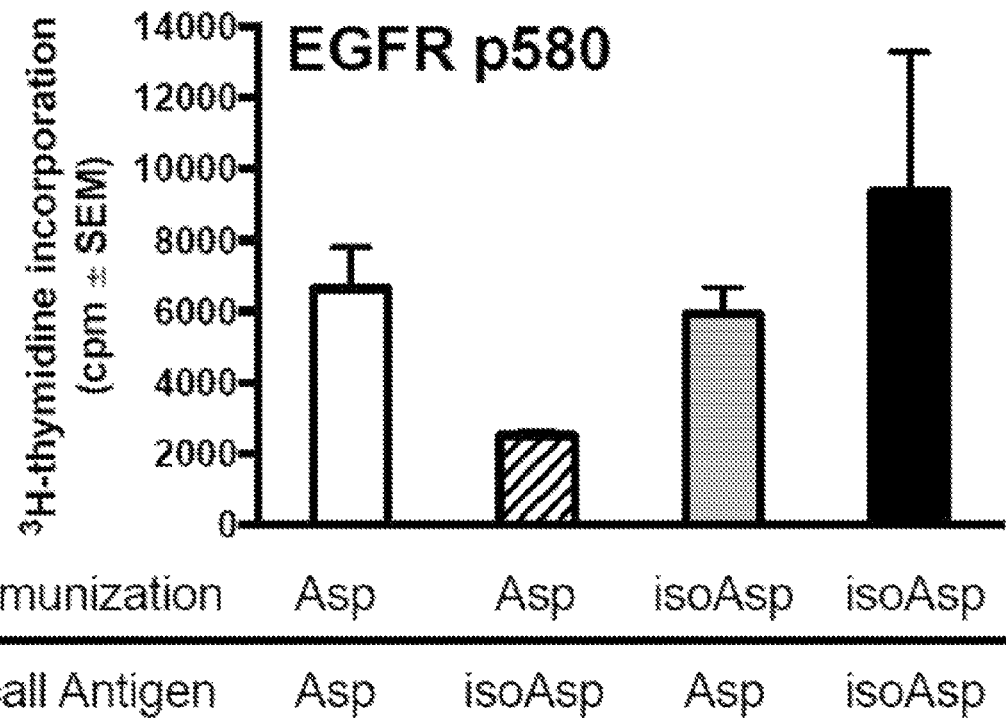

Since p580 isoforms both induced high titers of antibody that demonstrated cross-reactivity to other EGFR peptides, we tested the ability of this immunization to stimulate CD4 T cell responses. In conventional proliferation assays, C57BL/6 mice were immunized with either the Asp or iso-Asp isoforms of p580 in Freund's adjuvant (IFA). After 21 days, lymph node cells were isolated and re-stimulated for 72 h in vitro with peptide. Immunization with the p580 peptide resulted in strong T cell responses to both Asp and iso-Asp p580, with a more robust response in those mice immunized with iso-Asp p580 (FIG. 5C). More importantly for inducing reactivity with native EGFR, T cells from mice immunized with the iso-Asp modified p580 isoform also recognize Asp p580 (FIG. 5D), demonstrating cross-reactivity of the T cell receptor for both isoforms of the EGFR peptide.

(iii) Sera from EGFR p580 Immune Mice Bind Human EGFR

Figure 6A:
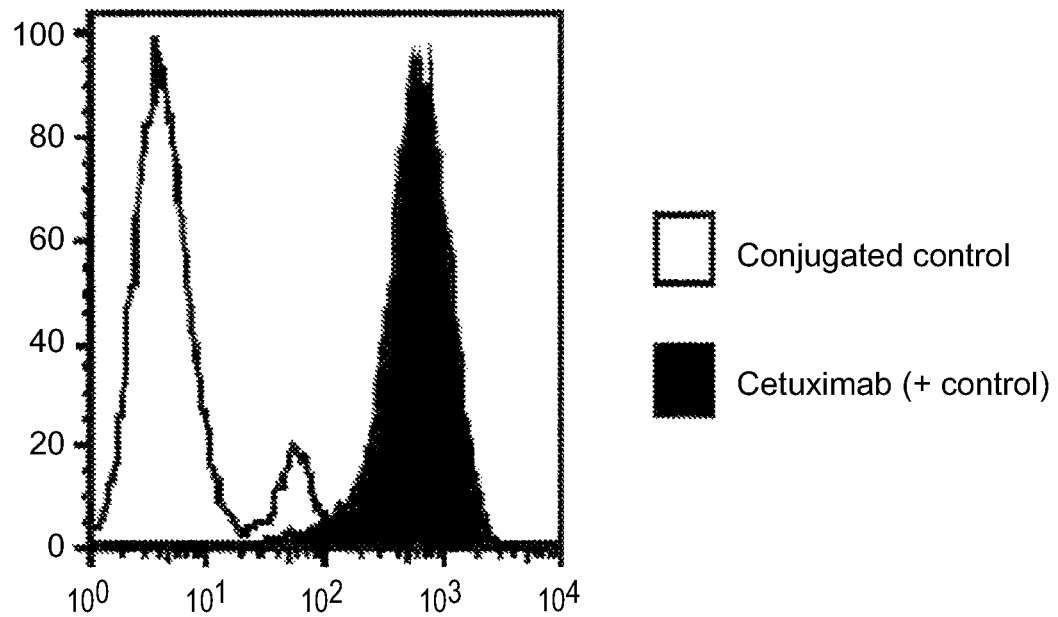
FIG. 6A-FIG. 6C depicts sera from mice immunized with mouse iso-Asp p580 bind human A431 cells. Sera from Balb/c mice immunized with either Asp or iso-Asp p580 were incubated with A431 cells and stained for flow cytometry analysis.
Figure 6B:
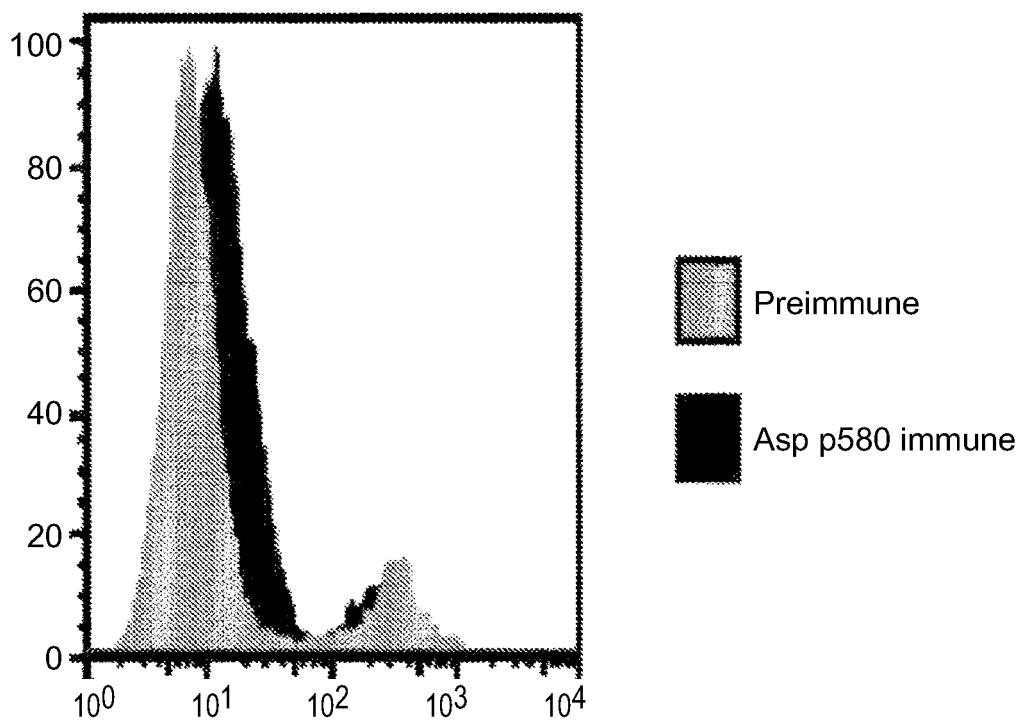
Figure 6C:
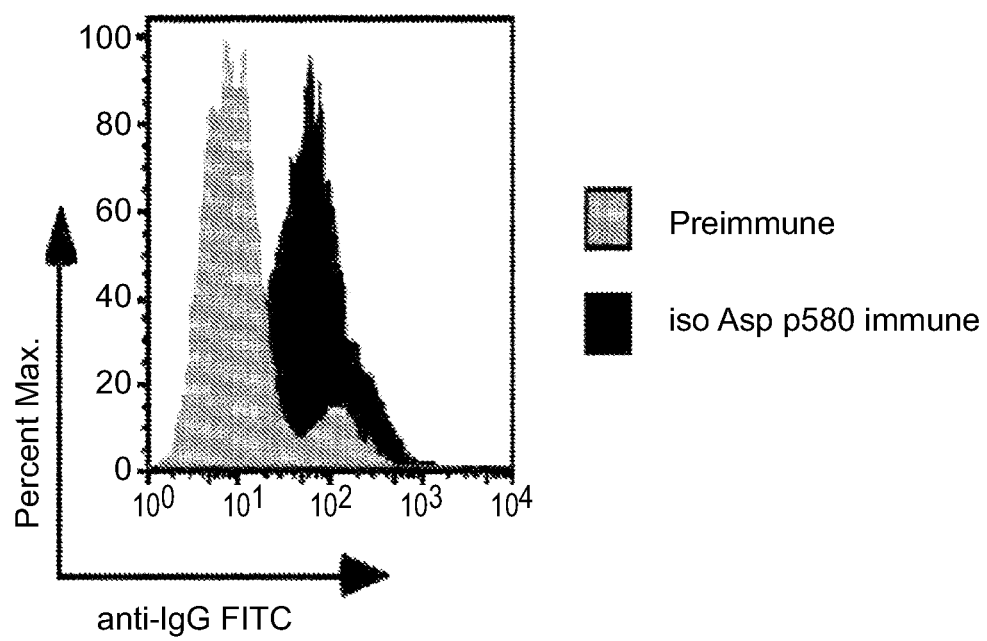

We next determined if the antibodies generated during immunization with p580 isoforms bound to intact human EGFR on cells. For these studies, A431 cells, a human EGFR overexpressing tumor cell line, were stained with peptide-induced antisera and analyzed by flow cytometry. As a control for staining, we stained A431 cells with cetuximab. A431 cells express EGFR on their surface and stain with cetuximab (FIG. 6A). Asp p580 immune sera stained A431 cells above that seen with pre-immune sera (FIG. 6B). However, staining with iso-Asp p580 immune sera revealed greater than a 10-fold shift in staining intensity (FIG. 6C). These results demonstrate that the iso-Asp form of EGFR p580 isoform elicits a strong, high titer antibody response that recognizes human EGFR on tumor cells.

(iv) Anti-EGFR p580 Antibodies Bind HER2 and HER3

Figure 7A:
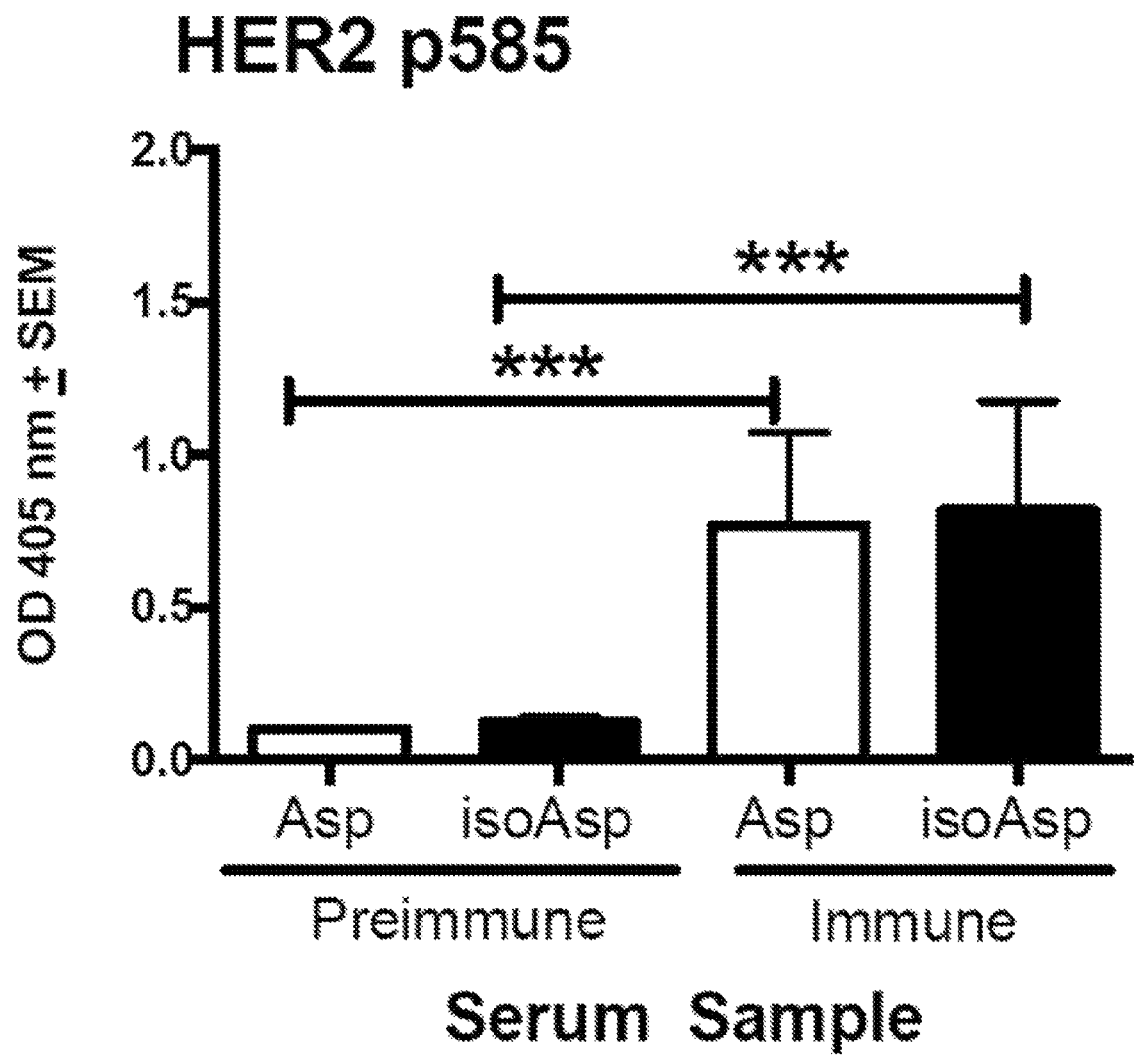
FIG. 7A-FIG. 7D depicts anti-EGFR p580 antibodies bind homologous HER2 and HER3 peptides and proteins. Sera from Balb/c mice immunized with Asp p580 or iso-Asp p580 were tested by ELISA for antibody binding to (FIG. 7A) HER2 p585 peptide, (FIG. 7B) HER3 p574 peptide, (FIG. 7C) recombinant HER2 extracellular domain and (FIG. 7D) recombinant HER3 extracellular domain by ELISA. Results represent nine to ten mice per group. , $p<0.01$; *, $p<0.001$.
Figure 7B:
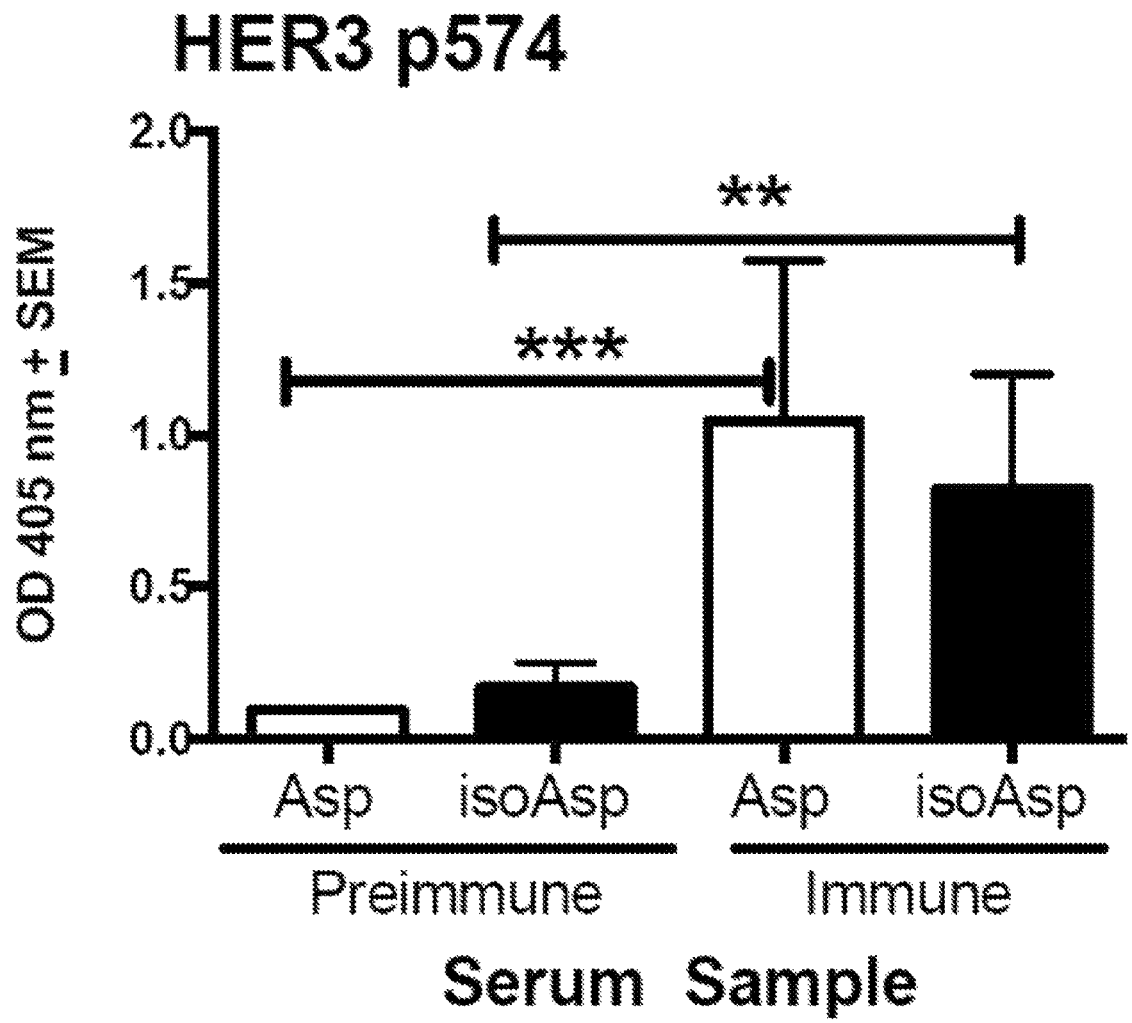

EGFR is a member of the ErbB family of tyrosine kinases, which also includes HER2, HER3, and HER4. HER2 is overexpressed in a subset of breast cancers and is itself a target of the therapeutic antibody trastuzumab. Examination of the amino acid sequences of EGFR and HER2, HER3, and HER4 extracellular domains revealed significant homology between these four proteins in the domain IV region represented by EGFR p580 (Table 1; FIG. 1A-1D). Thus, we next tested anti-p580 immune serum for the ability to bind homologous peptides of human HER2, HER3, and HER4. Immune sera from both Asp and iso-Asp p580 bound HER2 p585 by ELISA (FIG. 7A) as well as HER3 p574 (FIG. 7B). In contrast, neither the Asp nor iso-Asp EGFR p580 antiserum bound the homologous HER4 p578 peptide (data not shown).

Figure 7C:
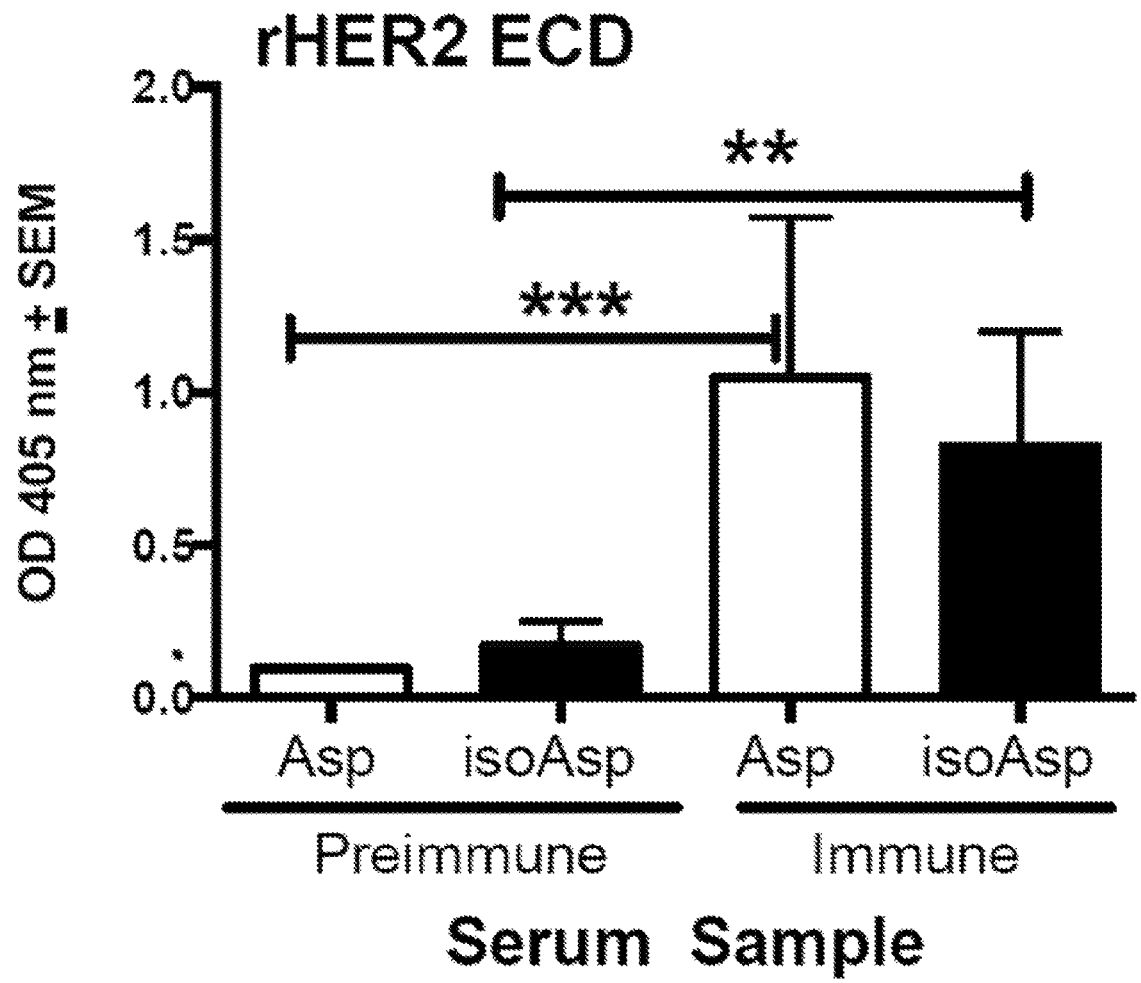
Figure 7D:
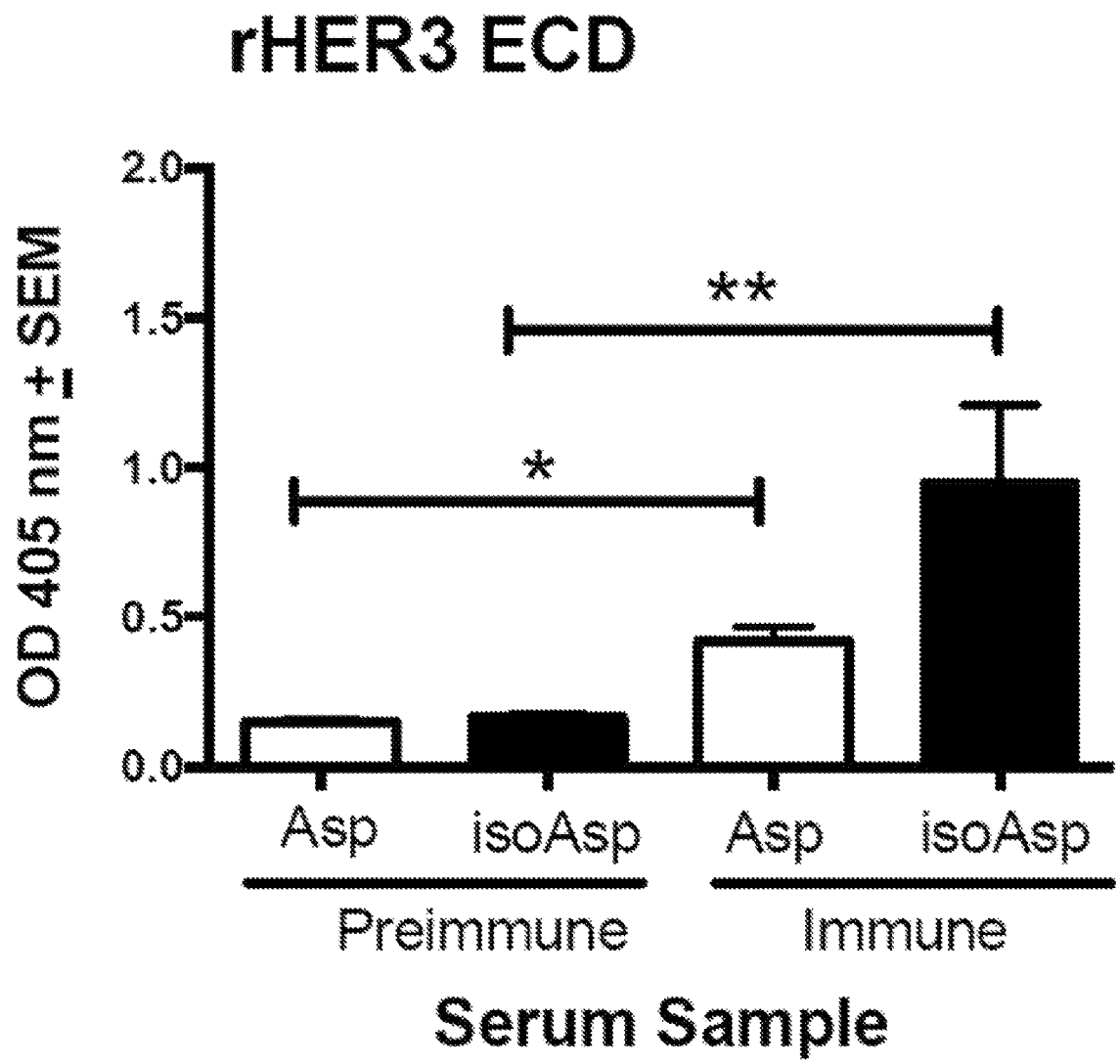
Figure 8B:
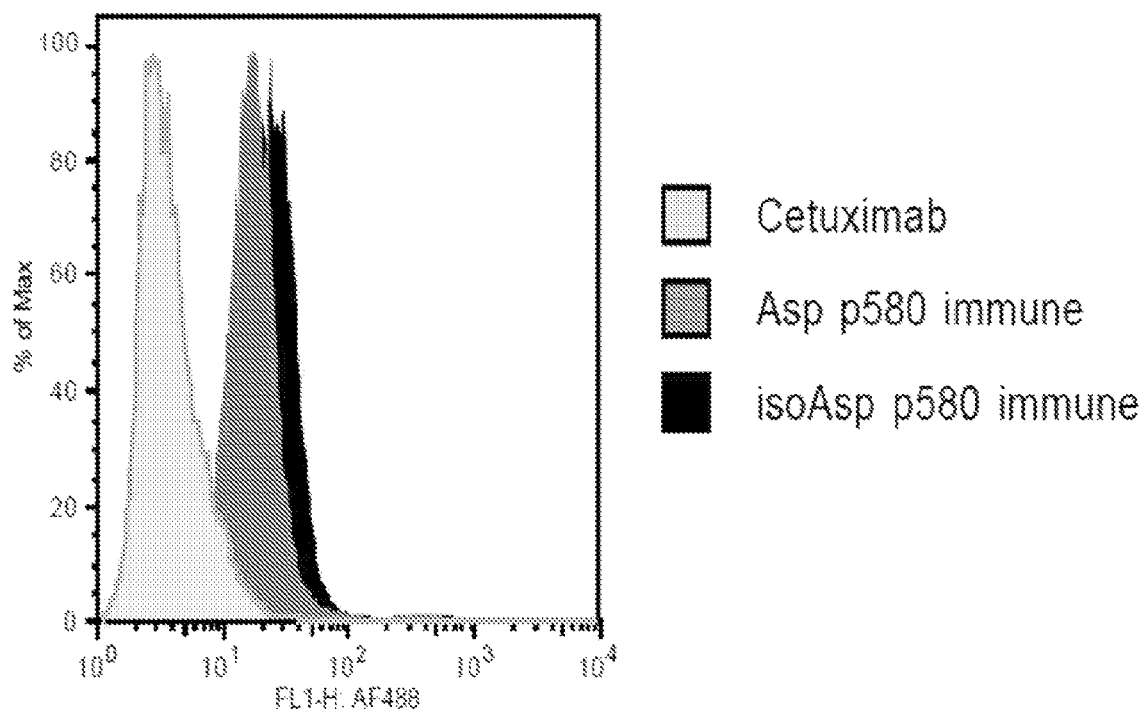

We examined the ability of EGFR p580 antiserum to bind the extracellular domain of the HER2 protein. Asp and iso-Asp EGFR p580 antiserum bound the recombinant extracellular domain of HER2 by ELISA (FIG. 7C) while sera from preimmune mice did not. In a similar manner, Asp and iso-Asp EGFR p580 immune serum bound the HER3 extracellular domain (FIG. 7D). EGFR p580 antisera also bound HER2 on living human tumor cells (FIG. 8A-8B). Flow cytometry was used to assess antibody binding to the cell line MDA-MB-453, which expresses HER2 mRNA but lacks EGFR mRNA expression as determined by RT-PCR (Kao J et al. (2009) *PLoS One* 4:e6146). As expected, the anti-HER2 antibody trastuzumab bound to MDA-MB-453 cells demonstrating HER2 expression (FIG. 8A), while the anti-EGFR antibody cetuximab did not (FIG. 8B). Both Asp and iso-Asp EGFR p580 immune serum showed affinity for MDA-MB-453 cells by flow cytometry (FIG. 8B).

(v) Anti-Tumor Antibodies Elicited with EGFR p580 Inhibit Tumor Cell Growth and Promote ADCC The EGFR peptide antibodies induced by immunizing mice were evaluated for inhibition of human tumor cell growth with methods previously used to characterize cetuximab (Peipp M et al. (2008) Curr Opin Immunol 20:436-443; Yang X et al. (2013) Mol Ther 21:91-100). We examined tumor cell growth inhibition by incubating A431 cells with EGFR peptide immune sera for 48 h prior to the addition of 3H-thymidine. Cetuximab inhibited A431 cell growth by 42%. Asp p580 immune serum and iso-Asp p580 immune serum inhibited A431 growth at 1:25 dilutions (19% and 33%, respectively) (FIG. 9A).

We also found that the EGFR p580 antiserum inhibited the growth of MDA-MB-453 cells. Similar to the growth inhibition assays using A431 cells MDA-MB-453 cells were incubated with EGFR peptide antisera, as well as control monoclonal antibodies. Trazutuzmab (FIG. 9B) inhibited MDA-MB-453 cell growth by 27.5%, while Asp EGFR p580 antisera inhibited tumor cell growth by 50% and iso-Asp EGFR p580 inhibited tumor cell growth by 19% (FIG. 9B).

Figure 9C:
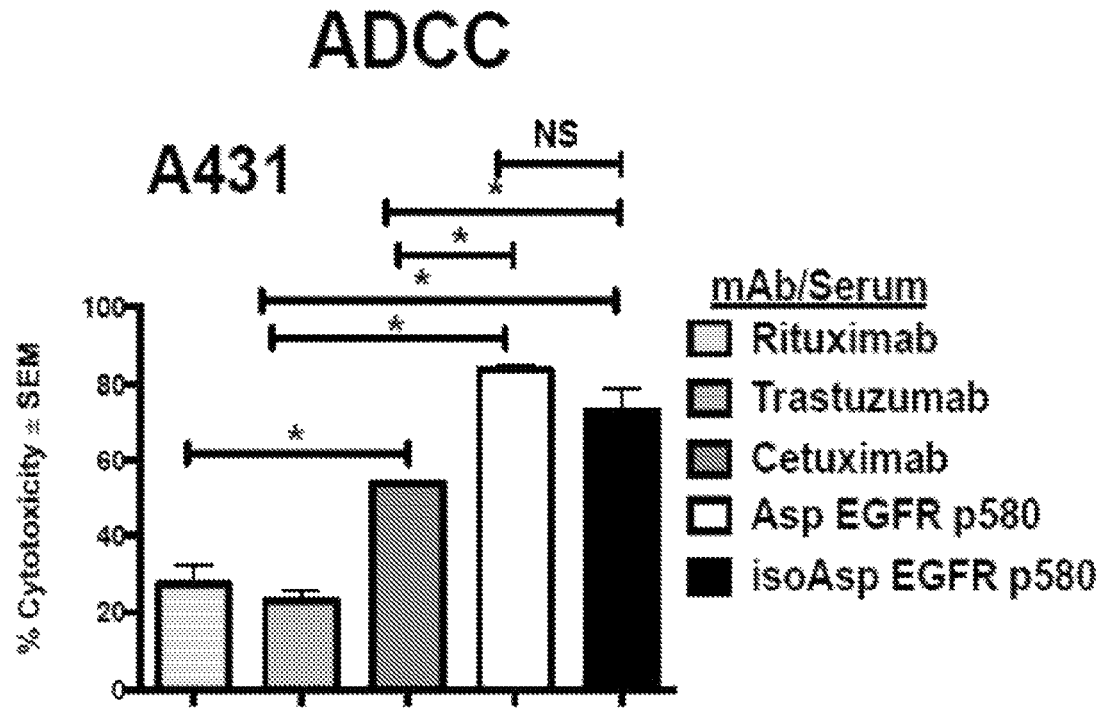
Figure 9D:
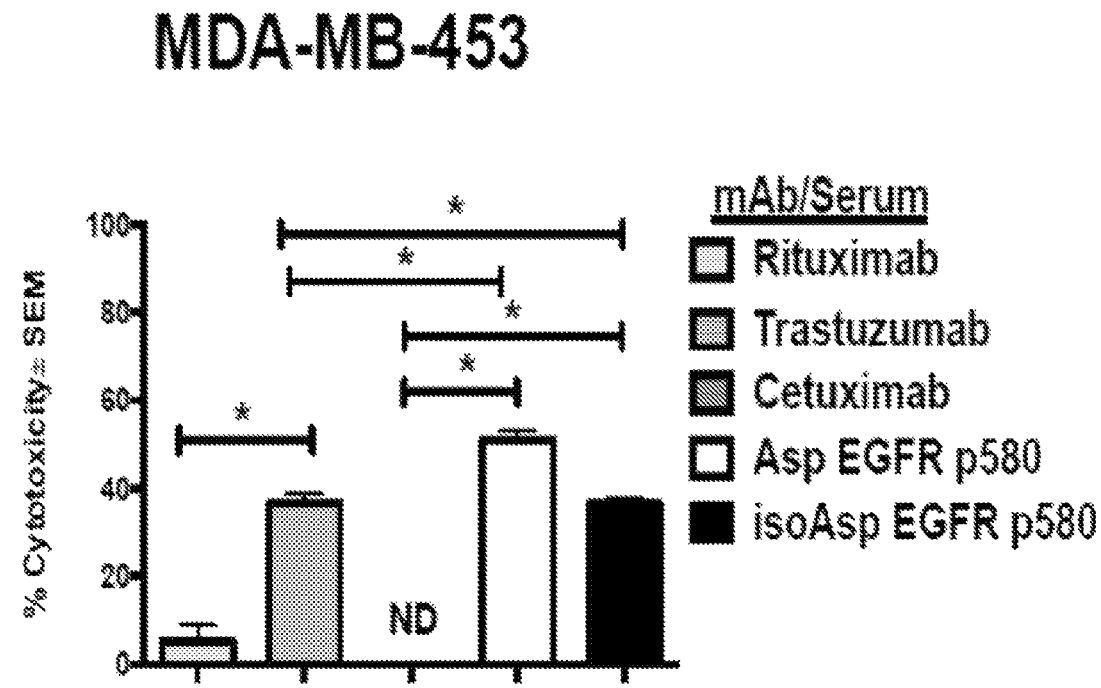

We next examined the ability of the immune sera to induce ADCC, one mechanism by which therapeutic monoclonal antibodies are assumed to function (Scott A M et al. (2012) 12:278-87). For this analysis, A431 cells were incubated with immune sera then incubated with human PBMC. As illustrated, the EGFR-specific monoclonal antibody cetuximab and antisera generated to either EGFR p580 isoform exhibited significant killing of A431 cells (FIG. 9C). As noted, even the polyclonal anti-EGFR p580 immune response superseded the cytotoxicity observed with the monoclonal anti-EGFR antibody, cetuximab. In a relatively similar manner, anti-EGFR p580 polyclonal sera significantly induced ADCC killing of HER2 expressing MDA-MB-453 human tumor cells as compared to the negative control antibody rituximab (FIG. 9D). As a positive control, trastuzumab triggered significant ADCC toward MDA-MB-453 cells as compared to rituximab while cetuximab failed to induce MDA-MB-453 cell killing (FIG. 9D).

(vi) EGFR Immunization Inhibits Tumor Growth In Vivo

Figure 10:
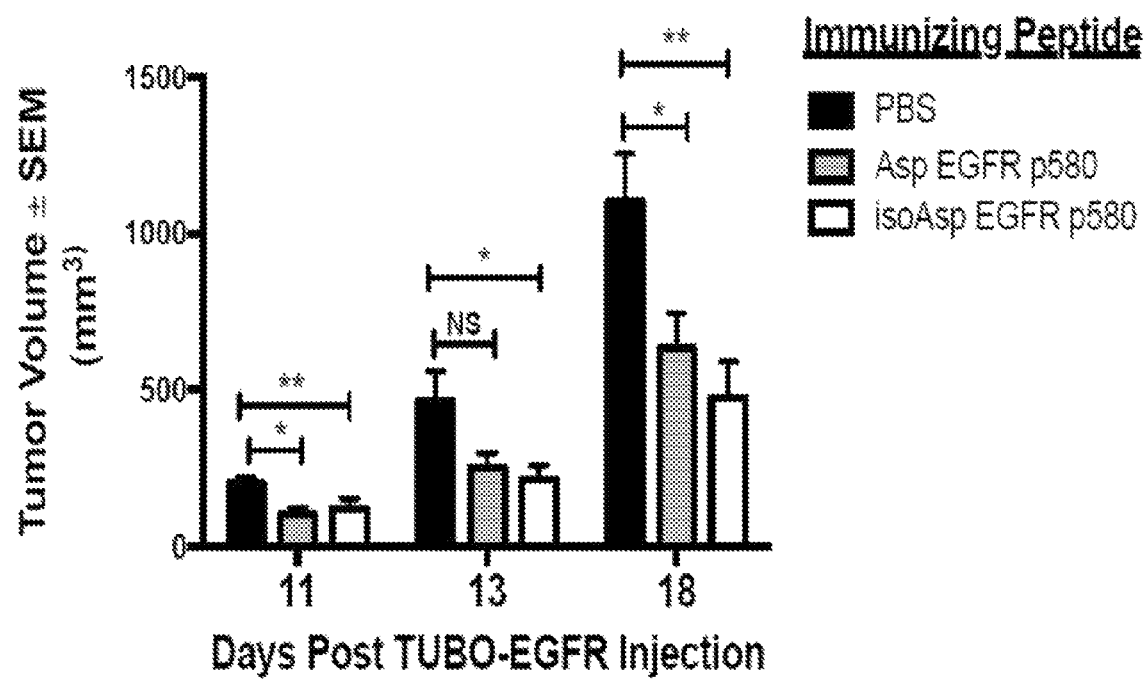
FIG. 10 is a graph showing tumor growth is inhibited in EGFR p580 immunized mice. Asp or isoAsp EGFR p580 immunized mice were injected s.c. with TUBO-EGFR cells. PBS-CFA injected mice served as controls. Tumors were measured and tumor volume calculated as described in the Materials and Methods (Example 2, A.(x)) on days 11, 13, and 18 post-injection. *, $p<0.05$; **, $p<0.01$; NS, not significant as determined by the Student t test. Results represent ten mice per group.
Figure 11:
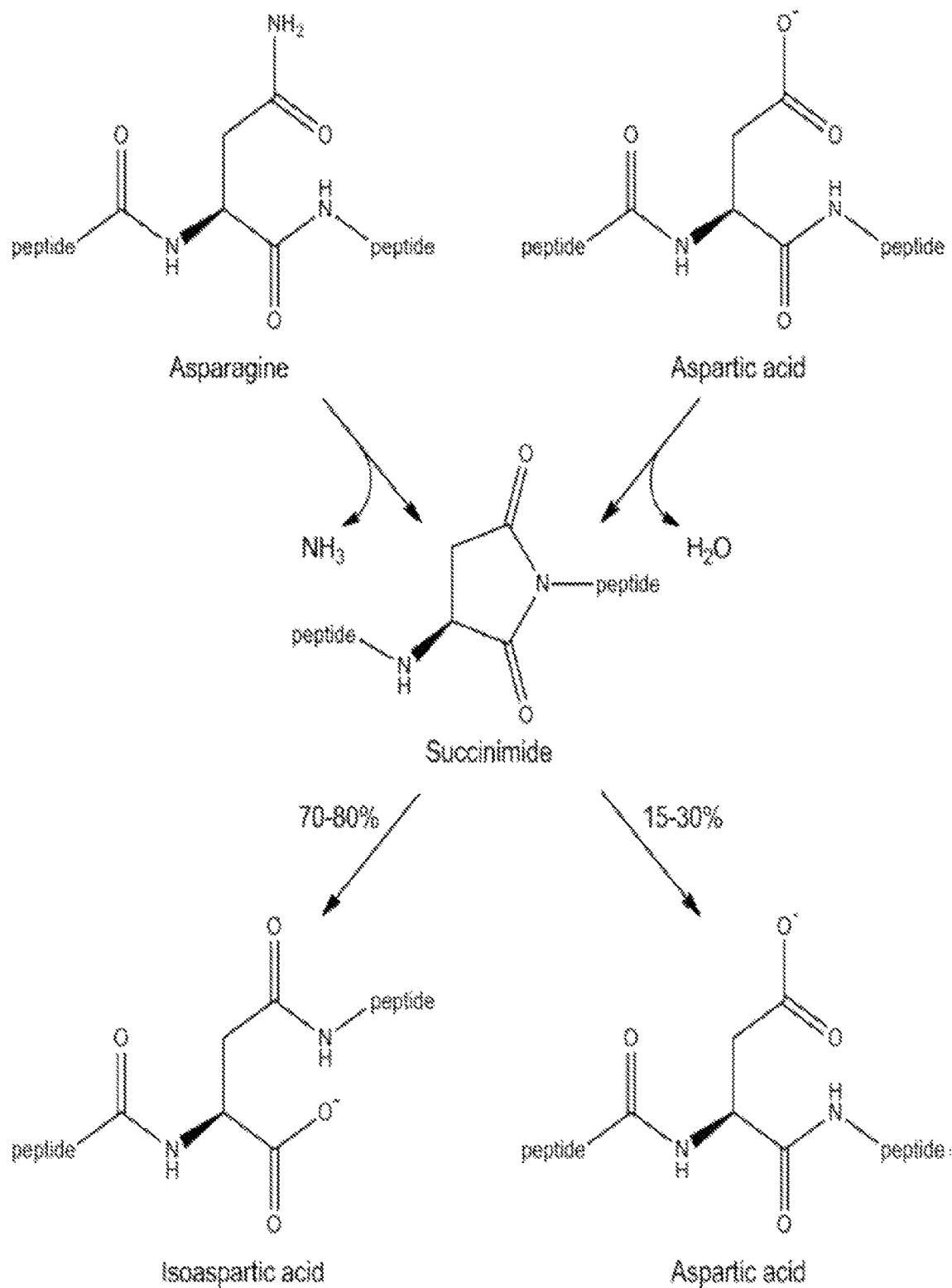
FIG. 11 is a diagram showing generation of isoaspartyl protein modification. Isoaspartyl modification spontaneously arises from aspartic acid or asparagine residues in proteins. As indicated, a succinimide intermediate is formed which, upon hydrolysis, most frequently leads to the isoaspartyl modification in the sequence. The modification arises at physiologic pH and temperature.

While immunization with the EGFR peptides elicited antibodies are capable of inhibiting tumor growth and mediating ADCC in vitro, we next examined if this immunization would be able to inhibit tumor growth in vivo. For these studies, we used the Balb/c derived TUBO cell line expressing human EGFR (TUBO-EGFR) (Yang X et al. (2013) Mol Ther 21:91-100). Asp or isoAsp EGFR p580 immunized mice were injected subcutaneously with TUBO-EGFR cells and their tumor size measured over a period of 18 days. Mice immunized with either Asp or isoAsp EGFR p580 had significantly smaller tumors as compared mice injected with adjuvant alone (PBS-CFA) on days 11, 13, and 18 (FIG. 10).

(vii) Discussion

One of the most successful advancements in cancer immunotherapy has been the development of monoclonal antibodies as immunotherapies against specific cancers (Scott A M et al. (2012) Nat Rev Cancer 12:278-87). Among the best established of these is the anti-HER2 monoclonal antibody trastuzumab (Herceptin®), approved for the treatment of HER2-positive breast cancer. Another member of the ErbB family, EGFR, is overexpressed in more than 30% of human cancers, including non-small lung cell carcinoma and colorectal cancer. Although there are monoclonal antibodies available for the treatment of EGFR-positive cancers (cetuximab and panitumumab) these treatments often provide only transitory effects and are cost-prohibitive to many within a global patient population (Fojo T et al. (2009) J Natl Cancer Inst 101:1044-8).

Specific, active immunotherapy with vaccines targeting tumor-associated antigens may reduce the need for prolonged administration of chemotherapy and therapeutic antibodies (Pol J et al. (2015) Oncoimmunology 4:e974411; Wiedermann U et al. (2013) Breast Cancer Res Treat 138:1-12). Cancer vaccines can potentially reduce side effects and provide immunologic memory to respond to tumor recurrence and metastases. Herein, we describe a novel peptide vaccine candidate that can target multiple members of the ErbB receptor family. As reported elsewhere, immunization with modified tumor peptides to break immune tolerance to tumor antigens remains an attractive therapeutic strategy (Mamula M J et al. (1999) J Biol Chem 274:22321-7; Doyle H A et al. (2006) J Biol Chem 281: 32676-83). We examined the immunogenicity and anti-tumor properties of aspartyl and isoaspartyl peptide isoforms derived from EGFR extracellular domain IV.

We initially designed five sets of EGFR peptides, each set having both the Asp and iso-Asp isoform of the peptide. These peptides are derived from a membrane-proximal region of the EGFR extracellular domain that is distinct from the epitopes recognized by cetuximab (FIG. 1A-1D) and panitumumab (Peipp M et al. (2008) Curr Opin Immunol 20:436-43). Mice immunized with these peptides all developed antibodies to the immunizing peptide. However, several peptides were unique in that they elicited antibodies that not only bound the immunizing peptides, but also bound to other ErbB family peptides with overlapping sequences. This was especially notable with the Asp and iso-Asp forms of the EGFR p580 sequence, which is identical in human and murine EGFR. These peptide immunizations circumvented immune self-tolerance to EGFR. They elicited high titer antibodies that cross-reacted with human EGFR and induced ADCC cell lysis and growth inhibition of human tumor cells in vitro. Moreover, no signs of aberrant tissue autoimmunity were observed in immunized mice over 10 months of observation.

In addition to eliciting antibody responses, EGFR p580 induced robust T cell responses. T cells from mice immunized with the iso-Asp isoform of p580 proliferated to a greater extent when exposed to the immunizing iso-Asp peptide as compared to T cells from mice immunized with the Asp isoform. The increased response of iso-Asp p580 reactive T cells to iso-Asp p580 may be a result of the iso-Asp residue altering how the peptide is processed (i.e., at a faster rate) or an alteration in the binding of the peptide to MHC class II. Both scenarios have been described for peptides with posttranslational modifications (Pritzker L B et al. (2000) Biochem 39:5374-81; Hill J A et al. (2003) J Immunol 171:538-41).

We next examined the ability of sera from immunized mice to bind intact human EGFR. The iso-Asp isoform of the EGFR p580 peptide elicits the strongest anti-peptide binding properties in vitro. We also found that iso-Asp EGFR p580 antibody bound to EGFR-expressing A431 tumor cells nearly 10-fold better than its Asp-isoform counterpart. Together, these data demonstrate that antibodies elicited by the mice immunized with p580 recognized intact EGFR molecules present on the surface of living human tumor cells. As predicted by EGFR extracellular domain crystal structures (Li S et al. (2005) Cancer Cell 7:301-11), the p580 sequence is surface exposed on the native EGFR protein, and accessible for anti-peptide antibodies (FIG. 1A-1D).

The ability of antibodies to inhibit tumor cell growth and trigger ADCC has been described in the analyses of other anti-EGFR antibodies (Peipp M et al. (2008) *Curr Opin Immunol* 20:436-43; Scott A M et al. (2012) *Nat Rev Cancer* 12:278-87). Interestingly, both Asp and iso-Asp EGFR p580 antisera inhibited A431 growth when tested at 1:25 serum dilutions. Similar to reported mechanisms for monoclonal antibody therapies, polyclonal antibodies elicited by EGFR p580 exhibited significant ADCC for both EGFR+ and EGFR−/HER2+ tumor targets, emphasizing the cross-binding properties of the immune response. Perhaps most important of all, is the fact that the antibodies elicited by EGFR immunization are able to inhibit the growth of EGFR expressing tumors in vivo (FIG. 10). The rapid growth of this transplantable tumor precludes long-term studies of vaccination efficacy.

Many tumors express EGFR and another member of the ErbB receptor family. HER2 and/or HER3 are often co-expressed with EGFR in colorectal and breast cancers (Beji A et al. (2012) *Clin Cancer Res* 18:956-68; Kavuri S M et al. (2015) *Cancer Discov* 5:832-41; Takegawa N et al. (2015) *Oncotarget* 7:3453-60). The appeal of this EGFR peptide immunization strategy is that it circumvents self-tolerance to EGFR and the resulting anti-peptide antibodies cross-react with human EGFR, HER2 and HER3. The iso-Asp EGFR p580 peptide shares 58%, 68% and 53% sequence identity with corresponding regions of human HER2, HER3 and HER4, respectively (Table 1). These regions potentially contribute to the regulation of the receptor tyrosine kinases. The domain IV regions corresponding to p580 interact with domain II in the EGFR and HER3 tethered conformations, are adjacent to the EGFR dimer domain IV-domain IV interface, and overlap with the HER2 trastuzumab epitope (FIG. 1A-1D).

Patients with a therapeutic response to anti-EGFR monoclonal antibodies as a first line of therapy often develop resistance to the antibody and subsequent tumor progression (Cunningham D et al. (2004) *N Engl J Med* 351:337-45; Van Cutsem E et al. (2007) *J Clin Oncol* 25:1658-64). Acquired tumor resistance to cetuximab is the result of a number of mechanism including mutations in V-Ki-ras2 Kirsten rat sarcoma viral oncogene homolog (KRAS), B-Raf protooncogene (BRAF), PI3K (Kruser T J et al. (2010) *Exp Cell Res* 316:1083-100), and EGFR (Montagut C et al. (2012) *Nat Med* 18:221-3), amplifications of KRAS, and altered regulation of EGFR, VEGF/VEGFR and the Met proto-oncogene (MET) (Brand T M et al. (2011) *Cancer Biol Ther* 11:777-92; Van Emburgh B O et al. (2014) *Mol Oncol* 8:1084-94). Relative to the present study, resistance also can arise when other ErbB family members (HER2, HER3, HER4) compensate for the signaling loss of EGFR, triggering tumor outgrowth (Wheeler D L et al. (2008) *Oncogene* 27:3944-56; Yonesaka K et al. (2011) *Sci Transl Med* 3:99ra86). ErbB family members form heterodimers with each other, thus forming several signaling pathways that compensate for loss of EGFR. Thus, targeting two or more members of the ErbB family simultaneously is a strategy to overcome antibody resistance. In pancreatic carcinoma xenograft models targeting EGFR and HER2 simultaneously with cetuximab and trastuzumab was a more effective treatment than a combination of trastuzumab and erlotinib (an EGFR tyrosine kinase inhibitor) or even lapatinib alone (an irreversible dual EGFR/HER2 tyrosine kinase inhibitor) (Larbouret C et al. (2012) *Neoplasia* 14:121-30). These results were attributed to disrupted EGFR/HER2 heterodimerization, receptor down-regulation and/or decreased Akt phosphorylation. The dual specificity monoclonal antibody MEHD7945A targets both EGFR and HER3, decreases Akt phosphorylation, and inhibits tumor cell growth better than monospecific antibodies or tyrosine kinase inhibitors (Schaefer G et al. (2011) *Cancer Cell* 20:472-86; Huang S M et al. (2013) *Cancer Res* 73:824-33). It is noted that MEHD7945A as well as another dual specificity antibody that binds both HER2 and VEGF (Bostrom J et al. (2009) *Science* 323:1610-4) were developed by genetic engineering and did not result from a natural immunization process as in our study.

Finally, active immunization with p580 or other EGFR peptides (Foy K C et al. (2013) *J Immunol* 191:217-27; Ebben J D et al. (2015) *Mol Carcinog* doi 10.1002/mc22405) could also be used in conjunction with current passive immunotherapies, such as cetuximab or trastuzumab, with the hopes of combining the benefits of active and passive immunotherapies. Multiple therapeutic combinations have been tried with success in recent years to enhance the benefit of cetuximab treatment (Ramalingam S et al. (2008) *J Thorac Oncol* 3:258-64; Regales L et al. (2009) *J Clin Invest* 119:3000-10; Bertotti A et al. (2015) *Nature* 526:263-7). Our data clearly shows the ability of EGFR immunization to inhibit tumor growth, and combined with other immunotherapies, has the potential for synergistic tumor inhibition. It also has the added benefit of targeting several ErbB family members thus mimicking the effect of multiple therapeutic monoclonal antibody combinations.

Example 3: EGFR Immunity in Spontaneous Canine Cancer

A. Methods
(i) Canine Studies

Canine 'patients' will be privately owned animals seeking treatment at our IACUC approved facility, the Veterinary Cancer Center, Norwalk, CT. Dogs will be first assessed for tumor type (Table 3). With consent of owners, animals will be immunized and boosted with canine EGFR p553 peptide (SEQ ID NO: 15) emulsified in adjuvant (IFA+LymeVax, or Montanide ISA51 VG). Antibody responses to self (canine) EGFR will be evaluated. Anti-tumor peptide and protein binding will be evaluated by ELISAs with EGFR peptides and by flow cytometry with EGFR-expressing canine cells. We will also assess binding to related ErbB proteins, HER2 and HER3. Finally, we will assess peripheral T cell immunity to EGFR p533 peptide from immunized canine patients. ISA51 VG triggered more vigorous anti-tumor antibodies in murine recipients.

(ii) Peptide Preparation

Peptides will be synthesized and purified by a commercial vendor (GenScript) similar to that utilized in pilot studies (>95% purity and verified by both HPLC and mass spectrometry) and tested for endotoxin and sterility. The synthetic EGFR p553 peptide is based on canine EGFR residues 553-598 (IKCAHYIDGPHCVKTCPAG) (SEQ ID NO: 15). The peptide does not have extensive homology to canine proteins outside of the ErbB family. The peptide includes conserved, surface exposed residues of ErbB proteins (Table 1, FIG. 1A-1D). It is important to note that the entire p553 EGFR sequence is 95% identical between dogs and man. Thus, immunity in dogs is directly relevant to breaking immune tolerance in humans (which can be easily confirmed by antibody binding to human EGFR).

(iii) IACUC Protocol and Immunization of Animals

Dogs with a projected lifespan of >12 weeks and with EGFR positive tumors (Table 3) will be identified at The Veterinary Cancer Center (VCC) of Norwalk, CT. The present study will enroll statistically significant numbers of canine cancer subjects with presumed or known ErbB family tumors. The present study will be performed on both male and female canine patients of all ages and all breeds. Patient numbers are chosen to obtain statistical significance for vaccine responses (>4-fold increases in antibody titer) based on prior studies in canine vaccine models and as published criteria for comparative oncology in canine hosts (Wang C Y et al. (2005) *Vaccine* 23:2049-56; Kawai R et al. (2013) *J Toxicol Sci* 38:571-9; Langeveld J P et al. (1994) *J Virol* 68:4506-13; Burton J et al. (2014) *Vet Clin Small Anim* 44:977-987; Thamm D H et al. (2015) *Vet J* 205:226-232).

In brief, a minimum of 7 animals per immunization group will allow for statistical significance. The totals indicated here include small numbers of animals, that may not survive the entire course of therapy or may whose owners may remove their animals from the study. Animals immunized at the start of the award will be examined as indicated below. The veterinary oncologist will randomly assign animals to the experimental or control groups. For these studies, canine patients will be enrolled without regard to breed, age, or gender, but will have confirmed evidence of the presence of EGFR/HER2 tumors based on standard laboratory histochemistry.

Based on titration studies in murine models, dogs (10 per group) will be vaccinated with a single dose of EGFR p553 (2 mg/kg) emulsified in Montanide ISA51VG with an equal volume of canine LymeVax (Zoetis, Inc.) for a total 0.2 cc subcutaneous injection at day 0 and day 21. The present adjuvant (Montanide ISA51VG) is chosen to study antibodies to Lyme disease antigens in parallel with anti-EGFR antibodies. This design allows assessment of two target antigens (Lyme and EGFR) to determine if a lack of response may be due to immune compromised animals (and/or immune tolerance to the self EGFR peptide). Additional groups of ten canine patients will be immunized with other commercially available adjuvants utilized in either human or veterinary formulations (including alum). From the Clinical Trials database, Montanide ISA51 VG has been utilized in human cancer immunization clinical trials, including melanoma (MART-1, Tyrosinase, GP100, MAGE, NY-ESO-1), as well as hepatocellular carcinoma, bladder and breast cancer, sarcoma, prostate and ovarian cancers (Clinical Trials database: clinical trial NCT00112242, clinical trial NCT01012102, clinical trial NCT00935545, clinical trial NCT00299728). Sera will be collected prior to vaccination (day 0), prior to boost (day 21), day 28 and on day 50-60 post-immunization and tested for antibodies against the immunizing peptide.

(iv) Antibody and CD4 T Cell Analyses

EGFR p553 antisera will be evaluated for antibody binding to the EGFR p553 epitope and highly homologous regions of HER2. As noted elsewhere, polyclonal antibodies from murine models are often cross-reactive at this site among EGFR, HER2, and HER3. These ErbB family members are frequently co-expressed on a variety of human, canine, and murine tumor types. Thus, we will also assess the ability of antibodies in EGFR p553 preimmune and immune canine sera to bind recombinant human and canine extracellular domains of EGFR, HER2 and HER3 (commercially available; R&D Systems). Antibody binding will be assessed by conventional ELISA, as illustrated in FIGS. 4, 6, 9, 14, 15, 19, 22. The immunization will be regarded as efficacious if >4 fold titers are found over pre-immune serum signals in individual animals. We will also seek to match or exceed those titers found with murine EGFR p580 in mouse models or match those binding features of standard therapeutic mAbs (cetuximab and/or trastuzumab). CD4 T cell responses will be assessed by conventional proliferation assays towards EGFR peptide (and control peptides) as previously published (Mamula M J et al. (1999) *J. Biol. Chem* 274: 22321-7). In brief, $10^5$ PBMCs from canine patients (both pre- and post immune samples) will be incubated with titrations of EGFR p553 or scrambled peptide sequence control for 48h.

Proliferation will be assessed with $^3$H-thymidine for the last 18h of culture.

(v) Adverse Events in EGFR Targeted Therapies

An inherent risk to immunizing with a self-peptide is in the generation of autoimmune pathology. Initially, all dogs will be monitored for any signs of gross skin changes (fur loss, rash), as skin toxicities are the primary complication to Erbitux treatments (Li S et al. (2009) *Target Oncol.* 4:107-119). Dogs will be weighed prior to immunization and monitored for weight loss, a symptom that could be an indication of autoimmune pathology, as well as monitoring for signs of diarrhea (another complication of EGFR treatment). Should signs of skin toxicity be found in our EGFR peptide immunized dogs, we will follow guidelines set forth in standard veterinary practice, similar to that of human clinical care (Pothoff K et al. (2011) *Ann Oncol* 22:524-535, Pinta F et al. (2014) *Clin Colorectal Cancer* 13:62-7). Liver function (LFTs) and kidney function (urinalysis) will be performed pre and post vaccination as well pathology of suspected skin lesions. Finally, pathology (IHC and H&E) will be performed when biopsy or necropsy tissues are obtained.

Based on our pilot studies of EGFR peptide immunizations in mice and now in limited numbers of dogs, a robust antibody response in dogs vaccinated with canine EGFR p533 (see FIGS. 12-16) was detected. Should we see low titers of antibody, additional dosing and/or adjuvant scheme will be assessed. We observed minimal side effects beyond those seen with other canine vaccines. Mice in our laboratory have been immunized for over 10-12 months with murine EGFR peptide with no loss of fur or skin pathology.

(vi) EGFR-Bearing Tumor Cell Growth Inhibition

We will assess the ability of antibodies to bind and to kill canine and human EGFR-bearing tumor cells in flow cytometry, by antibody-dependent cellular cytotoxicity (ADCC) and inhibition of tumor cell growth in vitro. Negative controls will include matched preimmune sera, EGFR−HER2− cells, and sera from sham-immunized patients. Where possible, tumor samples from EGFR immune animals will be examined by immunohistochemistry for canine antibody and T cell deposition.

(vi) Binding of Native EGFR on Canine Tumor Cells by Peptide Immune Sera

To determine if EGFR p553 immune sera binds intact canine EGFR, we will perform flow cytometry on canine D17 mammary tumor cells (ATCC CLF-6232), which are known to express EGFR (Singer J et al. (2012) *Mol Immunol* 50:200-9), that have been incubated with preimmune or immune sera, in addition to cetuximab (positive control). We will also perform flow cytometry staining on human A431 cells that overexpress EGFR as another control. As our previous data have demonstrated that immunization with murine EGFR p580 in mice elicits antibodies that also bind HER2, we will also perform flow cytometry on human MDA-MB-453 cells (ATCC HTB-131; HER2+ EGFR−) to determine if the antibodies elicited by canine EGFR p533 also bind to HER2. Cetuximab and trastuzumab will serve as additional positive control antibodies, in that they both bind canine D17 and human EGFR and HER2, respectively (Singer J et al. (2012) *Mol Immunol* 50:200-9).
(vii) In Vitro Tumor Growth Inhibition and ADCC Tumor Killing with EGFR p553 Immune Serum.

We will determine if canine EGFR p553 immune serum inhibits the growth of EGFR using the canine cell line D17. Briefly, tumor cells (1000 cells/well) will be plated in 96-well plates overnight. The following day, cells will be treated with cetuximab or titrating dilutions of EGFR p553 preimmune or immune canine serum (Schaefer G et al. (2011) *Cancer Cell* 20:472-86). After 3 days, cells will be pulsed with $^3$H-thymidine and harvested 18 h later.

Monoclonal antibodies often mediate their anti-tumor effects through antibody-dependent cell-mediated cytotoxicity (ADCC) (Juntilla T T et al. (2010) *Cancer Res* 70:4481-9; Taylor R J et al. (2009) *Cancer Immunol Immunother* 58:997-1006; Robak T (2009) *Curr Opin Investig Drug* 10:588-96). We will test the ability of our EGFR p553 immune sera to mediate ADCC using both D17 cells and A431 cells. Cells will be incubated with freshly isolated canine PBMC along with titrating concentrations of cetuximab, rituximab (negative control) or EGFR p553 preimmune or immune sera. ADCC will be determined by measuring lactate dehydrogenase (LDH) release in supernatants with a commercially available kit (Promega). Should we also see HER2 binding with the canine immune sera, we will also perform growth inhibition and ADCC assays using MDA-MB-453 cells as targets and trastuzumab (human anti-HER2 mAb, Herceptin) as a positive control.
(ix) Morphologic and Immunohistochemical Analysis of Tumor Should euthanasia be requested by the dog's owners due to morbidity or the loss of quality of life, pathology will be performed on the primary tumor samples, any metastatic sites, as well as the vaccination site (again, with owner consent). The following antibodies will be used: anti-CD4, anti-CD8a, anti-CD11b, anti-B220 (AbD Serotec), anti-EGFR mAb (Abcam), Erbitux (Oncogene Research Products). Samples are also stained with conventional H&E. Images will be acquired and analyzed by both fluorescent and by confocal microscopy. Immunohistochemistry is an established technology in our laboratory. These studies will allow for the analysis of T and B cell subsets or tumor specific Ab or complement deposition in tumor masses. Similarly, we will allow owners from untreated animals to be consented for acquisition of tumor tissues to serve as negative controls in this study.

To better characterize anti-tumor immune responses in immunized canine patients, we will assess whether antibodies from immune sera bind to native canine EGFR and promote anti-tumor activities, such as growth inhibition and tumor killing. While there may be a lack of established canine tumor cells that express only EGFR or only HER2, we believe the homology between the human and canine EGFR and HER2 should allow us appropriate assessment. Minimal biological activity (low titers) may suggest that we need to utilize an alternate peptide sequence and/or dosing regime. Tumors from vaccinated, sham vaccinated and untreated control animals will allow us to determine a baseline of antibody binding and cellular infiltration of native tumors. We do realize that outbred animals of different breeds will understandably reveal slightly different phenotypes (tumor size, other potential pathologies, etc).

B. Results

Companion animals, such as dogs, also develop tumors that express EGFR (Table 3). Studies have demonstrated that high expression of EGFR in canine cancers such as lung cancer and osteosarcoma are correlated with shortened survival times (Selvarajah G T et al. (2012) *Vet J* 193:412-9; Sabattini S et al. (2012) *Vet Comp Onco* doi: 10.1111/vco.12002). The present studies will examine efficacy of EGFR peptide immunization in canine tumor-bearing patients. The canine cancer population is ideal at the present stage of therapeutic development, in providing an outbred, heterogeneous population of EGFR-bearing tumor recipients that resemble human disease (Wang C Y et al. (2005) *Vaccine* 23:2049-56; Kawai R et al. (2013) *J Toxicol Sci* 38:571-9; Langeveld J P et al. (1994) *J Virol* 68:4506-13; Burton J et al. (2014) *Vet Clin Small Anim* 44:977-987).

TABLE 3

Canine Tumors Expressing ErbB Family Members

| Tumor | ErbB Expression | Reference |
|---|---|---|
| Mammary carcinoma | EGFR, HER2 | (1) |
| Pituitary Adenoma | EGFR | (9) |
| Osteosarcoma | EGFR, HER2 | (10, 11) |
| Glioma | EGFR | (12) |
| Hemangiosarcoma | EGFR | (13) |
| Lung | EGFR | (14) |
| Epithelial Nasal | EGFR | (15) |

(1) = Singer J et al. (2012) *Mol Immunol* 50:200-9;
(9) = Fukuoka H et al. (2011) *J Clin Invest* 121:4712-21;
(10) = Selvarajah GT et al. (2012) *Vet J* 193:412-9;
(11) = Flint AF et al. (2004) *Vet Pathol* 41:291-6;
(12) = Higgins RJ et al. (2010) *J Neurooncol* 98:49-55;
(13) = Schappa JT et al. (2013) *Int J Cancer* 133:1936-44;
(14) = Sabattini S et al. (2012) *Vet Comp Onco* doi: 10.1111/vco.12002;
(15) = Shiomitsu K et al. (2009) *Vet Comp Onco* 7:106-14.

(i) EGFR p580 Epitope.

Our laboratory has demonstrated that both cryptic self peptides and/or posttranslational protein modifications of self peptide often break immune tolerance to self-peptides as well as tumor antigens (Doyle H A et al. (2006) *J Biol Chem* 281: 32676-83; Mamula M J et al. (1999) *J. Biol. Chem* 274: 22321-7). As described herein, EGFR and HER2 peptide vaccination experiments identified cryptic peptides that can also break immune tolerance in mice. In studies illustrated below, mice immunized with EGFR peptide p580-598 developed antibodies that recognize native EGFR, inhibit tumor cell growth and promote ADCC tumor cell killing. These antibodies also recognize other members of the ErbB family, including HER2 and HER3, and inhibit growth of HER2+ tumor cells. More importantly, these antibodies are also capable of inhibiting the growth of HER2 positive, EGFR negative tumor cells. Thus, this immunization strategy could be used to develop a therapeutic cancer vaccine to target multiple proteins of ErbB family expressed on the same tumor. The innovation of this strategy is that the resulting antibodies have specificity for homologous regions of both HER2 and HER3 in addition to EGFR (Table 1). Various tumors, (colorectal and breast cancer) express EGFR and another member of the ErbB family, e.g., HER2 and/or HER3 (Rowinsky E K (2004) *Annu Rev Med* 55: 433-57; Beji A et al. (2012) *Clin Cancer Res* 18: 956-68). Finally, we have initiated a clinical trial in spontaneous canine (pet) cancers with the Veterinary Cancer Center (Norwalk, CT). Herein, we present data showing that dogs elicit strong IgM and IgG anti-tumor antibodies, even after 3 weeks of EGFR p533 (SEQ ID NO: 15) immunization.

(ii) The p580 Epitope is Part of the Domain IV Region that Regulates Activity of ErbB Receptors.

The structure, function and conserved sequences of the p580 epitope in the native EGFR protein confirm that it is a potential therapeutic cancer vaccine target in EGFR, HER2, and HER3 (Tables 1 and 4). In crystal structures of the extracellular domains of EGFR, HER2, HER3 and HER4, this epitope is constrained and structurally conserved. In EGFR, HER3 and HER4, this region functions as part of the interdomain interface between domains II and IV that maintains these receptors in an inactive, tethered conformation (e.g., FIG. 1A-1D).

Trastuzumab (Herceptin), which is not cross-reactive, recognizes a conformational HER2 epitope that includes residues homologous to a segment of the EGFR p580 epitope. The HER2 domain II dimerization arm targeted by pertuzumab corresponds to the HER2 domain II region that interacts with the p580 epitope region in domain IV.

TABLE 4

Sequence of canine EGFR p553 and the corresponding sequence in human and murine EGFR. Bold letters indicate amino acid differences between species.

| | |
|---|---|
| Human p580-598 | IQCAHYIDGPHCVKTCPAG (SEQ ID NO: 1) |
| Mouse p580-598 | IQCAHYIDGPHCVKTCPAG (same as (SEQ ID NO: 1)) |
| Canine p553-571 | IKCAHYIDGPHCVKTCPAG (SEQ ID NO: 15) |

(iii) Cross-Reactive Immunization Approach May Limit Development of Recurrent Tumors that are Resistant to Immunotherapy.

Approximately 20-30% of high-grade gliomas (GBM) express EGFRvIII with constitutively activated tyrosine kinase activity (Gan H K et al. (2009) *J Clin Neurosci* 16: 748-54). This tumor-specific EGFR variant has been associated with resistance to cetuximab. Rindopepimut, a 13-amino acid EGFRvIII specific peptide conjugated to KLH, was examined in Phase III glioblastoma clinical trials (Babu R et al. (2012) *Core Evid* 7: 93-103). Although it targets the tumor-specific EGFRvIII, its efficacy can be limited by loss of the mutant EGFRvIII in patients (Heimberger A B et al. (2009) *Expert Opin Biol Ther* 9: 1087-98). These clinical features suggest that the p580 vaccine strategy targeting EGFR, HER2 and HER3 may provide more efficacious therapy.

Data presented supra demonstrated the efficacy of murine EGFR p580 peptide immunization, and that the resulting antibodies cross-reacted with homologous sequences from EGFR, HER2 and HER3. The EGFR p580 antibodies are capable of inhibiting the growth of both EGFR overexpressing cells and EGFR-negative, HER2-positive tumor cells. We herein present data from a study initiated in spontaneous canine cancer, performed at the Veterinary Cancer Center, Norwalk, CT. Twenty-eight (28) dogs with EGFR expressing cancers (e.g., cancers listed in Table 3) have been immunized with the homologous canine EGFR p553 peptide (various breeds, age and gender). Serum samples from 18 animals were examined 3 weeks post vaccination (at the time of the booster vaccination). Fourteen (77%) of animals show IgM and IgG anti-EGFR antibodies at 3 weeks post vaccination all of which bind EGFR expressing A431 tumor cells and HER2 expressing MDA-MB-453 cells. The remaining 10 animals await booster immunizations. The study was initiated and carefully evaluated in murine models described below, including examination of various peptide sequences, formulations, and adjuvants.

(iv) Murine EGFR p580 Immunization Elicits Mouse Antibodies that Bind and Inhibit the Growth of Tumor Cells In Vivo and In Vitro.

See section Example 2, B.(iv)-(vi), supra.

Figure 17:
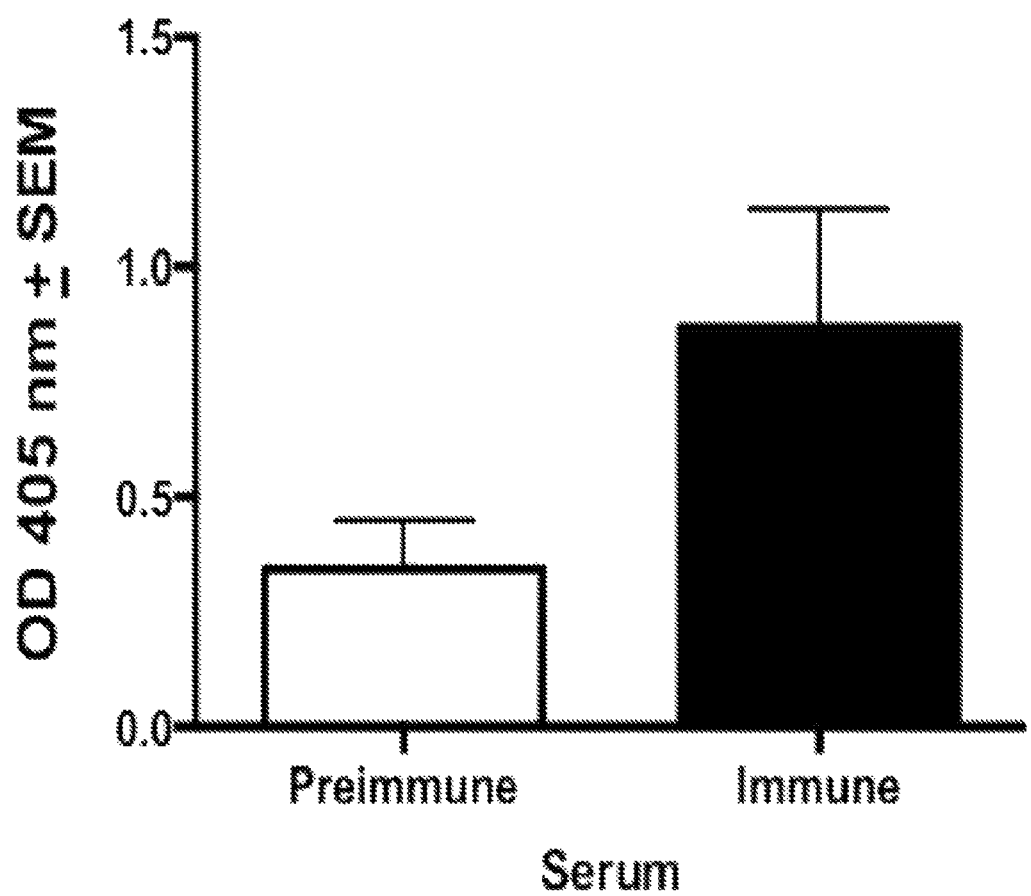
FIG. 17 is a graph showing EGFR p553 immunized dog cancer patients make IgG antibodies that bind canine EGFR p553. Serum of immune animals, examined at the time of booster immunization (3 weeks) were tested for IgG anti-EGFR p553 ($p<0.01$).

(v) Canine EGFR p553 (SEQ ID NO: 15) Immunization of Dogs with Spontaneous EGFR+ Tumors Elicits Anti-Tumor Antibodies Immunizations of spontaneous canine cancer bearing animals have been initiated at the Veterinary Cancer Center, Norwalk, CT. Twenty eight (28) dogs have received primary immunization (100 µg canine p553 co-mixed with canine LymeVax/IFA). Eighteen animals have received booster immunization at day 21 (in a manner similar to murine studies). As noted in the approved protocol, serum samples are obtained at day 0 (pre-immune); day 21 (the time of booster immunization), at day 28, and at day 60. We have now performed analysis on 18 samples obtained at day 28. As shown in FIG. 17, ELISAs with canine EGFR p553 antigen demonstrated 'patients' had significant increases in anti-EGFR p553 IgG titers compared to pre-immune sera. Those sera that were positive for IgG also have IgM anti-EGFR p553 (not shown). Remarkably, virtually all reactive sera were also positive at day 21 (prior to the booster vaccination) though titers increase by day 28 (not shown).

Figure 18:
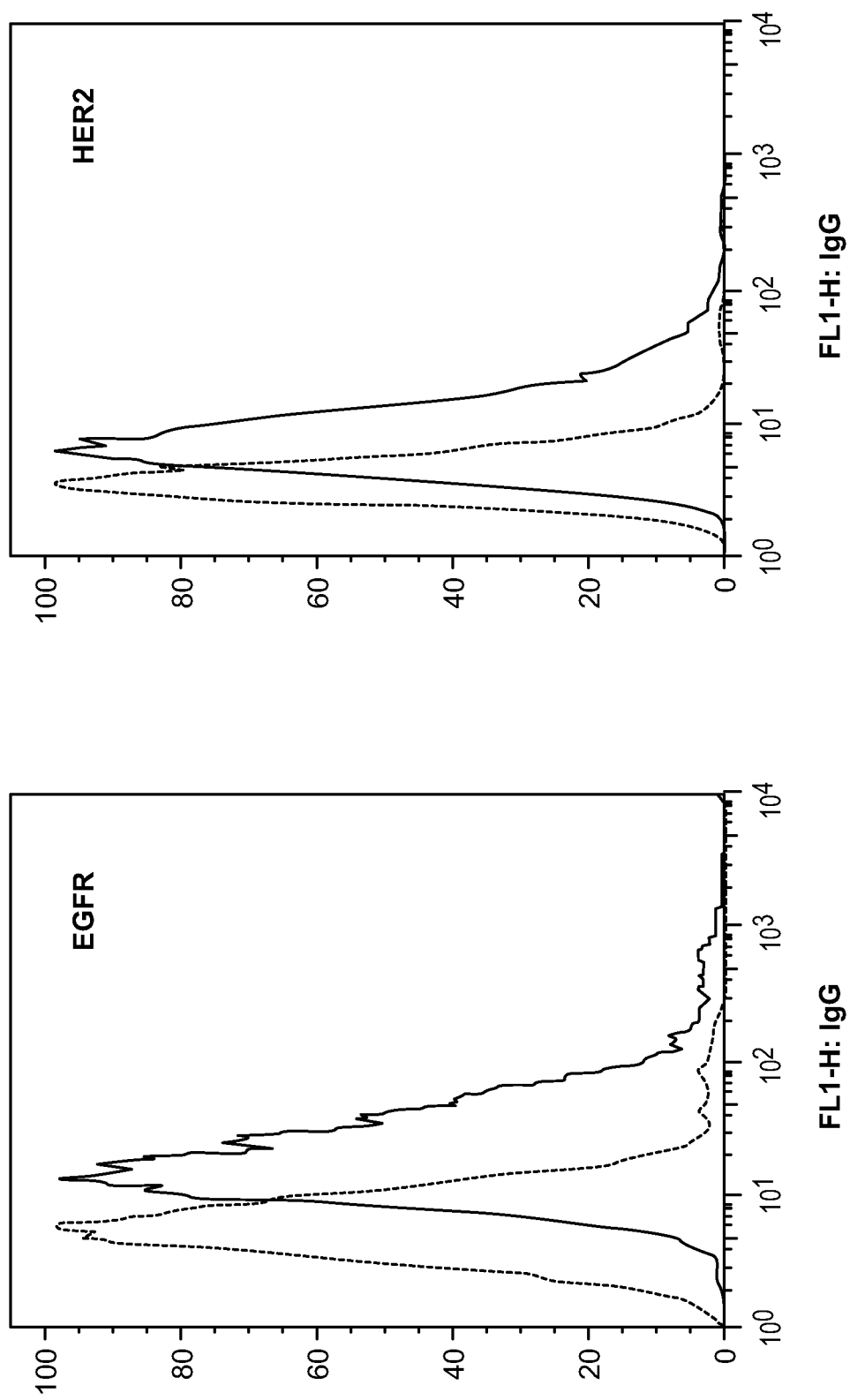
FIG. 18 are graphs showing EGFR p553 immunized dog cancer patients make antibodies that bind EGFR+ and HER2+ tumor cells.
Figure 19:
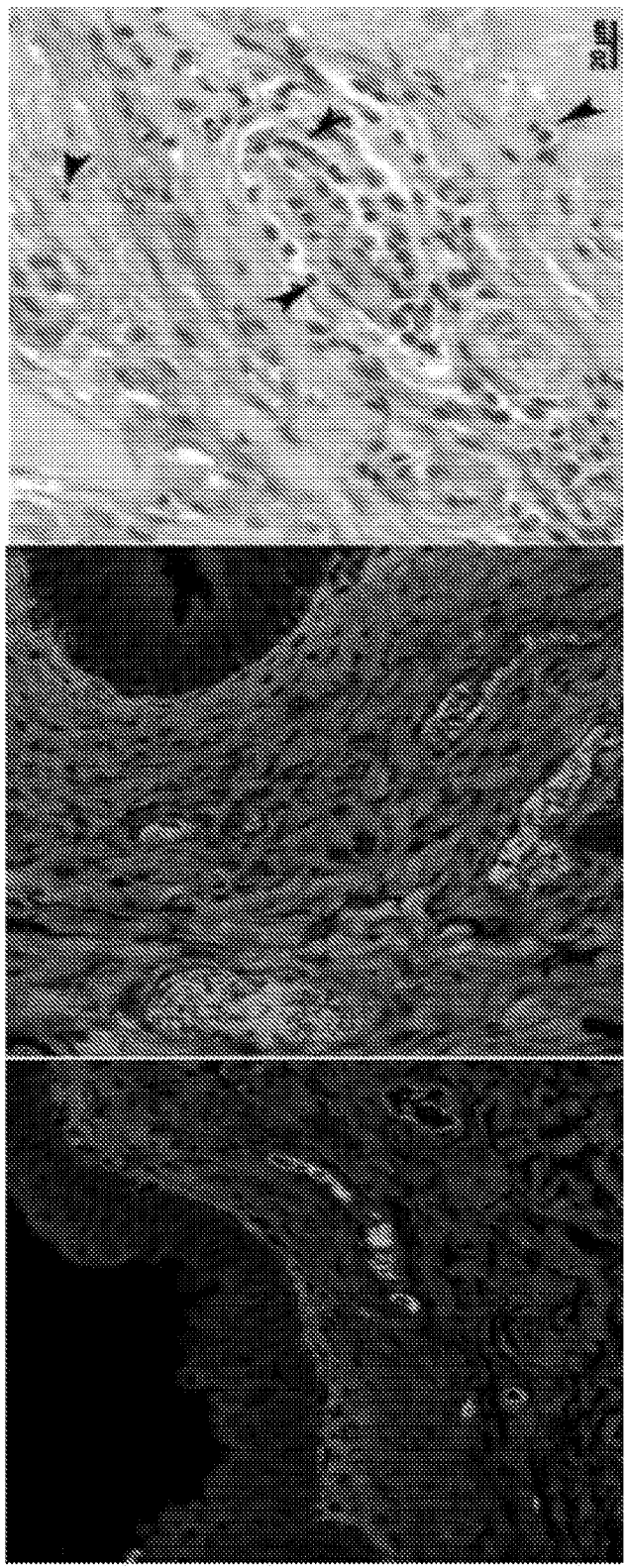
FIG. 19 are photographs showing EGFR p553 immunized dog cancer patients make antibodies and T cells that infiltrate tumors. Histochemistry of one canine patient with EGFR+ bladder cancer. Left panel: normal bladder IgG deposition. Middle panel: IgG deposition from the bladder tumor site. Right panel: arrows represent T cell infiltration into the tumor site.

Representative positive sera from dogs were examined by flow cytometry. FIG. 18 demonstrates that the canine EGFR p553 immune serum binds to both EGFR$^+$ A431 and to HER2+MDA-MB-453 tumor cells. In summary, we now have demonstrated that the peptide formulation and specificity elicit antibodies that bind both the immunogen as well as native protein expressed on live tumor cells. To date, no animals have demonstrated significant untoward effects of the immunization and none have withdrawn from the study. We have observed mild inflammation at the site of injection (3 of 18 animals) that typically resolves within 14 days.

To develop a safe and effective peptide-based immunization that can induce tumor regression in dogs with EGFR bearing tumors, candidate EGFR peptide vaccine/adjuvant combinations that can overcome immune tolerance to self-EGFR in canine cancer 'patients' have been identified. The adjuvants used herein include those presently utilized in human therapeutics and human clinical trials (Montanide ISA 51 VG) as compared to canine LymeVax/oil emulsion (both of which trigger anti-tumor Abs in murine models).

Figure 12:
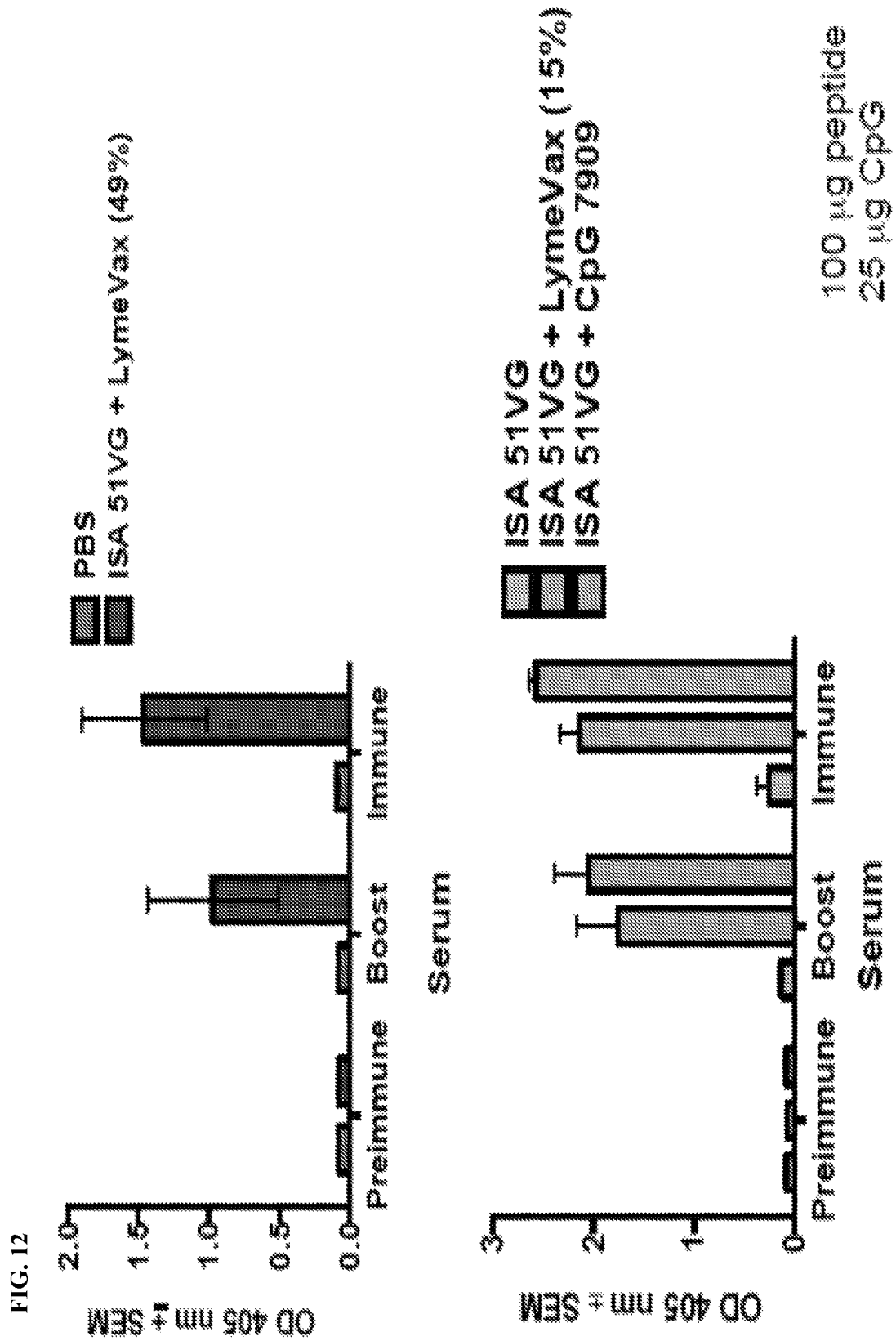
FIG. 12 is a graph depicting that TLR stimulant is important in boosting immune responses to the canine EGFR p553 peptide.

The canine EGFR peptide sequence [canine cEGFR p553 (SEQ ID NO: 15)] was first examined as a vaccine in murine immune responses. For these studies, pharmaceutical compositions where formulated using 100 pg of canine cEGFR p553 (SEQ ID NO: 15) combined with the following adjuvants, Montanide ISA 51VG (50%), LymeVax (15% or 49%) or CpG 7909 (25 pg). Mice were immunized at day 0, and day 21. Serum was obtained from mice at day 0 (preimmune) and at day 28 (immune) and analyzed by ELISA for binding to the canine EGFR (canine cEGFR p553 (SEQ ID NO: 15) as illustrated in FIG. 17. As depicted in FIG. 12, a toll-like receptor (TLR) stimulant is important in boosting immune responses in mice to the canine EGFR p553 peptide.

Figure 13:
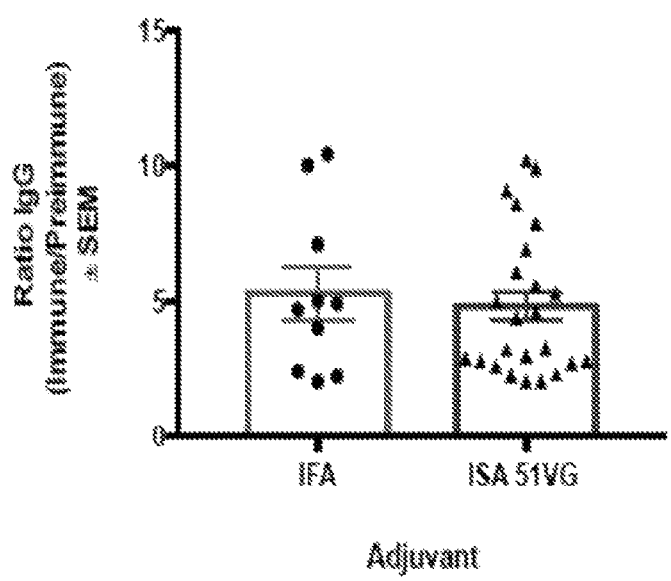
FIG. 13 is a graph showing that both WA and Montanide ISA 51VG adjuvants induce immunity to the canine EGFR p553 peptide.
Figure 14:
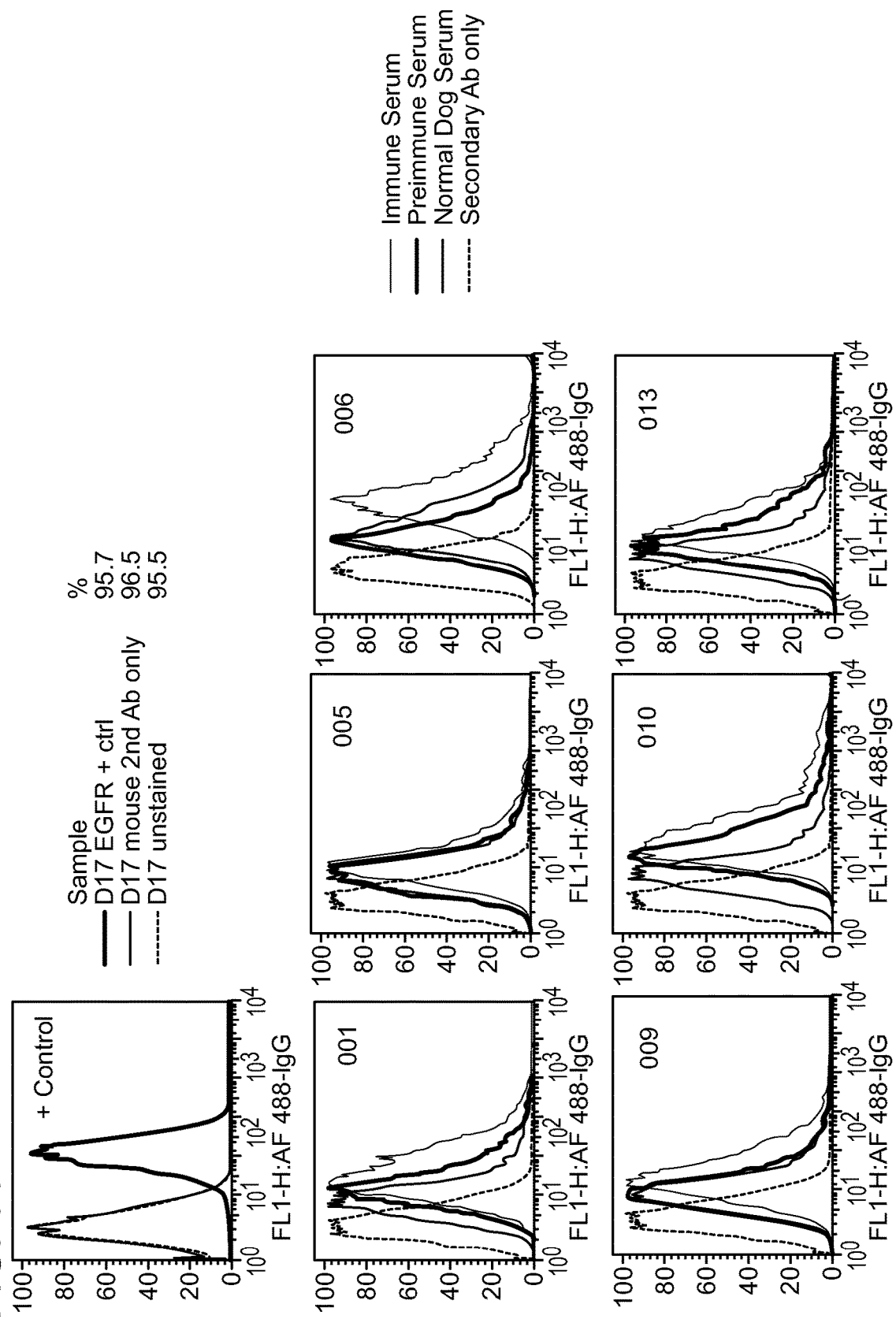
FIG. 14 is a graph showing canine immune sera bind an EGFR bearing canine cancer cell line (termed D17). This is a flow cytometry figure showing that the immune sera (orange lines) shift cells to the right side of the diagrams (indicative of positive binding).
Figure 15:
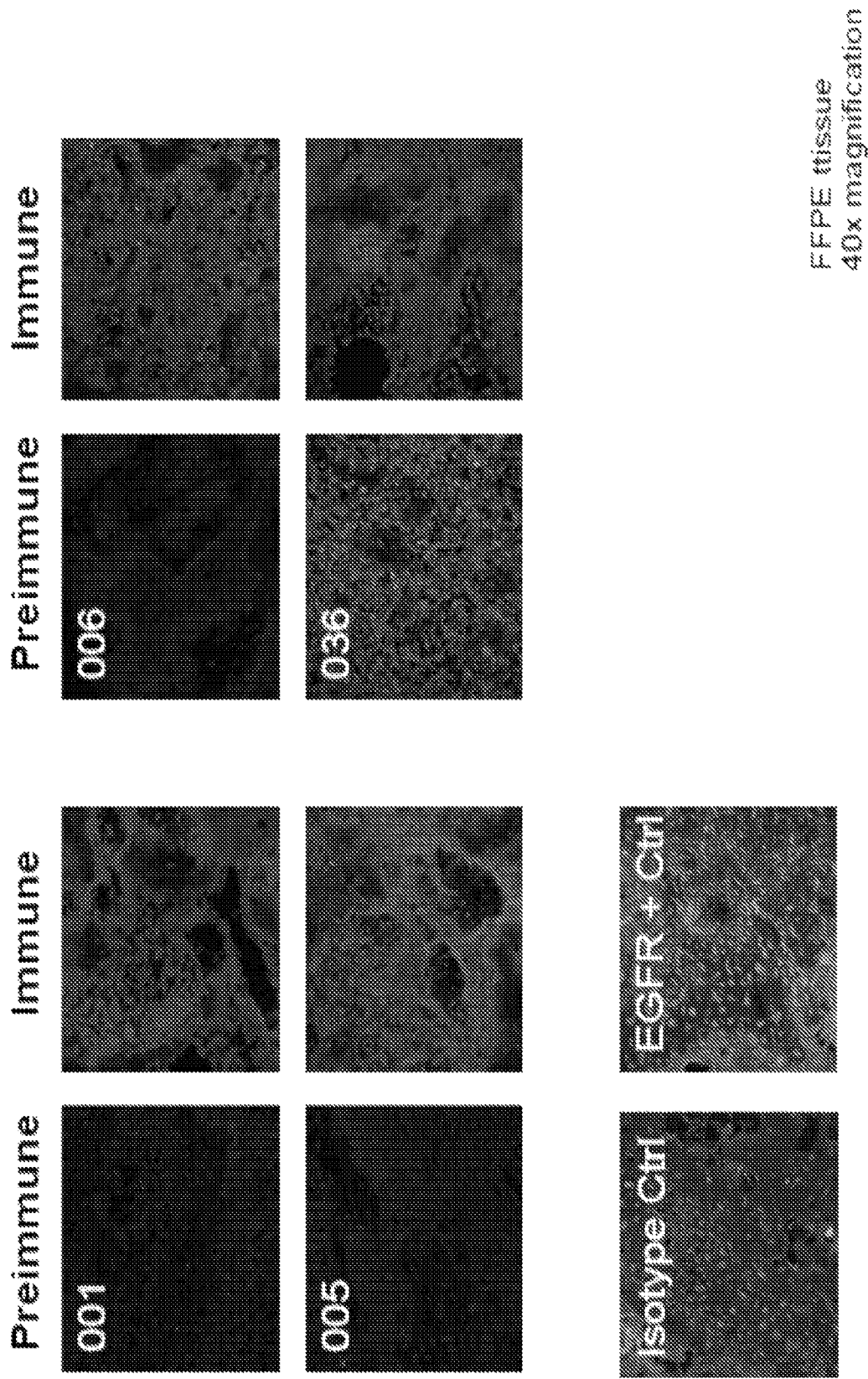
FIG. 15 is a graph showing sera from EGFR p553 immune dogs bind tumor sections of canine osteosarcoma.
Figure 16:
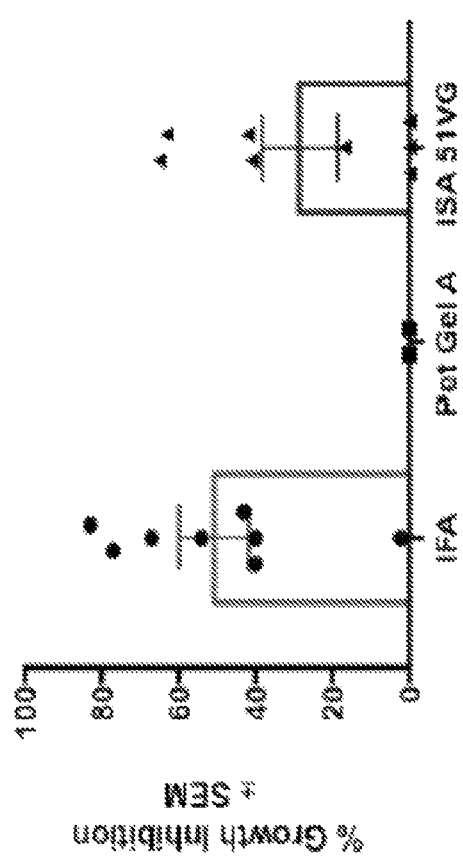
FIG. 16 is a graph showing serum from EGFR p553 immunized canine recipients inhibit human A431 (EGFR expressing) tumor cell growth in vitro.

We next examined the immune responses of canine cEGFR p553 (SEQ ID NO: 15) in dogs. Dogs immunized with cEGFR p553 (SEQ ID NO: 15), combined or formulated with either of the following adjuvants: 1) IFA+LymeVax or 2) Montanide ISA 51VG+LymeVax. Both formulations induced immunity as measured by significant IgG response levels (see FIG. 13 showing 53% positive IgG response using IFA and 70% positive IgG response using Montanide ISA 51VG). The immune response in the immunized dogs was confirmed to be specific to the pharmaceutical composition comprising the cEGFR p553 (SEQ ID NO: 15) and adjuvant (see FIG. 14 and FIG. 15). FIG. 14 shows that sera from dogs immunized with canine cEGFR p553 (SEQ ID NO: 15) in Montanide ISA 51VG adjuvant bind an EGFR bearing canine cancer cell line (termed D17). This is a flow cytometry figure showing that the immune sera (orange lines) shift cells to the right side of the diagrams (indicative of positive binding). Likewise, canine cEGFR p553 (SEQ ID NO: 15) immune sera bound to EGFR on canine osteosarcoma (FIG. 15). FIG. 15 is an immunofluorescent stain of thin sections of canine osteosarcoma using four representative serum from dogs immunized with canine cEGFR p553 (SEQ ID NO: 15)+adjuvant. As illustrated, immune sera bind cells within the osteosarcoma samples while the signal with preimmune serum is significantly lower. Moreover, serum from canine recipients inhibit human A431 (EGFR expressing) tumor cell growth in vitro (FIG. 16). The pharmaceutical composition comprising the cEGFR p553 (SEQ ID NO: 15) and adjuvant showed remarkable in vitro growth inhibition when tested using A431 cells. Using the canine cEGFR p553 (SEQ ID NO: 15) and adjuvant immune sera from the immunized dogs, the Montanide ISA 51VG and IFA adjuvant combinations with cEGFR p553 (SEQ ID NO: 15) were compared to Pet Gel A adjuvant combination. The results in FIG. 16 showed 87.5% growth inhibition using IFA, and 62.5% growth inhibition using Montanide ISA 51VG, when compared to 0% growth inhibition using Pet Gel A.

Canine cancers represent a significant advance in experimental therapeutics, in that the subjects are outbred, allow for a scaled up assessment of immunization protocols, and bear ErbB family tumor associations in a manner that resembles human patients (Burton J et al. (2014) *Vet Clin Small Anim* 44:977-987). Additional experiments will evaluate dosing of a canine EGFR peptide sequence (SEQ ID NO: 15) based on our existing EGFR peptides for the induction of murine antibody and T cell anti-tumor immunity. These dosing studies will include the use of significant numbers of canine recipients of 2-fold increases and 2-fold decreasing amounts of canine cEGFR p553 (SEQ ID NO: 15)+adjuvant, to a total of 50-fold differences. Titers and specificity of anti-canine cEGFR p553 (SEQ ID NO: 15) will be examined in a manner identical to those studies described herein. Experiments will also be designed to analyze the biological anti-tumor responses of peptide induced canine antibodies with those of cetuximab.

Example 4: Combination Immunotherapies in Canine Cancer

A. Methods
(i) Animal Studies

Animal studies are conducted at the Veterinary Cancer Center (VCC) of Norwalk, CT. Animals will be divided into two groups: early stage (stage I and II) and late stage (III & IV), relevant to specific studies described below. Early and late stage disease is determined by standards of clinical care (examination, histology and lab workup) and by imaging (X-ray, CT, ultrasound, where appropriate). Regular imaging will be performed to provide data for tumor numbers and size prior to treatment, during treatment, and post treatment (as many as 4 visits). Pre- and post-treatment punch biopsy, when possible, and/or surgical tissues will be obtained for IHC and analysis by Yale Pathology. Because anti-PD therapy has shown to work in broad spectrum of cancer types in human cancers, we will not limit the enrollment of canine patients with specific cancer types but open to all solid tumors. Hematopoietic malignancies were excluded in this study due to our focus of study in tumor microenvironment. All animals will be further studied with immunological analyses which are critical for this study. Our early studies, which are now validated in human clinical trials, indicate that intrinsic immune response to cancer is an important prerequisite for success of anti-PD therapy.

(ii) Canine Studies

Canine patients, as carefully imaged and staged above, will be immunized and boosted with canine EGFR p553 peptide (SEQ ID NO: 15) emulsified in Montanide ISA51 VG and boosted at day 21. We will examine antibody responses to self (canine) EGFR, HER2, and HER3 by ELISA and by flow cytometry with EGFR-expressing canine and human cell lines. We will also assess binding to related ErbB proteins, HER2 and HER3. Finally, we will assess peripheral T cell immunity to EGFR p533 peptide from immunized canine patients. Pre- and Post-therapy tumor biopsies will be stained for antibody and specific T cell subsets (Th1, Th2, Treg, Th17, CD3, CD4, CD8) by IHC and flow cytometry. Tumors will be assessed for EGFR, HER2 and HER3 expression by IHC.

(iii) Peptide Preparation

Peptide will be synthesized and purified by a commercial vendor (GenScript) similar to that utilized in pilot studies (>95% purity and verified by both HPLC and mass spectrometry) and tested for endotoxin and sterility. The synthetic EGFR p553 peptide is based on canine EGFR residues 553-598 (IKCAHYIDGPHCVKTCPAG) (SEQ ID NO: 15). The peptide does not have extensive homology to canine proteins outside of the ErbB family. The peptide includes conserved, surface exposed residues of ErbB proteins (Table 1). It is important to note that the entire p553 EGFR sequence is 95% identical between dogs and man. Thus, immunity in dogs is directly relevant to breaking immune tolerance in humans (which can be easily confirmed by antibody binding to human EGFR).

(iv) IACUC Protocol and Immunization of Animals

The present study will enroll statistically significant numbers of canine cancer patients; 20 animals (10 EGFR p533 peptide (SEQ ID NO: 15) immunized; 10 sham immunized), not including patients treated by combination PD and vaccination therapy. Patient numbers are chosen to obtain statistical significance for vaccine responses (>4-fold increases in antibody titer) based on prior studies in canine vaccine models and as published criteria for comparative oncology in canine hosts (Wang C Y et al. (2005) *Vaccine* 23:2049-2056; Burton J et al. (2014) *Vet Clin Small Anim* 44:977-987; Thamm D H et al. (2015) *Vet J* 205:226-232). In brief, 7 animals per immunization group will allow for statistical significance. The veterinary oncologist will randomly assign animals to the experimental or control groups. Humane ethical treatment will allow patients to be treated with chemotherapy and/or radiation standard of care for individual tumor types. For these studies, canine patients will be enrolled without regard to breed, age, or gender, but will have confirmed evidence of the presence of EGFR/HER2 tumors based on standard laboratory immunohistochemistry. As defined below, EGFR immunization combined with anti-PD therapies will be examined for anti-tumor antibodies by ELISA and flow cytometry, as well as immunohistochemistry for infiltration of T cells and antibody into tumors (when obtained by tumor biopsy).

The vaccine formulation design allows assessment of two target antigens (Lyme and EGFR) to determine if a lack of response may be due to immune compromised animals (and/or immune tolerance to the self EGFR peptide). A second group of ten will be immunized with Montanide ISA51 VG with (or without) EGFR p553 (2 mg/kg). From Clinical Trials database, Montanide ISA51 VG has already been utilized as an adjuvant in dozens of human cancer immunization clinical trials, including melanoma (MART-1, Tyrosinase, GP100, MAGE, NYESO-1), as well as hepatocellular carcinoma, bladder and breast cancer, sarcoma, prostate and ovarian cancers (Clinical Trials database). Sera will be collected prior to vaccination (day 0), prior to boost (day 21), day 28 and on day 50-60 post-immunization and tested for antibodies against the immunizing peptide.

(v) Antibody and T Cell Analyses

EGFR p553 antisera will be evaluated for antibody binding to the both canine and human EGFR, HER2 and HER3 (R&D Systems) by ELISA. These ErbB family members are frequently co-expressed on a variety of human, canine, and murine tumor types. The immunization will be regarded as efficacious if >4 fold titers are found over pre-immune serum signals in individual animals. CD4 T cell responses will be assessed by conventional proliferation assays towards EGFR peptide (and control peptides) as previously published (Mamula M J et al. (1999) *J. Biol. Chem* 274: 22321-7). In brief, $10^5$ PBMCs from canine patients (both pre- and post-immune samples) will be incubated with titrations of EGFR p553 or scrambled peptide sequence control for 48h. Proliferation will be assessed with $^3$H-thymidine for the last 18h of culture.

As described in detail below, tumor tissues and TILs will be carefully examined by IHC and flow cytometry. These markers will include PD-L1, FoxP3 (Treg), intracellular T-bet/IFN-γ (Th1), GATA-3/IL-4 (Th2) and IL-17 (Th17) and perforin/granzyme B (activity of CTL) in addition to CD3, CD4 and CD8 cells. These studies will be performed in parallel with the EGFR monotherapy vaccination analyses.

TIL will be isolated from freshly excised specimens and analyzed by flow cytometry using the same mAb to validate findings by IHC. We will perform ELISPOT analysis to determine responses of freshly isolated CD4+ and CD8+ TIL to identify tumor antigen-specific T cell response. Tumor growth (or lack thereof), and degree of metastases, where appropriate, will be assessed pre-, during and post treatment as described above. For example, patients with osteosarcoma will have lung X-rays performed throughout treatment, the primary site for metastasis. Treatment groups will be compared in tumor growth and metastases to the vast retrospective data at the VCC and other institutions for standard of care therapies of individual tumor types. This approach is essentially identical to that utilized in the validation of HER2 specific ADXS-HER2R vaccine trials in canine cancer (Mason N J et al. (2016) *Clin Cancer Res* 22:4380-4390).

Based on our pilot studies of EGFR peptide immunizations in mice and now in limited numbers of dogs, we observed a robust antibody response in dogs vaccinated with canine EGFR p533 (SEQ ID NO: 15). Should we see low titers of antibody, this may necessitate us rethinking our dosing and/or adjuvant scheme. We have pilot studies from two EGFR immune dogs with evidence of TILs, though we have no existing data on the specific subsets, kinetics, cytokine profiles of TILs.

B. EGFR Peptide and Anti-PD Combination Therapy

Currently anti-PD therapy is only approved for treating late stage human cancer with disseminated metastases, which may limit maximum efficacy of this therapy. Based on the adaptive resistance hypothesis (Taube J M et al. (2012) *Science Translational Medicine* 4:127ra137; Dong H et al. (2002) *Nat Med* 8(8)):793-800), the efficacy of anti-PD therapy is largely determined by two critical parameters in tumor microenvironment (TME), PD-L1 expression and the presence of tumor infiltrating lymphocytes (TILs) (Topalian S L et al. (2012) *N Engl J Med* 366(26)2443-54; Sznol M et al. (2013) *Clin Cancer Res* 19(5):1021-34). Our previous study demonstrates an increased expression of PD-L1 and the presence of TILs in early stage I/II compared to lesser expression in stage III/IV human lung cancer (Velcheti V et al. (2014) *Lab Invest* 94(1):107-16). Thus, anti-PD therapy could be more effective for treating early stage human cancer compared to late stage disease. Standard of care for early stage human cancer consists of surgery, radiation therapy, and chemotherapy, though strong justification exists to conduct clinical trials of anti-PD therapy in early stage cancer patients. The efficacy of early anti-PD therapy in canine cancer would provide supporting data for future clinical trials in human cancer.

A large fraction of human cancers (up to 40% in melanoma and ~80% in prostate cancer) have only minimal lymphocytic infiltration and lack B7-H1 expression. Accumulated data indicate that these human patients are not responding to anti-PD therapy in general, an outcome we believe will be similarly found in canine cancer patients. We will test several new approaches to increase inflammatory immune responses as an approach to facilitate combination therapy. Our previous studies indicate that immunization with engineered EGFR induces a broad antibody response, which leads to destruction of tumors via ADCC and recruitment of T cells. This provides an excellent opportunity to test combinatory approach with anti-PD therapy. In addition, we will similarly test anti-4-1BB antibodies, which are agonists to preferentially stimulate CD8+ T cell responses and promote infiltration of T cells to the TME. Finally, we will test the approach of blocking PD-1H, a homolog of PD-1 receptor with coinhibitory function for T cell response, in order to enhance T cell responses and recruitment of T cells to the TME.

PD-1/PD-L1 immune regulatory pathway. There is ample evidence that metastatic and primary solid tumors express tumor antigens that can be recognized by the patient's own T cells. In addition, there is marked infiltration of inflammatory immune cells in a significant portion of human cancers. This suggests that human cancers can be both antigenic and immunogenic. However, the nature and extent of inflammatory responses and their roles in the progression of cancers are poorly understood. While evidence of spontaneous host immunity against cancer cells exists, it is typically insufficient to suppress tumor progression. Studies completed in our laboratories and others over the past two decades shed light on immune evasion by cancers. Central to the ability of cancer cells to evade immune destruction is the immunoglobulin-like protein, B7-H1 (PD-L1), which is constitutively expressed in many human cancers as well as host cells in the tumor microenvironment. Expression of cell surface B7-H1 as well as its RNA can be upregulated by IFN-γ, the most potent B7-H1 inducers identified so far (Dong H et al. (2002) *Nat Med* 8(8)):793-800; Zou W et al. (2016) *Sci Transl Med* 8(328):328rv4). B7-H1 appears to be a major ligand in vivo for its receptor, PD-1, to deliver an inhibitory signal to T cells, leading to dysfunction of T-cell responses in the tumor microenvironment. On the other hand, B7-H1 is also a receptor that transmits an anti-apoptotic signal to prevent the death of cancer cells (Chen L et al. (2013) Nat Rev Immunol 13(4):227-42).

The mechanisms underlying B7-H1/PD-1 mediated suppression include the induction of apoptosis, anergy and exhaustion of recently activated effector T cells. Therefore, antitumor T cell immunity is suppressed by B7-H1/PD-1 in the tumor microenvironment (TME). This explains, at least in part, why the presence of peripheral T cell responses and the presence of tumor-infiltrating lymphocytes (TIL) do not lead to the regression of cancers, a mechanism called the adaptive resistance (Taube J M et al. (2012) Science Translational Medicine 4:127ra137). Currently anti-PD therapy, including administration of anti-PD-1 or anti-PD-L1 mAb is shown to be effective in a broad spectrum and a significant fraction of
treatment-refractory human solid tumors and hematopoietic cancers. Anti-PD therapy was FDA approved for the treatment of late stage malignancies of melanoma, lung cancer, renal cell carcinoma, Hodgkin's lymphoma, head and neck cancer and bladder cancer (Chen et al. (2015) J Clin Invest 125(9):3384-91). It is clear that anti-PD therapy is the most efficacious and broad spectrum cancer drug available for late stage human cancers.

As described herein, we will use anti-PD therapy in combination with the EGFR peptide pharmaceutical or vaccine compositions described herein to treat early stage cancer. Currently, mouse tumor models have been employed extensively for testing therapeutic efficacy of new approaches and therapeutic agents. Unfortunately, the results from these studies do not predict clinical outcomes in the majority of cases. We will use canine cancer patients as a predictor of clinical response in human patients. We will determine whether clinical response rate of anti-PD therapy can be further increased. Our studies showed that a major hurdle that prevents anti-PD therapy in some patients is due to the lack of immune infiltration of tumors. We will determine inflammatory infiltration to those tumors as a mechanism to enhance anti-PD therapy in spontaneous canine cancers.

(i) EGFR Vaccination Strategies

As described herein, we have identified determinants that are essentially identical between mouse, canine and human EGFR (p580; Table 4). Moreover, the sequence is highly homologous between EGFR, HER2, HER3, and HER4 (Table 1).

(ii) EGFR p580 Immunization Elicits Mouse Antibodies that Bind EGFR, HER2 and HER3, and Inhibit the Growth of Tumor Cells In Vivo and In Vitro See section Example 2, B.(iv)-(vi), supra.

(iii) Canine EGFR p553 (SEQ ID NO: 15) Immunization of Dogs with Spontaneous EGFR See section Example 3, B.(iv), supra.

While the clinical observations are encouraging, immune responses of human cancer to anti-PD therapy have yet to be elucidated. Because anti-PD therapy is largely modulating TME, it is critical to study those affected tumor tissues. Although it is possible to perform multiple biopsies in human patients, quantity and quality of biopsy specimens are limited. We will work closely with the owners of canine patients to obtain biopsy specimens in primary and metastatic tumors for our study and will use these specimens to address scientific questions which could not otherwise be addressed in human studies. More importantly, canine cancer model will allow us to treat early stage canine patients to obtain invaluable information for the future design of clinical trials in human patients. Another innovative aspect of the invention is in examining new molecules and pathways that may overcome the resistance to anti-PD therapy. We will further assess T cell and anti-tumor antibody responses in a carefully controlled systematic manner. We will work on two additional molecular pathways, 4-1BB and PD-1H, in which their regulatory function of T cell responses and anti-tumor potential. We will include these therapies in combination with EGFR vaccination and/or radiation therapy. Therefore, this study will provide preclinical data to define and overcome pathways of primary resistance to anti-PD-1 therapy.

(iv) Treatment of Early Stage Cancers by Anti-PD Therapy and Pharmaceutical and Vaccine Compositions of p553 (SEQ ID NO: 15)

We will test whether anti-PD therapy has an improved clinical response rate and benefit in early disease compared to late stage cancers. To test this hypothesis, we will first examine the heterogeneity of canine tumors using the method called tumor microenvironment ("TME") classification (Mason N J et al. (2016) Clin Cancer Res 22:4380-4390). In this study, we will use two cohorts of canine tumor specimens, one from archival specimens (VCC and the Yale University Section of Comparative Medicine) and a second from freshly collected specimens in our cancer therapy trial. The retrospective study with large numbers of archival specimens will give us a more thorough understanding of immune responses of canine tumor in the TME. In addition, the use of large pieces of tumor tissues by surgical excision could prevent variation due to heterogeneity. The prospective study will serve to validate our findings in the retrospective study and provide further insights for functional analysis.

We have completed extensive analyses of PD-L1 expression in human cancers. We have developed customized 11-IC methods to analyze human B7-H1 expression using a specific mAb, clone 5H1, in both frozen (Dong H et al. (2002) Nat Med 8(8)):793-800) and FFPE tissues (Taube J M et al. (2012) Science Translational Medicine 4:127ra137). We evaluated B7-H1 expression and TIL in 42 specimens from patients undergoing anti-PD-1 therapy (Topalian S L et al. (2012) N Engl J Med 366(26)2443-54), and identified two factors that might dictate the clinical response to anti-PD-1 therapy: expression of cell membrane B7-H1 and presence of TIL in the melanoma TME. B7-H1 expression was detected in all patients responding to anti-PD-1 Abs and none of the 17 B7-H1 negative patients responded. 9 out of 25 patients with B7-H1+ tumors had an objective response (Topalian S L et al. (2012) N Engl J Med 366(26)2443-54). 8 out of 25 patients with B7-H1+ tumors had either a mixed response or a stable disease (unpublished data). These results indicate that B7-H1 plays a critical role in the ability of the TME to evade cancer immunity.

Up to 41% of specimens were double negative (DN) while nearly all B7-H1+ tumors had significant TIL (double positive—DP, 38%), with only one exception (B7-H1+ TIL−) in 110 cases. Importantly, 20% of melanoma specimens were B7-H1− while the presence of TIL was evident (B7-H1− TIL+ subset). Without a significant inflammatory response in the TME, the presence of B7-H1− TIL− (DN) implies a lack of immunogenicity of cancer cells. Therefore, therapeutic development should focus on generation of an inflammatory response or the recruitment of inflammatory cells to the TME. B7-H1+ TIL+(DP) melanomas support an active, ongoing immune response, but this response is held in check by the B7-H1/PD-1 pathway in many tumors (Dong H et al. (2002) *Nat Med* 8(8)):793-800; Huang S M et al. (2013) *Cancer Res* 73:824-33). The presence of B7-H1-TIL+melanomas implicates mechanisms other than B7-H1/PD-1 which play a role in suppression of tumor immunity. Therefore, this subset of cases has a completely different immune response profile, which may require different therapeutic strategies. Our studies also demonstrate that primary and metastatic melanomas have similar profiles of B7-H1 expression and TIL presence.

To profile B7-H1 and tumor infiltrating lymphocytes (TIL) in canine tumor specimens to determine immunological heterogeneity, we will study both archived canine tumor tissues and freshly collected specimens from the clinical trial (see below). We will examine the expression of B7-H1 in canine tumors using IHC methods. Briefly, archived FFPE slides from canine patients will be stained with anti-PD-L1 mAb 6G7-E1 or an isotype-matched control antibody (BD Biosciences, San Jose, CA, USA) which specifically stains canine PD-L1 (Maekawa N et al. (2016) *PLos One* 11(6): e0157176). The staining will be scored as follows: 0, negative; +, focal expression in 5-40% of cancer tissues; ++, focal expression in 40-80% of cancer tissues; and +++, diffuse expression in >80% cancer tissues. We will also examine the TILs in these specimens by anti-CD3/CD4/CD8 mAbs with similar IHC methods.

Previous studies showed that a significant fraction of primary and metastatic human cancers expressed B7-H1. Moreover, B7-H1 expression correlates with objective clinical response to anti-PD-1 therapy (Topalian S L et al. (2012) *N Engl J Med* 366(26)2443-54; Sznol M et al. (2013) *Clin Cancer Res* 19(5):1021-34). Here we will extend our studies using canine tumor specimens. A major cytokine for the upregulation of B7-H1 is IFN-γ (2-4), which is largely produced by TILs. Therefore, we should also see an association of B7-H1 expression with the presence of TILs. These studies will demonstrate that canine and human tumors use a similar mechanism to escape immune attack. Thus, these findings will help us to determine subsets of canines who will be treated differently (see below). Moreover, we will be able to determine expression of B7-H1 in stromal tissue, as this might also affect the response to anti-PD therapy. Statistical considerations: We will compare prevalence of the four B7-H1/TIL subgroups in canine tumors to corresponding human cancers. We will check whether frequencies in the two types of tumors are systematically different using a variant of the chi-square test for independence in a 2-by-4 contingency table (e.g. collapsing the last two groups, or the Fisher-Freeman-Halton exact test Our study provides important and fundamental information for further studies of immune responses in canine tumors. B7-H1 in FFPE tissue is denatured and difficult to stain because the majority of commercially available mAbs only recognize conformational epitopes. Although we have not yet used 6G7-E1 extensively for staining, we have developed a robust method to renature human B7-H1 on FFPE slides and to stain with 5H1 mAb (Dong H et al. (2002) *Nat Med* 8(8)):793-800). The heterogeneity of B7-H1 expression in tumors may cause variation in clinical specimen analysis (Taube J M et al. (2012) *Science Translational Medicine* 4:127ra137; Dong H et al. (2002) *Nat Med* 8(8)):793-800). It is possible for us to obtain larger biopsy specimens in canines to overcome this problem. The cut-point of >5% for positivity of B7-H1 might not be optimal, and % positive cells as a continuous variable will also be studied. Similarly, the intensity of staining, rather than % positivity might yield more accurate results. Pathological grouping of B7-H1 expression is semi-quantitative at best. In addition to cancer cells, the expression of B7-H1 is also found in other stromal cells, which may also contribute to poor immune responses. Manual interpretation will enable us to determine if expression of B7-H1 by noncancer stromal cells such as microglia, fibroblasts, macrophages, dendritic cells, T and B cells can be independent markers which correlate with decreased immune responses. Pathology slides will be reviewed by a pathologist.

To compare clinical response to anti-PD therapy between early vs. late stage cancer: Our previous study in human lung cancer showed that significant more patients in early stage cancer TME (stage I and II) expressed B7-H1 and had TIL presence than those in late stage diseases (stage III and IV)(30). These observations implicate that early stage cancer may have a better response rate to anti-PD therapy. This is a clinically significant issue since this may provide a new option to patients with early stage diseases in addition to standard care. We will test this possibility in canine cancer models. Canines with early cancer will be treated with anti-PD-1 mAb at 3 mg/kg every three weeks for total three doses and clinical responses including tumor regression (PR, CR and SD), progression free survival (PFS) and long-term survival will be documented. Canine patients treated with standard care will be served as the controls. All canine patients in this study will be biopsied for cancer tissues before, during and after the treatment for immunological analysis (see other sections).

Similar to human diseases, canine cancers also express B7-H1 (35). While a fraction of canine patients will respond to the treatment while others will not, we expect to see a higher response rate and better survival in the early than the late stage cancers. This will provide direct evidence to support similar trials in human cancer. With the study of biopsy specimens, we should be able to correlate these clinical findings with PD-L1 expression, TIL presence as well as other immunological parameters (see below) and to provide important information for our understanding of the immune response and resistance to anti-PD therapy. 50 canine patients will satisfy statistical analysis.

We will not focus on specific types but all types of cancer to treat based on clinical experience from human studies. While this may increase the variation of response rate and difficulty in data analysis, we believe that this may still be a good option. Anti-PD therapy has shown to be effective in the majority of solid tumors based on current studies in 25 different types of solid tumors and the clinical response rates are in the ranges of 20-40% (Zou W et al. (2016) *Sci Transl Med* 8(328):328rv4; Chen et al. (2015) *J Clin Invest* 125(9):3384-91). Therefore, with sufficient numbers of individual canine cancer types enrolled in our trial, we will resolve this potential variation via statistical analysis. If our initial results show dramatic different outcomes in certain types of canine cancer, we will specifically recruit these types of cancer for further studies as independent cohorts. We will not conduct a traditional dose escalation study while employing standard effective dose of human drugs. It is possible that antibodies may have different pharmacology features and we will consider conducing a small "phase I"-like dose escalating trial if we observe a significant clinical response in our trial and/or significant response in certain types of cancer. Both anti-PD-1 and anti-PD-L1 mAb and selecting drug candidates will be generated. Nevertheless, these mAbs will be generated in mice and it is possible that these mAb may elicit neutralizing antibodies. If this is a significant issue, we will modify our protocol to shorten the treatment. For example, a total of two doses administered every other week to decrease the potential risks. It is important that this clinical treatment protocol provides important source for sample analysis which will be addressed below. We understand that biopsy specimens from the early stage cancer may not be sufficient to perform more extensive analysis of immune responses. Therefore, we will do such studies in the late stage cancer patients.

(v) To Explore New Combination Strategies for Treatment-Refractory Cancer.

We will focus our efforts in enhancing immunity in the T1 tumor to promote inflammatory infiltration (EGFR vaccine and radiation) and in the T3 tumors to break T cell tolerance/exhaustion (antagonistic PD-1H and agonist 4-1BB mAb). We will first determine if these approaches promote the adaptive resistance mechanism, namely induction of B7-H1, upon induction of local inflammation (conversion to the T3 tumor). A major subset of human patients who are refractory to anti-PD therapy is in the T1 tumor category which grow progressively without significant TIL in the TME (31). We find that a significant fraction of human melanoma and lung cancer patients have only minimal lymphocytic infiltration, lack B7-H1, and do not respond to anti-PD therapy. It is thus important to attract inflammatory responses to TME. We will explore several methods to increase inflammatory immune responses in the TME with the goal of rapidly translating them to clinical trials. This will provide important information for future clinical trials in combination anti-PD therapy with these modalities (EGFR vaccine, PD-1H antagonist, CD137 agonist and radiation) in human cancer patients.

To characterize immunological responses before, during and after anti-PD therapy: We will determine the nature of T cell dysfunction in cancer tissues before treatment and will compare the changes during and after treatment with PD therapy with and without EGFR vaccination. In some large tissue samples, we will analyze the phenotypes and functions of TIL in cancer specimens using IHC, flow cytometry and in vitro functional analysis. Identical numbers of patients with matched tumor types (osteosarcoma, for example) will be treated with anti-PD monotherapy, or combined with EGFR vaccination. Both specific immune responses in the TME as well as tumor growth and metastases will be assessed. Osteosarcoma, melanoma and hemangiosarcoma patients will be relatively easily acquired in statistically significant numbers for both mono and combined therapy.

TIL will be isolated from freshly excised specimens and analyzed by flow cytometry using the same mAb to validate findings by IHC. These freshly isolated specimens will be prospectively collected and snap frozen, and only larger specimens will be used for flow cytometry. Standard operating procedures are in place for isolating TIL. In addition, we will perform ELISPOT analysis to determine responses of freshly isolated CD4+ and CD8+ TIL to identify tumor antigen-specific T cell response. 96-well plates will be coated with the capture antibody specific for canine IFN-γ (secreted by all CTL), IL-17 and IL-4. CD137 has been shown to be a potent costimulatory molecule on T cell response (Melero I et al. (1997) *Nat Me* 3(6)682-5; Wolff M et al. (2007) *Blood* 110:201-210; Wehler T et al. (2007) *Blood* 109:365-373; Melero I et al. (1997) *Life Sci* 60:2035-2041; Wilcox R et al. (2002) *J Clin Invest* 109:651-659; Wilcox R et al. (2004) 103:177-184; Narazaki H et al. (2010) *Blood* 115:1941-1948) and the majority of tumor antigen-specific T cells coexpress both PD-1 and CD137 (Wolff M et al. (2007) *Blood* 110:201-210; Gros A et al. (2016) *Nat Med* 22(4):433-8; Inozume T et al. (2010) *J Immunother* 33(9):956-64; Gros A et al. (2014) *J Clin Invest* 124(5):2246-59). An important aspect of our studies is to correlate PD-1 expression with the functional analyses described above in cancer specimens and we will perform co-staining in both IHC and isolated T cells.

The study of cancer biopsies provides a unique opportunity to analyze immune responses before, during and after the treatment. These studies will provide unique insights in human immune responses in anti-PD therapy because it is in general difficult to perform in humans. With these analyses, we should be able to identify specific subsets of human T cells and their dysfunctional status under the influence of the B7-H1/PD-1 pathway. In addition, this approach can help identify subsets of T cells that may be selectively modified. These findings will provide important information for our understanding of the immune response and resistance to anti-PD therapy. We will start with 50 prospective samples for the IHC experiments and these specimens will be used to conduct pilot experiments to demonstrate the distribution of biomarker staining and used for flow cytometry studies. These initial studies will be used for analysis of biomarker distribution, which will be validated on a separate cohort of additional at least 50 samples.

Expression analysis of immune modulatory molecules and studies of T cell function in human specimens will help establish correlations between molecular expression and potential dysfunction of T cell responses in the TME. The specimens can be small and thus insufficient to perform extensive molecular and functional analyses. Our priority is in IHC staining for molecular analysis. If specimens are sufficiently large, such as those from excisional biopsy, we will perform flow cytometry analysis and ELISPOT to validate findings. Freshly isolated T cells without restimulation may not give sufficient signal for detection. An alternative method to detect antigen-specific T cells is to use anti-CD137, which has shown to be a reliable marker for the T cells pre-exposed to antigens (Wolff M et al. (2007) *Blood* 110:201-210; Wehler T et al. (2007) *Blood* 109:365-373; Gros A et al. (2016) *Nat Med* 22(4):433-8; Gros A et al. (2014) *J Clin Invest* 124(5):2246-59).

Overall, the studies described herein addresses several important and fundamental questions of cancer immunotherapy. As emphasized throughout, the work will utilize canine hosts with spontaneous cancers, in stages and development that highly resemble human cancer progression. The key biological pathways in canine cancer and their tumor microenvironment, from the expression of PD-1 and PD-L1 surface proteins and tumor specific markers (EGFR, HER2, HER3), as well as intracellular signaling and tumor oncogenes (cKit, Ras, etc.) are virtually identical to those found in human disease. It is clear that anti-PD therapy works in a small fraction of human cancer, though the precise mechanisms that explain failure are not understood. Moreover, emerging studies indicate that anti-PD therapy may be significantly more effective when utilized in combination with selected chemotherapies, radiation, targeting mAb, or immunization. This studies described herein will address many of these topics, namely, the features of response in early vs. late stage disease to anti-PD therapy and the role of influencing the anti-tumor immune repertoire in the tumor microenvironment relative to the success or failure of anti-PD therapy. All of these approaches and knowledges we learn from these studies could be immediately translated to improving the therapeutic strategies in human cancer.

REFERENCES

All publications, patent. applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed:

1. A pharmaceutical composition comprising:
   a.) a peptide consisting of a sequence that is at least 90% identical to an amino acid sequence selected from the group consisting of SEQ ID: NOs: 1-15, wherein the peptide is optionally chemically conjugated to a carrier protein; and
   b.) an adjuvant.

2. The pharmaceutical composition of claim 1, wherein the peptide consists of a sequence that is at least 95% identical to the amino acid sequence selected from the group consisting of SEQ ID: NOs: 1-15.

3. The pharmaceutical composition of claim 1, wherein the peptide is an ErbB peptide.

4. The pharmaceutical composition of claim 1, wherein the adjuvant comprises at least one of a *Borrelia* antigen, a receptor agonist, an immunomodulatory agent, or a combination of any thereof.

5. The pharmaceutical composition of claim 4, wherein the adjuvant comprises at least one *Borrelia* antigen that is Outer Surface Protein A (OspA), Outer Surface Protein C (OspC), or a combination thereof.

6. The pharmaceutical composition of claim 4, wherein the adjuvant comprises at least one *Borrelia* antigen that induces antibodies against at least one of the *Borrelia* spp. selected from the group consisting of *Borrelia afzelii, Borrelia americana, Borrelia andersonii, Borrelia anserina, Borrelia baltazardii, Borrelia bavariensis, Borrelia bissettii, Borrelia brasiliensis, Borrelia burgdorferi, Borrelia californiensis, Borrelia carolinensis, Borrelia caucasica, Borrelia coriaceae, Borrelia crocidurae, Borrelia dugesii, Borrelia duttonii, Borrelia garinii, Borrelia graingeri, Borrelia harveyi, Borrelia hermsii, Borrelia hispanica, Borrelia japonica, Borrelia kurtenbachii, Borrelia latyschewii, Borrelia lonestari, Borrelia lusitaniae, Borrelia mazzottii, Borrelia merionesi, Borrelia micron, Borrelia miyamotoi, Borrelia parkeri, Borrelia persica, Borrelia recurrentis, Borrelia sinica, Borrelia spielmanii, Borrelia tanukii, Borrelia texasensis, Borrelia theileri, Borrelia tillae, Borrelia turcica, Borrelia turdi, Borrelia turicatae, Borrelia valaisiana, Borrelia venezuelensis, Borrelia vincentii, Borrelia burgdorferi* B31, *Borrelia burgdorferi* N40, *Borrelia burgdorferi* JD1, and *Borrelia burgdorferi* 297.

7. The pharmaceutical composition of claim 4, wherein the adjuvant comprises at least one receptor agonist that is selected from the group consisting of CpG oligodeoxynucleotides 7909 (CpG 7909), Monophosphoryl lipid A (MPL), lipopolysaccharide (LPS), polyI:C, R848, and combinations of any thereof.

8. The pharmaceutical composition of claim 4, wherein the adjuvant or immunomodulatory agent is from about 5% to about 80% volume/volume (v/v).

9. The pharmaceutical composition of claim 8, wherein the adjuvant or immunomodulatory agent is about 5%, about 10%, about 15%, about 20%, about 25%, about 30%, about 35%, about 40%, about 45%, about 50%, about 55%, about 60%, about 65%, about 70%, about 75%, or about 80% (v/v).

10. The pharmaceutical composition of claim 1, wherein the adjuvant comprises at least one receptor agonist of a Toll-Like Receptor (TLR), wherein the TLR is selected from the group consisting of TLR1, TLR2, TLR3, TLR4, TLR5, TLR6, TLR7, TLR8, TLR9, TLR10, TLR11, TLR12, and TLR13.

11. The pharmaceutical composition of claim 10, wherein:
(i) the TLR is TLR3, and the at least one receptor agonist of a TLR is a TLR3 agonist that is polyI:C;
(ii) the TLR is TLR4, and the at least one receptor agonist of a TLR is a TLR4 agonist that is MPL;
(iii) the TLR is TLR7, and the at least one receptor agonist of a TLR is a TLR7 agonist that is R848; and/or
(iv) the TLR is TLR9, and the at least one receptor agonist of a TLR is a TLR9 agonist that is CpG.

12. The pharmaceutical composition of claim 1, wherein the adjuvant comprises at least one immunomodulatory agent selected from the group consisting of complete Freunds adjuvant (CFA), incomplete Freunds adjuvant (IFA), LTK63, dimethyl dioctadecyl-ammonium bromide (DDA), lipophilic quaternary ammonium salt-DDA, Trehalose dimycolate and synthetic derivatives, DDA-MPL, DDA-TDM, DDA-TDB, IC-31, aluminum salts, aluminum hydroxyide, aluminum phosphate, potassium aluminum phosphate, water-in-oil emulsion, mannide monooleate, vegetable grade (VG) oleic acid, ISA-51 VG, ISA-720, microparticles, immuno stimulatory complexes, liposomes, virosomes, virus-like particles, cholera toxin, heat-labile toxin from *E. coli*, lipoproteins, dendritic cells, IL-12, GM-CSF, nanoparticles, a nanoemulsion of soybean oil and emulsifying agents and ethanol, AS04, Thymalfasin, and combinations of any thereof.

13. The pharmaceutical composition of claim 12, wherein the immunomodulatory agent is CFA, IFA, or ISA-51 VG.

14. The pharmaceutical composition of claim 1, wherein the adjuvant is a combination of ISA-51 VG and *Borrelia burgdorferi* Bacterin, or a combination of ISA-51 VG and CpG 7909.

15. A vaccine composition comprising the pharmaceutical composition of claim 1.

16. A method of treating an EGFR-positive cancer in a subject comprising administering to the subject the pharmaceutical composition of claim 1, or the vaccine composition of claim 15, in combination with radiation therapy.

17. A method of treating an EGFR-positive cancer in a subject comprising administering to the subject the pharmaceutical composition of claim 1 or the vaccine composition of claim 15.

18. The method of claim 17, wherein the pharmaceutical composition or vaccine composition is administered at a dose of 0.4 mg to 40 mg per kg body weight.

19. The method of claim 17, wherein the subject has received or is receiving chemotherapy or radiotherapy, or has undergone or is undergoing surgery.

20. The method of claim 17, wherein the subject is a mammal, wherein the mammal is a dog or human.

21. A method of treating an EGFR-positive cancer in a subject comprising conjointly administering to the subject the pharmaceutical composition of claim 1, and an anti-cancer, or chemotherapeutic agent.

22. A method of treating an EGFR-positive cancer in a subject comprising conjointly administering to the subject the pharmaceutical composition of claim 1, and an anti-PD therapy.

23. The method of claim 22, wherein the anti-PD therapy is blockade of the PD-1/PDL1 pathway, a monoclonal antibody to PD-1, or a monoclonal antibody to B7-H1/PD-L1.

24. The method of claim 21 or 22, wherein the pharmaceutical composition, anti-cancer agent, chemotherapeutic agent, and/or anti-PD therapy is administered separately, concomitantly, sequentially, or repeatedly.

25. The method of claim 24, wherein the pharmaceutical composition, anti-cancer agent, chemotherapeutic agent, and/or anti-PD therapy is administered intravenously, intramuscularly, subcutaneously, or intraperitoneally.

26. The method of claim 21 or 22, wherein the pharmaceutical composition is administered before, during or after administering the anti-cancer agent, chemotherapeutic agent, or anti-PD therapy.

27. The method of claim 21 or 22, wherein the anti-cancer agent, chemotherapeutic agent, or anti-PD therapy, is administered at a dose within a range of 0.001 to 1000 mcg/kg.

28. A pharmaceutical composition comprising:
a.) a peptide consisting of an amino acid sequence of any one of SEQ ID: NOs: 1-15, wherein the peptide is optionally conjugated to a carrier protein; and
b.) an adjuvant.

* * * * *